(12) United States Patent
Shasky et al.

(10) Patent No.: US 10,273,515 B2
(45) Date of Patent: Apr. 30, 2019

(54) ENZYME COMPOSITIONS AND USES THEREOF

(71) Applicant: Novozymes A/S, Bagsvaerd (DK)

(72) Inventors: Jeffrey Shasky, Davis, CA (US); Debbie Yaver, Davis, CA (US); Donna Moyer, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 37 days.

(21) Appl. No.: 15/316,477

(22) PCT Filed: Jun. 4, 2015

(86) PCT No.: PCT/US2015/034179
§ 371 (c)(1),
(2) Date: Dec. 5, 2016

(87) PCT Pub. No.: WO2015/187935
PCT Pub. Date: Dec. 10, 2015

(65) Prior Publication Data
US 2017/0204441 A1 Jul. 20, 2017

Related U.S. Application Data

(60) Provisional application No. 62/093,230, filed on Dec. 17, 2014, provisional application No. 62/009,018, filed on Jun. 6, 2014.

(51) Int. Cl.

| | |
|---|---|
| *C12N 9/02* | (2006.01) |
| *C12N 9/08* | (2006.01) |
| *C12N 9/24* | (2006.01) |
| *C12N 9/42* | (2006.01) |
| *C12P 19/02* | (2006.01) |
| *C12P 19/14* | (2006.01) |

(52) U.S. Cl.
CPC ............ *C12P 19/14* (2013.01); *C12N 9/0004* (2013.01); *C12N 9/0065* (2013.01); *C12N 9/24* (2013.01); *C12N 9/248* (2013.01); *C12N 9/2437* (2013.01); *C12N 9/2445* (2013.01); *C12P 19/02* (2013.01); *C12Y 111/01006* (2013.01); *C12Y 302/01021* (2013.01); *C12Y 302/01037* (2013.01); *C12Y 302/01091* (2013.01); *C12Y 302/01176* (2013.01); *C12P 2201/00* (2013.01); *C12P 2203/00* (2013.01); *Y02E 50/16* (2013.01)

(58) Field of Classification Search
CPC combination set(s) only.
See application file for complete search history.

(56) References Cited

U.S. PATENT DOCUMENTS

| | | | |
|---|---|---|---|
| 8,044,264 B2* | 10/2011 | Lopez de Leon | ........................... C12Y 302/0102 435/320.1 |
| 2011/0078829 A1 | 3/2011 | Tang et al. | |
| 2012/0278952 A1 | 11/2012 | Vlasenko et al. | |
| 2013/0288299 A1 | 10/2013 | Spodsberg | |
| 2013/0309723 A1 | 11/2013 | Huang et al. | |
| 2014/0030770 A1 | 1/2014 | Spodsberg | |
| 2014/0113336 A1 | 4/2014 | Spodsberg | |
| 2014/0127758 A1 | 5/2014 | Shaghasi et al. | |
| 2014/0308705 A1 | 10/2014 | Morant et al. | |
| 2015/0079527 A1 | 3/2015 | Rasmussen et al. | |

FOREIGN PATENT DOCUMENTS

| | | |
|---|---|---|
| WO | 2008088724 A2 | 7/2008 |
| WO | 2009108941 A2 | 9/2009 |
| WO | 2013028927 A1 | 2/2013 |

OTHER PUBLICATIONS

Biodegradation and biological treatments of cellulose, hemicellulose and lignin: an overview (Int Microbiol(2002) 5: 53-63) (Year: 2002).*

\* cited by examiner

*Primary Examiner* — Kagnew H Gebreyesus
(74) *Attorney, Agent, or Firm* — Robert Starnes

(57) ABSTRACT

The present invention relates to enzyme compositions and processes of producing and using the compositions for the saccharification of lignocellulosic material.

9 Claims, 13 Drawing Sheets
Specification includes a Sequence Listing.

SEQUENCE LISTING

<160> NUMBER OF SEQ ID NOS: 106

<210> SEQ ID NO 1
<211> LENGTH: 1730
<212> TYPE: DNA
<213> ORGANISM: Talaromyces leycettanus

<400> SEQUENCE: 1

```
atggcgtccc tcttctcttt caagatgtac aaggctgctc tcgtcctgtc ttctctcctg      60
gccgctacgc aggctcagca ggccggcact ctcacgacgg agacccatcc gtccctgaca     120
tggcagcaat gctcggccgg tggcagctgc accacccaga acggcaaggt cgtcatcgat     180
gcgaactggc gttgggtgca cagcacgagc ggaagcaaca actgctacac cggcaatacc     240
tgggacgcta ccctatgccc tgacgatgtg acctgcgccg ccaactgtgc gctggacggt     300
gccgactact cgggcaccta cggagtgacc accagcggca actccctccg cctcaacttc     360
gtcacccagg cgtcacagaa gaacgtcggc tcccgtcttt acctgatgga gaatgacaca     420
acctaccaga tcttcaagct gctgaaccag gagttcacct ttgatgtcga tgtgtccaac     480
ctgccgtaag tgacttacca tgaacccctg acgctatctt cttgttggct cccagctgac     540
tggccaattc aagctgcggc ttgaacggtg ctctctacct ggtggccatg gacgccgatg     600
gtggcatggc caagtacccc accaacaagg ctggtgccaa gtacggtacc gggtactgcg     660
actcccagtg tccccgcgac ctcaagttca tcaatggcga ggccaacgtc gagggctggc     720
agccgtcgtc caacgatccc aactctggca ttggcaacca cggatcctgc tgcgcggaga     780
tggatatctg ggaggccaac agcatctcca atgctgtcac tccccacccg tgcgacactc     840
ccggccaggt gatgtgcacc ggtaacaact gcggtggcac atacagcact actcgctatg     900
```

```
cgggcacttg cgatcccgac ggctgcgact tcaacccccta ccgcatgggc aaccacagct    960
tctacggccc taaacagatc gtcgatacca gctcgaagtt caccgtcgtg acgcagttcc   1020
tcacggatga cggcacctcc accggcaccc tctctgaaat ccgccgcttc tatgtccaga   1080
acggccaggt gatcccgaac tcggtgtcga ccatcagtgg cgtgagcggc aactccatca   1140
ccaccgagtt ctgcactgcc agaagcagg ccttcggcga cacggacgac ttctcaaagc    1200
acggcggcct gtccggcatg agcgctgccc tctctcaggg tatggttctg gtcatgagtc   1260
tgtgggatga tgtgagtttg atggacaaac atgcgcgttg acaaagagtc aagcagctga   1320
ctgagatgtt acagcacgcc gccaacatgc tctggctcga cagcacctac ccgaccaacg   1380
cgacctcctc cacccccggt gccgcccgtg aacctgcga catctcgtcc ggtgtccctg     1440
cggatgtcga atccaacgac cccaacgcct acgtggtcta ctcgaacatc aaggttggtc   1500
ccatcggctc gaccttcagc agcagcggct ctggatcttc ttcctctagc tccaccacta   1560
ccacgaccac cgcttcccca accaccacga cctcctccgc atcgagcacc ggcactggag   1620
tggcacagca ctggggccag tgtggtggac agggctggac cggccccaca acctgcgtca   1680
gcccttatac ttgccaggag ctgaacccctt actactacca gtgtctgtaa              1730
```

<210> SEQ ID NO 2
<211> LENGTH: 532
<212> TYPE: PRT
<213> ORGANISM: Talaromyces leycettanus

<400> SEQUENCE: 2

```
Met Ala Ser Leu Phe Ser Phe Lys Met Tyr Lys Ala Ala Leu Val Leu
1               5                   10                  15

Ser Ser Leu Leu Ala Ala Thr Gln Ala Gln Gln Ala Gly Thr Leu Thr
            20                  25                  30

Thr Glu Thr His Pro Ser Leu Thr Trp Gln Gln Cys Ser Ala Gly Gly
        35                  40                  45

Ser Cys Thr Thr Gln Asn Gly Lys Val Val Ile Asp Ala Asn Trp Arg
    50                  55                  60

Trp Val His Ser Thr Ser Gly Ser Asn Asn Cys Tyr Thr Gly Asn Thr
65                  70                  75                  80

Trp Asp Ala Thr Leu Cys Pro Asp Asp Val Thr Cys Ala Ala Asn Cys
                85                  90                  95

Ala Leu Asp Gly Ala Asp Tyr Ser Gly Thr Tyr Gly Val Thr Thr Ser
            100                 105                 110

Gly Asn Ser Leu Arg Leu Asn Phe Val Thr Gln Ala Ser Gln Lys Asn
        115                 120                 125

Val Gly Ser Arg Leu Tyr Leu Met Glu Asn Asp Thr Thr Tyr Gln Ile
    130                 135                 140

Phe Lys Leu Leu Asn Gln Glu Phe Thr Phe Asp Val Asp Val Ser Asn
145                 150                 155                 160

Leu Pro Cys Gly Leu Asn Gly Ala Leu Tyr Leu Val Ala Met Asp Ala
                165                 170                 175

Asp Gly Gly Met Ala Lys Tyr Pro Thr Asn Lys Ala Gly Ala Lys Tyr
            180                 185                 190

Gly Thr Gly Tyr Cys Asp Ser Gln Cys Pro Arg Asp Leu Lys Phe Ile
        195                 200                 205

Asn Gly Glu Ala Asn Val Glu Gly Trp Gln Pro Ser Ser Asn Asp Pro
    210                 215                 220
```

Asn Ser Gly Ile Gly Asn His Gly Ser Cys Cys Ala Glu Met Asp Ile
225                 230                 235                 240

Trp Glu Ala Asn Ser Ile Ser Asn Ala Val Thr Pro His Pro Cys Asp
            245                 250                 255

Thr Pro Gly Gln Val Met Cys Thr Gly Asn Asn Cys Gly Gly Thr Tyr
        260                 265                 270

Ser Thr Thr Arg Tyr Ala Gly Thr Cys Asp Pro Asp Gly Cys Asp Phe
    275                 280                 285

Asn Pro Tyr Arg Met Gly Asn His Ser Phe Tyr Gly Pro Lys Gln Ile
290                 295                 300

Val Asp Thr Ser Ser Lys Phe Thr Val Val Thr Gln Phe Leu Thr Asp
305                 310                 315                 320

Asp Gly Thr Ser Thr Gly Thr Leu Ser Glu Ile Arg Arg Phe Tyr Val
            325                 330                 335

Gln Asn Gly Gln Val Ile Pro Asn Ser Val Ser Thr Ile Ser Gly Val
        340                 345                 350

Ser Gly Asn Ser Ile Thr Thr Glu Phe Cys Thr Ala Gln Lys Gln Ala
    355                 360                 365

Phe Gly Asp Thr Asp Asp Phe Ser Lys His Gly Gly Leu Ser Gly Met
370                 375                 380

Ser Ala Ala Leu Ser Gln Gly Met Val Leu Val Met Ser Leu Trp Asp
385                 390                 395                 400

Asp His Ala Ala Asn Met Leu Trp Leu Asp Ser Thr Tyr Pro Thr Asn
            405                 410                 415

Ala Thr Ser Ser Thr Pro Gly Ala Ala Arg Gly Thr Cys Asp Ile Ser
        420                 425                 430

Ser Gly Val Pro Ala Asp Val Glu Ser Asn Asp Pro Asn Ala Tyr Val
    435                 440                 445

Val Tyr Ser Asn Ile Lys Val Gly Pro Ile Gly Ser Thr Phe Ser Ser
450                 455                 460

Ser Gly Ser Gly Ser Ser Ser Ser Ser Thr Thr Thr Thr Thr Thr Thr
465                 470                 475                 480

Ala Ser Pro Thr Thr Thr Thr Ser Ser Ala Ser Ser Thr Gly Thr Gly
            485                 490                 495

Val Ala Gln His Trp Gly Gln Cys Gly Gly Gln Gly Trp Thr Gly Pro
        500                 505                 510

Thr Thr Cys Val Ser Pro Tyr Thr Cys Gln Glu Leu Asn Pro Tyr Tyr
    515                 520                 525

Tyr Gln Cys Leu
    530

<210> SEQ ID NO 3
<211> LENGTH: 1898
<212> TYPE: DNA
<213> ORGANISM: Talaromyces leycettanus

<400> SEQUENCE: 3
atgcggtctc tcctggctct tgcccctacc ctgctcgcgc tgttgttca ggctcagcaa        60 accatgtggg gtcaatgtaa gttctttca ctgcttacca tgtataatct ttgatatcaa       120
gcatcatatc tgactcacgt tttaggcggt ggtcagggct ggaccggacc taccatctgt      180
gtagcaggcg cgacatgcag cacacagaac ccttgtaagt cgggccttca tcaaaacttc     240
aacatcacca cctcgatgga gcaggagttg acctgatctt tacccttagg gtatgcgcag    300 tgcacccag cacctaccgc gccgacgacc ttgcaaacaa caactacgac gagctcgaaa      360

```
tcgtccacga ccacgagctc gaagtcgtcc acgaccacag gtggaagtgg cggtggaact      420
acgacctcaa cgtcagccac catcaccgcg gctccatctg gtaacccata ctccggatac      480
cagctctatg tgaaccagga atactcgtcc gaggtgtacg cgtctgctat tccttcccct      540
accggcactc tggtcgcgaa ggcaagcgcc gcggcagagg tgccatcttt cctgtggctg      600
taagtttttt tgaccttgaa tgaacgccct gtcctctacg agtggccgca ggagctaatt      660
gagatgccaa tgaacaggga cactgcctcc aaggtgccac tgatgggcac ttacttgcag      720
gatatccagg cgaagaacgc tgctggcgcc aaccccccat atgccggtca attcgtggtt      780
tacgacttgc cggatcgtga ttgcgctgca ttggccagca atggagagta ctccattgct      840
aacaatggtg ttgccaacta caaggcttac atcgactcca tccgcgcgct tcttgttcaa      900
tactcgaacg tccatgtcat ccttgtgatc ggtgagctat tgcagtctcg ctttaaagca      960
tttgactaga tcaatgtcgc taatggtacc taccgcacag agcccgacag cttggccaac     1020
cttgtcacca acctgaatgt tcagaagtgt gctaatgctc agagtgctta cctggagtgc     1080
atcaactatg ccctcactca gttgaacctc aagaacgttg ctatgtacat cgatgctggt     1140
gcgtgaacct tccctagtca gcccaaaata actgaaataa agagacggag tgtactgatt     1200
gtcatgcagg tcatgctgga tggctcggct ggcccgccaa ccttagcccg ccgctcaac     1260 tctttgcttc cgtataccag aatgcaagct ccccagctgc cgttcgcggc ctggcaacca     1320
acgtggccaa ctataatgcc tggtcgatcg ccacttgccc atcttacacc caaggcgacc     1380
ccaactgcga cgagcagaaa tacatcaacg ctctggctcc attgcttcag caacagggat     1440
ggtcatcagt tcactttatc accgataccg gtaagtctgc ctgtcctgcc aaccatgcgt     1500
tcaagagcgt tgcaatccta accatgctgg tatcttccag gccgtaacgg tgtccagcct     1560
accaagcaga atgcctgggg tgactggtgc aacgttatcg gaaccggctt cggtgtccgt     1620
cccaccacca acactggcga tccattggag gatgctttcg tctgggtcaa gcctggtggt     1680
gagagtgatg gtacttccaa ctccacttcg cctcgctacg acgcccactg cggttacagt     1740
gatgctcttc agcctgctcc tgaggctggt acctggttcg aggtaagctt ctgcatactg     1800
agatcgagaa tcctgaaagg gttaacctgc taatgcttcg gtgtttgata taggcttact     1860
ttgagcaact ccttaccaac gccaaccct ctttctaa                              1898
```

<210> SEQ ID NO 4
<211> LENGTH: 464
<212> TYPE: PRT
<213> ORGANISM: Talaromyces leycettanus

<400> SEQUENCE: 4

```
Met Arg Ser Leu Leu Ala Leu Ala Pro Thr Leu Leu Ala Pro Val Val
1               5                   10                  15

Gln Ala Gln Gln Thr Met Trp Gly Gln Cys Gly Gly Gln Gly Trp Thr
            20                  25                  30

Gly Pro Thr Ile Cys Val Ala Gly Ala Thr Cys Ser Thr Gln Asn Pro
        35                  40                  45

Trp Tyr Ala Gln Cys Thr Pro Ala Pro Thr Ala Pro Thr Thr Leu Gln
    50                  55                  60

Thr Thr Thr Thr Thr Ser Ser Lys Ser Ser Thr Thr Ser Ser Lys
65                  70                  75                  80

Ser Ser Thr Thr Thr Gly Gly Ser Gly Gly Thr Thr Thr Ser Thr
                85                  90                  95
```

```
Ser Ala Thr Ile Thr Ala Ala Pro Ser Gly Asn Pro Tyr Ser Gly Tyr
            100                 105                 110

Gln Leu Tyr Val Asn Gln Glu Tyr Ser Glu Val Tyr Ala Ser Ala
    115                 120                 125

Ile Pro Ser Leu Thr Gly Thr Leu Val Ala Lys Ala Ser Ala Ala Ala
130                 135                 140

Glu Val Pro Ser Phe Leu Trp Leu Asp Thr Ala Ser Lys Val Pro Leu
145                 150                 155                 160

Met Gly Thr Tyr Leu Gln Asp Ile Gln Ala Lys Asn Ala Ala Gly Ala
                165                 170                 175

Asn Pro Pro Tyr Ala Gly Gln Phe Val Val Tyr Asp Leu Pro Asp Arg
                180                 185                 190

Asp Cys Ala Ala Leu Ala Ser Asn Gly Glu Tyr Ser Ile Ala Asn Asn
                195                 200                 205

Gly Val Ala Asn Tyr Lys Ala Tyr Ile Asp Ser Ile Arg Ala Leu Leu
                210                 215                 220

Val Gln Tyr Ser Asn Val His Val Ile Leu Val Ile Glu Pro Asp Ser
225                 230                 235                 240

Leu Ala Asn Leu Val Thr Asn Leu Asn Val Gln Lys Cys Ala Asn Ala
                245                 250                 255

Gln Ser Ala Tyr Leu Glu Cys Ile Asn Tyr Ala Leu Thr Gln Leu Asn
                260                 265                 270

Leu Lys Asn Val Ala Met Tyr Ile Asp Ala Gly His Ala Gly Trp Leu
            275                 280                 285

Gly Trp Pro Ala Asn Leu Ser Pro Ala Ala Gln Leu Phe Ala Ser Val
            290                 295                 300

Tyr Gln Asn Ala Ser Ser Pro Ala Ala Val Arg Gly Leu Ala Thr Asn
305                 310                 315                 320

Val Ala Asn Tyr Asn Ala Trp Ser Ile Ala Thr Cys Pro Ser Tyr Thr
                325                 330                 335

Gln Gly Asp Pro Asn Cys Asp Glu Gln Lys Tyr Ile Asn Ala Leu Ala
                340                 345                 350

Pro Leu Leu Gln Gln Gln Gly Trp Ser Ser Val His Phe Ile Thr Asp
                355                 360                 365

Thr Gly Arg Asn Gly Val Gln Pro Thr Lys Gln Asn Ala Trp Gly Asp
                370                 375                 380

Trp Cys Asn Val Ile Gly Thr Gly Phe Gly Val Arg Pro Thr Thr Asn
385                 390                 395                 400

Thr Gly Asp Pro Leu Glu Asp Ala Phe Val Trp Val Lys Pro Gly Gly
                405                 410                 415

Glu Ser Asp Gly Thr Ser Asn Ser Thr Ser Pro Arg Tyr Asp Ala His
                420                 425                 430

Cys Gly Tyr Ser Asp Ala Leu Gln Pro Ala Pro Glu Ala Gly Thr Trp
                435                 440                 445

Phe Glu Ala Tyr Phe Glu Gln Leu Leu Thr Asn Ala Asn Pro Ser Phe
                450                 455                 460

<210> SEQ ID NO 5
<211> LENGTH: 3060
<212> TYPE: DNA
<213> ORGANISM: Aspergillus fumigatus

<400> SEQUENCE: 5
atgagattcg gttggctcga ggtggccgct ctgacggccg cttctgtagc caatgcccag      60
```

```
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga atcgctgacg aaccatcgt agctggcgtt    1080
ggcgctgtca tgtgttccta caatcaaatc aacaacagct acggttgtca aaacagtcaa   1140
actctcaaca agtcctcaa ggctgagctg ggcttccaag gcttcgtcat gagtgactgg    1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttcccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataaccccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggccttgagct acaccacctt tggttactct   2400
caccttcggg ttcaggccct caatagttcg agttcggcat atgtcccgac tagcggagag   2460
```

```
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccct cctgaaggct ggcggcgctc ctggtggtaa ccctacccctt   2700 tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag     3060
```

<210> SEQ ID NO 6
<211> LENGTH: 863
<212> TYPE: PRT
<213> ORGANISM: Aspergillus fumigatus

<400> SEQUENCE: 6

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
                260                 265                 270
```

```
Gly Phe Gln Gly Phe Val Met Ser Asp Trp Ser Ala His His Ser Gly
            275                 280                 285

Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
            450                 455                 460

Gln Ala Ile Gln Arg Glu Val Ile Ser Asn Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
            530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685
```

```
Gly Glu Ile Gly Ser Ala Ala Asp Tyr Leu Tyr Pro Glu Gly Leu Lys
    690             695                 700
Arg Ile Thr Lys Phe Ile Tyr Pro Trp Leu Asn Ser Thr Asp Leu Glu
705                 710                 715                 720
Asp Ser Ser Asp Asp Pro Asn Tyr Gly Trp Glu Asp Ser Glu Tyr Ile
                725                 730                 735
Pro Glu Gly Ala Arg Asp Gly Ser Pro Gln Pro Leu Leu Lys Ala Gly
            740                 745                 750
Gly Ala Pro Gly Gly Asn Pro Thr Leu Tyr Gln Asp Leu Val Arg Val
        755                 760                 765
Ser Ala Thr Ile Thr Asn Thr Gly Asn Val Ala Gly Tyr Glu Val Pro
    770                 775                 780
Gln Leu Tyr Val Ser Leu Gly Gly Pro Asn Glu Pro Arg Val Val Leu
785                 790                 795                 800
Arg Lys Phe Asp Arg Ile Phe Leu Ala Pro Gly Glu Gln Lys Val Trp
                805                 810                 815
Thr Thr Thr Leu Asn Arg Arg Asp Leu Ala Asn Trp Asp Val Glu Ala
            820                 825                 830
Gln Asp Trp Val Ile Thr Lys Tyr Pro Lys Lys Val His Val Gly Ser
        835                 840                 845
Ser Ser Arg Lys Leu Pro Leu Arg Ala Pro Leu Pro Arg Val Tyr
    850                 855                 860

<210> SEQ ID NO 7
<211> LENGTH: 835
<212> TYPE: DNA
<213> ORGANISM: Penicillium sp. emersonii

<400> SEQUENCE: 7
atgctgtctt cgacgactcg caccctcgcc tttacaggcc ttgcgggcct tctgtccgct      60
cccctggtca aggcccatgg ctttgtccag ggcattgtca tcggtgacca attgtaagtc     120
cctctcttgc agttctgtcg attaactgct ggactgcttg cttgactccc tgctgactcc     180
caacagctac agcgggtaca tcgtcaactc gttccctac gaatccaacc accccccgt      240 catcggctgg ccacgaccg ccaccgacct gggcttcgtc gacggcacag ataccaagg      300 cccggacatc atctgccacc ggaatgcgac gcccgcgccg ctgacagccc ccgtggccgc     360
cggcggcacc gtcgagctgc agtggacgcc gtggccggac agccaccacg gacccgtcat     420
cacctacctg gcgccgtgca acggcaactg ctcgaccgtc gacaagacga cgctggagtt     480
cttcaagatc gaccagcagg gcctgatcga cgacacgagc ccgccgggca cctgggcgtc     540
ggacaacctc atcgccaaca caatagctg gaccgtcacc attcccaaca gcgtcgcccc     600
cggcaactac gtcctgcgcc acgagatcat cgccctgcac tcggccaaca acaaggacgg     660
cgcccagaac taccccagt gcatcaacat cgaggtcacg gcggcggct ccgacgcgcc     720 tgagggtact ctgggcgagg atctctacca tgacaccgac ccgggcattc tggtcgacat     780
ttacgagccc attgcgacgt ataccattcc ggggccgcct gagccgacgt tctag          835

<210> SEQ ID NO 8
<211> LENGTH: 253
<212> TYPE: PRT
<213> ORGANISM: Penicillium sp. emersonii

<400> SEQUENCE: 8

Met Leu Ser Ser Thr Thr Arg Thr Leu Ala Phe Thr Gly Leu Ala Gly
1               5                   10                  15
```

```
Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
 50                  55                  60

Asp Leu Gly Phe Val Asp Gly Thr Gly Tyr Gln Gly Pro Asp Ile Ile
 65                  70                  75                  80

Cys His Arg Asn Ala Thr Pro Ala Pro Leu Thr Ala Pro Val Ala Ala
                 85                  90                  95

Gly Gly Thr Val Glu Leu Gln Trp Thr Pro Trp Pro Ser His His
            100                 105                 110

Gly Pro Val Ile Thr Tyr Leu Ala Pro Cys Asn Gly Asn Cys Ser Thr
            115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
            195                 200                 205

Thr Gly Gly Gly Ser Asp Ala Pro Glu Gly Thr Leu Gly Glu Asp Leu
210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 9
<211> LENGTH: 1520
<212> TYPE: DNA
<213> ORGANISM: Talaromyces leycettanus

<400> SEQUENCE: 9
atggtccatc tttcttccct ggccctggct ttggccgccg gctcgcagct gtatgtgatc      60
catgccatga ctcgagaagt gctcccaaaa ctgactccaa gtctcaatct tagtgcccaa     120
gctgcaggtc ttaacactgc tgccaaagcg attggaaagc tctatttcgg taccgcaacc     180
gacaacccgg agctgtccga cagcacatac atgcaggaga cggataacac cgatgatttc     240
ggccaactca ccccagctaa ctccatgaag gttcgctgac atcttagttc cccccccctt     300
ttgggaatct cgcgcggaga tatgctgagcc ttcaaaacta gtgggatgcc accgagccct     360
ctcagaacac cttcaccttc accaacggtg atcagatcgc aaaccttgct aagagcaacg     420
gtcagatgct gagatgccac aacctggtgt ggtacaacca gttgcccagc tggggtaagc     480
aaccggttct gttaatatca tcagcgtgac cgcatcgatc gtattgcgcg agattggaa     540 agatttgcaa gctaatgtca ctacagtcac cagcggatct tggaccaatg ccacgcttct     600
tgcggccatg aagaaccaca tcaccaacgt tgtgacccac tacaagggac agtgctacgc     660
ttgggatgtt gtcaacgaag gtacgtttcg attcggcttc cctcggaccg tatctgcagg     720
caaaaaggtc aatcaattga caatcgtgat ccccagctct caacgatgat ggcacctacc     780
```

```
gatccaatgt cttctatcag tacatcggcg aggcatacat tcccattgcc tttgcgaccg    840
ctgccgccgc cgatccaaac gcgaagctct actacaacga ctacaacatt gagtaccccg    900
gcgccaaggc caccgccgcc cagaacatcg tcaagatggt caaggcttac ggcgcgaaaa    960
tcgacggtgt cggtctgcaa tctcacttca tcgttggcag caccccctagc cagagctccc   1020
agcagagcaa catggctgct ttcaccgcgc tcggcgtcga ggtcgccatc accgaactgg   1080
atatccgcat gacgttgcct tccaccagtg ctctcttggc ccagcaatcc accgattacc   1140
agagcactgt gtcggcttgc gtgaacactc cgaagtgcat tggtatcacc ctctgggact   1200
ggaccgacaa gtactcctgg gttcccaaca ccttctccgg ccaaggtgac gcctgccccct   1260
gggattctaa ctaccagaag aagcctgcct actacggtat cttgactgcg ctcggaggca   1320
gcgcttccac ctccaccacc accactctgg tgacctccac caggacttcg actacgacca   1380
gcacttcggc cacctccacg tctactggcg ttgctcagca ctggggccag tgcggtggta   1440
tcggctggac agggccgact acctgcgcta gccctacac tgccaggaa ctgaatccct   1500
actactacca gtgcctgtaa                                                1520
```

```
<210> SEQ ID NO 10
<211> LENGTH: 405
<212> TYPE: PRT
<213> ORGANISM: Talaromyces leycettanus

<400> SEQUENCE: 10
```

```
Met Val His Leu Ser Ser Leu Ala Leu Ala Ala Gly Ser Gln
1               5                   10                  15

Leu Ala Gln Ala Ala Gly Leu Asn Thr Ala Lys Ala Ile Gly Lys
            20                  25                  30

Leu Tyr Phe Gly Thr Ala Thr Asp Asn Pro Glu Leu Ser Asp Ser Thr
            35                  40                  45

Tyr Met Gln Glu Thr Asp Asn Thr Asp Asp Phe Gly Gln Leu Thr Pro
50                  55                  60

Ala Asn Ser Met Lys Trp Asp Ala Thr Glu Pro Ser Gln Asn Thr Phe
65                  70                  75                  80

Thr Phe Thr Asn Gly Asp Gln Ile Ala Asn Leu Ala Lys Ser Asn Gly
                85                  90                  95

Gln Met Leu Arg Cys His Asn Leu Val Trp Tyr Asn Gln Leu Pro Ser
            100                 105                 110

Trp Val Thr Ser Gly Ser Trp Thr Asn Ala Thr Leu Leu Ala Ala Met
            115                 120                 125

Lys Asn His Ile Thr Asn Val Val Thr His Tyr Lys Gly Gln Cys Tyr
130                 135                 140

Ala Trp Asp Val Val Asn Glu Ala Leu Asn Asp Asp Gly Thr Tyr Arg
145                 150                 155                 160

Ser Asn Val Phe Tyr Gln Tyr Ile Gly Glu Ala Tyr Ile Pro Ile Ala
                165                 170                 175

Phe Ala Thr Ala Ala Ala Ala Asp Pro Asn Ala Lys Leu Tyr Tyr Asn
            180                 185                 190

Asp Tyr Asn Ile Glu Tyr Pro Gly Ala Lys Ala Thr Ala Ala Gln Asn
            195                 200                 205

Ile Val Lys Met Val Lys Ala Tyr Gly Ala Lys Ile Asp Gly Val Gly
        210                 215                 220

Leu Gln Ser His Phe Ile Val Gly Ser Thr Pro Ser Gln Ser Ser Gln
225                 230                 235                 240
```

Gln Ser Asn Met Ala Ala Phe Thr Ala Leu Gly Val Glu Val Ala Ile
                245                 250                 255

Thr Glu Leu Asp Ile Arg Met Thr Leu Pro Ser Thr Ser Ala Leu Leu
            260                 265                 270

Ala Gln Gln Ser Thr Asp Tyr Gln Ser Thr Val Ser Ala Cys Val Asn
        275                 280                 285

Thr Pro Lys Cys Ile Gly Ile Thr Leu Trp Asp Trp Thr Asp Lys Tyr
    290                 295                 300

Ser Trp Val Pro Asn Thr Phe Ser Gly Gln Gly Asp Ala Cys Pro Trp
305                 310                 315                 320

Asp Ser Asn Tyr Gln Lys Lys Pro Ala Tyr Tyr Gly Ile Leu Thr Ala
                325                 330                 335

Leu Gly Gly Ser Ala Ser Thr Ser Thr Thr Thr Thr Leu Val Thr Ser
            340                 345                 350

Thr Arg Thr Ser Thr Thr Thr Ser Thr Ser Ala Thr Ser Thr Ser Thr
            355                 360                 365

Gly Val Ala Gln His Trp Gly Gln Cys Gly Gly Ile Gly Trp Thr Gly
        370                 375                 380

Pro Thr Thr Cys Ala Ser Pro Tyr Thr Cys Gln Glu Leu Asn Pro Tyr
385                 390                 395                 400

Tyr Tyr Gln Cys Leu
            405

<210> SEQ ID NO 11
<211> LENGTH: 1197
<212> TYPE: DNA
<213> ORGANISM: Trichophaea saccata

<400> SEQUENCE: 11

```
atgcgtacct tctcgtctct tctcggtgtt gcccttctct tgggtgcagc taatgcccag     60
gtcgcggttt ggggacagtg tggtggcatt ggttactctg ctcgacaac ctgcgctgcg    120
ggaacgactt gtgttaagct gaacgactac tactcccaat gccaacccgg cggtaccact    180
ttgacaacca ccaccaaacc cgccaccact accactacca ccacggcaac ttctccctca    240
tcttctcccg gattaaatgc cctggcacaa agagcggcc ggtacttcgg tagtgcaact    300
gacaacccag agctctccga tgcggcatac attgccatcc tgagcaacaa aaacgagttt    360
gggatcatca cgcctggaaa ctcgatgaaa tgggatgcta ctgaaccgtc ccgcgggagt    420
ttctcgttca ctggtggaca gcaaattgtt gattttgcgc agggcaatgg cgggctatc    480
agaggccata ctcttgtctg gtactcccag ttgccgtcct gggttactag cggaaacttc    540
gataaagcta cattgacatc gatcatgcaa aatcacatta caactcttgt cagccactgg    600
aagggccagc tcgcctactg ggatgttgtc aacgaagcat tcaacgatga tggcactttc    660
cgtcaaaacg tgttctacac aaccattgga gaggactaca tccagctcgc cttcgaagcc    720
gcccgtgccg ccgacccgac cgcaaagctc tgcatcaacg actacaacat cgagggcact    780
ggagccaagt caacagccat gtacaatctc gtctcgaagc tgaaatccgc cggcgttccc    840
atcgactgta ttggtgttca gggacacctc atcgtcggtg aagttcccac caccatccaa    900
gcaaaccttg cccagtttgc gtctttgggt gtggatgtcg cgatcacgga gctagatatc    960
agaatgacgc tgccatctac gactgcattg ctccagcagc aggctaagga ttacgtctcg   1020
gttgttacag cctgcatgaa tgttcccagg tgtatcggta tcaccatctg ggactacact   1080
gataaatact cttgggtgcc acaaaccttc agcggccagg gcgatgcttg cccatgggat   1140
```

```
gccaacctgc agaagaagcc agcctactcc gctattgcgt ctgctcttgc ggcttga      1197
```

<210> SEQ ID NO 12
<211> LENGTH: 398
<212> TYPE: PRT
<213> ORGANISM: Trichophaea saccata

<400> SEQUENCE: 12

| | | | | | | | | | | | | | | | |
|---|---|---|---|---|---|---|---|---|---|---|---|---|---|---|---|
| Met | Arg | Thr | Phe | Ser | Ser | Leu | Leu | Gly | Val | Ala | Leu | Leu | Gly | Ala | |
| 1 | | | | 5 | | | | | 10 | | | | | 15 | |
| Ala | Asn | Ala | Gln | Val | Ala | Val | Trp | Gly | Gln | Cys | Gly | Gly | Ile | Gly | Tyr |
| | | 20 | | | | | 25 | | | | | 30 | | | |
| Ser | Gly | Ser | Thr | Thr | Cys | Ala | Ala | Gly | Thr | Thr | Cys | Val | Lys | Leu | Asn |
| | | 35 | | | | 40 | | | | | 45 | | | | |
| Asp | Tyr | Tyr | Ser | Gln | Cys | Gln | Pro | Gly | Gly | Thr | Thr | Leu | Thr | Thr | Thr |
| | 50 | | | | | 55 | | | | | 60 | | | | |
| Thr | Lys | Pro | Ala | Thr | Thr | Thr | Thr | Thr | Thr | Ala | Thr | Ser | Pro | Ser | |
| 65 | | | | | 70 | | | | | 75 | | | | | 80 |
| Ser | Ser | Pro | Gly | Leu | Asn | Ala | Leu | Ala | Gln | Lys | Ser | Gly | Arg | Tyr | Phe |
| | | | | 85 | | | | | 90 | | | | | 95 | |
| Gly | Ser | Ala | Thr | Asp | Asn | Pro | Glu | Leu | Ser | Asp | Ala | Ala | Tyr | Ile | Ala |
| | | | 100 | | | | | 105 | | | | | 110 | | |
| Ile | Leu | Ser | Asn | Lys | Asn | Glu | Phe | Gly | Ile | Ile | Thr | Pro | Gly | Asn | Ser |
| | | | 115 | | | | | 120 | | | | | 125 | | |
| Met | Lys | Trp | Asp | Ala | Thr | Glu | Pro | Ser | Arg | Gly | Ser | Phe | Ser | Phe | Thr |
| | 130 | | | | | 135 | | | | | 140 | | | | |
| Gly | Gly | Gln | Gln | Ile | Val | Asp | Phe | Ala | Gln | Gly | Asn | Gly | Gln | Ala | Ile |
| 145 | | | | | 150 | | | | | 155 | | | | | 160 |
| Arg | Gly | His | Thr | Leu | Val | Trp | Tyr | Ser | Gln | Leu | Pro | Ser | Trp | Val | Thr |
| | | | | 165 | | | | | 170 | | | | | 175 | |
| Ser | Gly | Asn | Phe | Asp | Lys | Ala | Thr | Leu | Thr | Ser | Ile | Met | Gln | Asn | His |
| | | | 180 | | | | | 185 | | | | | 190 | | |
| Ile | Thr | Thr | Leu | Val | Ser | His | Trp | Lys | Gly | Gln | Leu | Ala | Tyr | Trp | Asp |
| | | | 195 | | | | | 200 | | | | | 205 | | |
| Val | Val | Asn | Glu | Ala | Phe | Asn | Asp | Asp | Gly | Thr | Phe | Arg | Gln | Asn | Val |
| | 210 | | | | | 215 | | | | | 220 | | | | |
| Phe | Tyr | Thr | Thr | Ile | Gly | Glu | Asp | Tyr | Ile | Gln | Leu | Ala | Phe | Glu | Ala |
| 225 | | | | | 230 | | | | | 235 | | | | | 240 |
| Ala | Arg | Ala | Ala | Asp | Pro | Thr | Ala | Lys | Leu | Cys | Ile | Asn | Asp | Tyr | Asn |
| | | | | 245 | | | | | 250 | | | | | 255 | |
| Ile | Glu | Gly | Thr | Gly | Ala | Lys | Ser | Thr | Ala | Met | Tyr | Asn | Leu | Val | Ser |
| | | | 260 | | | | | 265 | | | | | 270 | | |
| Lys | Leu | Lys | Ser | Ala | Gly | Val | Pro | Ile | Asp | Cys | Ile | Gly | Val | Gln | Gly |
| | 275 | | | | | 280 | | | | | 285 | | | | |
| His | Leu | Ile | Val | Gly | Glu | Val | Pro | Thr | Ile | Gln | Ala | Asn | Leu | Ala | |
| | 290 | | | | | 295 | | | | | 300 | | | | |
| Gln | Phe | Ala | Ser | Leu | Gly | Val | Asp | Val | Ala | Ile | Thr | Glu | Leu | Asp | Ile |
| 305 | | | | | 310 | | | | | 315 | | | | | 320 |
| Arg | Met | Thr | Leu | Pro | Ser | Thr | Thr | Ala | Leu | Leu | Gln | Gln | Gln | Ala | Lys |
| | | | | 325 | | | | | 330 | | | | | 335 | |
| Asp | Tyr | Val | Ser | Val | Val | Thr | Ala | Cys | Met | Asn | Val | Pro | Arg | Cys | Ile |
| | | | 340 | | | | | 345 | | | | | 350 | | |
| Gly | Ile | Thr | Ile | Trp | Asp | Tyr | Thr | Asp | Lys | Tyr | Ser | Trp | Val | Pro | Gln |
| | | | 355 | | | | | 360 | | | | | 365 | | |

```
Thr Phe Ser Gly Gln Gly Asp Ala Cys Pro Trp Asp Ala Asn Leu Gln
    370                 375                 380

Lys Lys Pro Ala Tyr Ser Ala Ile Ala Ser Ala Leu Ala Ala
385                 390                 395
```

<210> SEQ ID NO 13
<211> LENGTH: 2391
<212> TYPE: DNA
<213> ORGANISM: Talaromyces emersonii

<400> SEQUENCE: 13

```
atgatgactc ccacggcgat tctcaccgca gtggcggcgc tcctgcccac cgcgacatgg    60
gcacaggata accaaaccta tgccaattac tcgtcgcagt ctcagccgga cctgtttccc   120
cggaccgtcg cgaccatcga cctgtccttc cccgactgtg agaatggccc gctcagcacg   180
aacctggtgt gcaacaaatc ggccgatccc tgggcccgag ctgaggccct catctcgctc   240
tttacccctcg aagagctgat taacaacacc cagaacaccg ctcctggcgt gccccgtttg   300
ggtctgcccc agtatcaggt gtggaatgaa gctctgcacg gactggaccg cgccaatttc   360
tcccattcgg gcgaatacag ctgggccacg tccttcccca tgcccatcct gtcgatggcg   420
tccttcaacc ggaccctcat caaccagatt gcctccatca ttgcaacgca agcccgtgcc   480
ttcaacaacg ccggccgtta cggccttgac agctatgcgc ccaacatcaa tggcttccgc   540
agtcccctct ggggccgtgg acaggagacg cctggtgagg atgcgttctt cttgagttcc   600
acctatgcgt acgagtacat cacaggcctg cagggcggtg tcgacccaga gcatgtcaag   660
atcgtcgcga cggcgaagca cttcgccggc tatgatctgg agaactgggg caacgtctct   720
cggctggggt tcaatgctat catcacgcag caggatctct ccgagtacta caccccctcag   780
ttcctggcgt ctgctcgata cgccaagacg cgcagcatca tgtgctccta caatgcagtg   840
aatggagtcc caagctgtgc caactccttc ttcctccaga cgcttctccg agaaaacttt   900
gacttcgttg acgacgggta cgtctcgtcg gattgcgacg ccgtctacaa cgtcttcaac   960
ccacacggtt acgcccttaa ccagtcggga gccgctgcgg actcgctcct agcaggtacc  1020
gatatcgact gtggtcagac cttgccgtgg cacctgaatg agtccttcgt agaaggatac  1080
gtctcccgcg gtgatatcga gaatccctc accgtctct actcaaacct ggtgcgtctc  1140
ggctactttg acggcaacaa cagcgagtac cgcaacctca ctggaacga cgtcgtgact  1200
acggacgcct ggaacatctc gtacgaggcc gcggtggaag gtatcaccct gctcaagaac  1260
gacgaacgc tgccgctgtc caagaaggtc cgcagcattg cgctcatcgg tccttgggcc  1320
aatgccacgg tgcagatgca gggtaactac tatggaacgc accgtatct gatcagtccg  1380
ctggaagccg ccaaggccag tgggttcacg gtcaactatg cattcggtac caacatctcg  1440
accgattcta cccagtggtt cgcggaagcc atcgcggcgg cgaagaagtc ggacgtgatc  1500
atctacgccg gtggtattga caacacgatc gaggcagagg acaggaccg cacggatctc  1560
aagtggccgg ggaaccagct ggatctgatc gagcagctca gccaggtggg caagcccttg  1620
gtcgtcctgc agatgggcgg tggccaggtg gattcgtcgt cactcaaggc caacaagaat  1680
gtcaacgctc tggtgtgggg tggctatccc ggacagtcgc gtggtgcggc cctgtttgac  1740
atccttacgg gcaagcgtgc gccggccggt cgtctggtga gcacgcagta cccggccgag  1800
tatgcgacgc agttcccggc caacgacatg aacctgcgtc cgaacggcag caaccccggga  1860
cagacataca tctggtacac gggcacgccc gtgtatgagt tcggccacgg tctgttctac  1920
```

```
acggagttcc aggagtcggc tgcggcgggc acgaacaaga cgtcgacttt cgacattctg    1980
gaccttttct ccacccctca tccgggatac gagtacatcg agcaggttcc gttcatcaac    2040
gtgactgtgg acgtgaagaa cgtcggccac acgccatcgc cgtacacggg tctgttgttc    2100
gcgaacacga cagccgggcc caagccgtac ccgaacaaat ggctcgtcgg gttcgactgg    2160
ctgccgacga tccagccggg cgagactgcc aagttgacga tcccggtgcc gttgggcgcg    2220
attgcgtggg cggacgagaa cggcaacaag gtggtcttcc cgggcaacta cgaattggca    2280
ctgaacaatg agcgatcggt agtggtgtcg ttcacgctga cgggcgatgc ggcgactcta    2340
gagaaatggc ctttgtggga gcaggcggtt ccgggggtgc tgcagcaata a              2391
```

<210> SEQ ID NO 14
<211> LENGTH: 796
<212> TYPE: PRT
<213> ORGANISM: Talaromyces emersonii

<400> SEQUENCE: 14

```
Met Met Thr Pro Thr Ala Ile Leu Thr Ala Val Ala Ala Leu Leu Pro
1               5                   10                  15

Thr Ala Thr Trp Ala Gln Asp Asn Gln Thr Tyr Ala Asn Tyr Ser Ser
            20                  25                  30

Gln Ser Gln Pro Asp Leu Phe Pro Arg Thr Val Ala Thr Ile Asp Leu
        35                  40                  45

Ser Phe Pro Asp Cys Glu Asn Gly Pro Leu Ser Thr Asn Leu Val Cys
    50                  55                  60

Asn Lys Ser Ala Asp Pro Trp Ala Arg Ala Glu Ala Leu Ile Ser Leu
65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser His Ser Gly Glu Tyr Ser Trp
        115                 120                 125

Ala Thr Ser Phe Pro Met Pro Ile Leu Ser Met Ala Ser Phe Asn Arg
    130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Thr Tyr Ala Tyr Glu Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Phe Asn Ala Ile Ile Thr Gln Gln Asp Leu Ser Glu Tyr
                245                 250                 255

Tyr Thr Pro Gln Phe Leu Ala Ser Ala Arg Tyr Ala Lys Thr Arg Ser
            260                 265                 270

Ile Met Cys Ser Tyr Asn Ala Val Asn Gly Val Pro Ser Cys Ala Asn
        275                 280                 285

Ser Phe Phe Leu Gln Thr Leu Leu Arg Glu Asn Phe Asp Phe Val Asp
```

-continued

```
            290                 295                 300
Asp Gly Tyr Val Ser Ser Asp Cys Asp Ala Val Tyr Asn Val Phe Asn
305                 310                 315                 320
Pro His Gly Tyr Ala Leu Asn Gln Ser Gly Ala Ala Asp Ser Leu
                325                 330                 335
Leu Ala Gly Thr Asp Ile Asp Cys Gly Gln Thr Leu Pro Trp His Leu
                340                 345                 350
Asn Glu Ser Phe Val Glu Gly Tyr Val Ser Arg Gly Asp Ile Glu Lys
                355                 360                 365
Ser Leu Thr Arg Leu Tyr Ser Asn Leu Val Arg Leu Gly Tyr Phe Asp
        370                 375                 380
Gly Asn Asn Ser Glu Tyr Arg Asn Leu Asn Trp Asn Asp Val Val Thr
385                 390                 395                 400
Thr Asp Ala Trp Asn Ile Ser Tyr Glu Ala Ala Val Glu Gly Ile Thr
                405                 410                 415
Leu Leu Lys Asn Asp Gly Thr Leu Pro Leu Ser Lys Lys Val Arg Ser
                420                 425                 430
Ile Ala Leu Ile Gly Pro Trp Ala Asn Ala Thr Val Gln Met Gln Gly
            435                 440                 445
Asn Tyr Tyr Gly Thr Pro Pro Tyr Leu Ile Ser Pro Leu Glu Ala Ala
450                 455                 460
Lys Ala Ser Gly Phe Thr Val Asn Tyr Ala Phe Gly Thr Asn Ile Ser
465                 470                 475                 480
Thr Asp Ser Thr Gln Trp Phe Ala Glu Ala Ile Ala Ala Ala Lys Lys
                485                 490                 495
Ser Asp Val Ile Ile Tyr Ala Gly Gly Ile Asp Asn Thr Ile Glu Ala
                500                 505                 510
Glu Gly Gln Asp Arg Thr Asp Leu Lys Trp Pro Gly Asn Gln Leu Asp
                515                 520                 525
Leu Ile Glu Gln Leu Ser Gln Val Gly Lys Pro Leu Val Val Leu Gln
            530                 535                 540
Met Gly Gly Gly Gln Val Asp Ser Ser Ser Leu Lys Ala Asn Lys Asn
545                 550                 555                 560
Val Asn Ala Leu Val Trp Gly Gly Tyr Pro Gly Gln Ser Gly Gly Ala
                565                 570                 575
Ala Leu Phe Asp Ile Leu Thr Gly Lys Arg Ala Pro Ala Gly Arg Leu
                580                 585                 590
Val Ser Thr Gln Tyr Pro Ala Glu Tyr Ala Thr Gln Phe Pro Ala Asn
            595                 600                 605
Asp Met Asn Leu Arg Pro Asn Gly Ser Asn Pro Gly Gln Thr Tyr Ile
610                 615                 620
Trp Tyr Thr Gly Thr Pro Val Tyr Glu Phe Gly His Gly Leu Phe Tyr
625                 630                 635                 640
Thr Glu Phe Gln Glu Ser Ala Ala Gly Thr Asn Lys Thr Ser Thr
                645                 650                 655
Phe Asp Ile Leu Asp Leu Phe Ser Thr Pro His Pro Gly Tyr Glu Tyr
                660                 665                 670
Ile Glu Gln Val Pro Phe Ile Asn Val Thr Val Asp Val Lys Asn Val
            675                 680                 685
Gly His Thr Pro Ser Pro Tyr Thr Gly Leu Leu Phe Ala Asn Thr Thr
            690                 695                 700
Ala Gly Pro Lys Pro Tyr Pro Asn Lys Trp Leu Val Gly Phe Asp Trp
705                 710                 715                 720
```

Leu Pro Thr Ile Gln Pro Gly Glu Thr Ala Lys Leu Thr Ile Pro Val
            725                 730                 735

Pro Leu Gly Ala Ile Ala Trp Ala Asp Glu Asn Gly Asn Lys Val Val
            740                 745                 750

Phe Pro Gly Asn Tyr Glu Leu Ala Leu Asn Asn Glu Arg Ser Val Val
            755                 760                 765

Val Ser Phe Thr Leu Thr Gly Asp Ala Ala Thr Leu Glu Lys Trp Pro
        770                 775                 780

Leu Trp Glu Gln Ala Val Pro Gly Val Leu Gln Gln
785                 790                 795

<210> SEQ ID NO 15
<211> LENGTH: 1507
<212> TYPE: DNA
<213> ORGANISM: Trichoderma reesei

<400> SEQUENCE: 15

| | | | | |
|---|---|---|---|---|
| atggcgccct | cagttacact | gccgttgacc | acggccatcc | tggccattgc | ccggctcgtc | 60 |
| gccgcccagc | aaccgggtac | cagcaccccc | gaggtccatc | ccaagttgac | aacctacaag | 120 |
| tgtacaaagt | ccgggggggtg | cgtggcccag | gacacctcgg | tggtccttga | ctggaactac | 180 |
| cgctggatgc | acgacgcaaa | ctacaactcg | tgccacgtca | acggcggcgt | caacaccacg | 240 |
| ctctgccctg | acgaggcgac | ctgtggcaag | aactgcttca | tcgagggcgt | cgactacgcc | 300 |
| gcctcgggcg | tcacgacctc | gggcagcagc | ctcaccatga | accagtacat | gccagcagc | 360 |
| tctggcggct | acagcagcgt | ctctcctcgg | ctgtatctcc | tggactctga | cggtgagtac | 420 |
| gtgatgctga | agctcaacgg | ccaggagctg | agcttcgacg | tcgacctctc | tgctctgccg | 480 |
| tgtggagaga | acggctcgct | ctacctgtct | cagatggacg | agaacggggg | cgccaaccag | 540 |
| tataacacgg | ccggtgccaa | ctacgggagc | ggctactgcg | atgctcagtg | ccccgtccag | 600 |
| acatggagga | acggcaccct | caacactagc | caccagggct | tctgctgcaa | cgagatggat | 660 |
| atcctggagg | gcaactcgag | ggcgaatgcc | ttgacccctc | actcttgcac | ggccacggcc | 720 |
| tgcgactctg | ccgttgcgg | cttcaacccc | tatggcagcg | gctacaaaag | gtgagcctga | 780 |
| tgccactact | acccctttcc | tggcgctctc | gcggttttcc | atgctgacat | ggttttccag | 840 |
| ctactacggc | cccggagata | ccgttgacac | ctccaagacc | ttcaccatca | tcacccagtt | 900 |
| caacacggac | aacggctcgc | cctcgggcaa | ccttgtgagc | atcacccgca | agtaccagca | 960 |
| aaacggcgtc | gacatcccca | gcgcccagcc | cggcggcgac | accatctcgt | cctgcccgtc | 1020 |
| cgcctcagcc | tacggcggcc | tcgccaccat | gggcaaggcc | ctgagcagcg | gcatggtgct | 1080 |
| cgtgttcagc | atttggaacg | acaacagcca | gtacatgaac | tggctcgaca | gcggcaacgc | 1140 |
| cggcccctgc | agcagcaccg | agggcaaccc | atccaacatc | ctggccaaca | accccaacac | 1200 |
| gcacgtcgtc | ttctcccaaca | tccgctgggg | agacattggg | tctactacga | actcgactgc | 1260 |
| gccccccgccc | ccgcctgcgt | ccagcacgac | gttttcgact | acacggagga | gctcgacgac | 1320 |
| ttcgagcagc | ccgagctgca | cgcagactca | ctgggggcag | tgcggtggca | ttgggtacag | 1380 |
| cgggtgcaag | acgtgcacgt | cgggcactac | gtgccagtat | agcaacgact | gttcgtatcc | 1440 |
| ccatgcctga | cgggagtgat | tttgagatgc | taaccgctaa | aatacagact | actcgcaatg | 1500 |
| cctttag | | | | | 1507 |

<210> SEQ ID NO 16
<211> LENGTH: 459

<212> TYPE: PRT
<213> ORGANISM: Trichoderma reesei

<400> SEQUENCE: 16

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
    195                 200                 205

Thr Ser His Gln Gly Phe Cys Cys Asn Glu Met Asp Ile Leu Glu Gly
210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
    275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
    355                 360                 365

Asn Ile Leu Ala Asn Asn Pro Asn Thr His Val Val Phe Ser Asn Ile
370                 375                 380

Arg Trp Gly Asp Ile Gly Ser Thr Thr Asn Ser Thr Ala Pro Pro Pro
385                 390                 395                 400
```

Pro Pro Ala Ser Ser Thr Thr Phe Ser Thr Thr Arg Arg Ser Ser Thr
            405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
    450                 455

<210> SEQ ID NO 17
<211> LENGTH: 1507
<212> TYPE: DNA
<213> ORGANISM: Trichoderma reesei

<400> SEQUENCE: 17

```
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccggggggtg cgtggcccag acacctcgg tggtccttga ctggaactac      180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gcccagcagc     360
tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct tctgctgcaa cgagatggat     660
atcctggagg caactcgag ggcgaatgcc ttgaccccctc actcttgcac ggccacggcc     720
tgcgactctg ccggttgcgg cttcaacccc tatggcagcg gctacaaaag gtgagcctga     780
tgccactact accccttccc tggcgctctc gcggttttcc atgctgacat ggttttccag     840
ctactacggc cccggagata ccgttgacac ctccaagacc ttcaccatca tcacccagtt     900
caacacggac aacggctcgc cctcgggcaa ccttgtgagc atcacccgca agtaccagca     960
aaacggcgtc gacatcccca cgcgcccagcc cggcggcgac accatctcgt cctgcccgtc    1020
cgcctcagcc tacggcggcc tcgccaccat gggcaaggcc ctgagcagcg gcatggtgct    1080
cgtgttcagc atttggaacg acaacagcca gtacatgaac tggctcgaca gcggcaacgc    1140
cggcccctgc agcagcaccg agggcaaccc atccaacatc ctggccaaca ccccaacac    1200
gcacgtcgtc ttctccaaca tccgctgggg agacattggg tctactacga actcgactgc    1260
gccccgccc ccgcctgcgt ccagcacgac gttttcgact acacggagga gctcgacgac    1320
ttcgagcagc ccgagctgca cgcagactca ctggggcag tgcggtggca ttgggtacag    1380
cgggtgcaag acgtgcacgt cgggcactac gtgccagtat agcaacgact gttcgtatcc    1440
ccatgcctga cggagtgat tttgagatgc taaccgctaa atacagact actcgcaatg    1500
cctttag                                                              1507
```

<210> SEQ ID NO 18
<211> LENGTH: 418
<212> TYPE: PRT
<213> ORGANISM: Trichoderma reesei

```
<400> SEQUENCE: 18

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
            115                 120                 125

Asn Asn Tyr Pro Asp Gly Ile Gly Gln Met Gln His Phe Val Asn Asp
        130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415
```

Arg Lys

<210> SEQ ID NO 19
<211> LENGTH: 1545
<212> TYPE: DNA
<213> ORGANISM: Trichoderma reesei

<400> SEQUENCE: 19

```
atgtatcgga agttggccgt catctcggcc ttcttggcca cagctcgtgc tcagtcggcc        60
tgcactctcc aatcggagac tcacccgcct ctgacatggc agaaatgctc gtctggtggc       120
acgtgcactc aacagacagg ctccgtggtc atcgacgcca actggcgctg gactcacgct       180
acgaacagca gcacgaactg ctacgatggc aacacttgga gctcgaccct atgtcctgac       240
aacgagacct cgcgcaagaa ctgctgtctg acggtgccg cctacgcgtc cacgtacgga        300
gttaccacga gcggtaacag cctctccatt ggctttgtca cccagtctgc gcagaagaac       360
gttggcgctc gcctttacct tatggcgagc gacacgacct accaggaatt caccctgctt       420
ggcaacgagt tctctttcga tgttgatgtt tcgcagctgc cgtgcggctt gaacggagct       480
ctctacttcg tgtccatgga cgcggatggt ggcgtgagca agtatcccac caacaccgct       540
ggcgccaagt acggcacggg gtactgtgac agccagtgtc ccgcgatct gaagttcatc        600
aatggccagg ccaacgttga gggctgggag ccgtcatcca caacgcgaa cacgggcatt        660
ggaggacacg gaagctgctg ctctgagatg gatatctggg aggccaactc catctccgag       720
gctcttaccc cccacccttg cacgactgtc ggccaggaga tctgcgaggg tgatgggtgc       780
ggcggaactt actccgataa cagatatggc ggcacttgcg atcccgatgg ctgcgactgg       840
aacccatacc gcctgggcaa caccagcttc tacggccctg gctcaagctt taccctcgat       900
accaccaaga aattgaccgt tgtcacccag ttcgagacgt cgggtgccat caaccgatac       960
tatgtccaga atggcgtcac tttccagcag cccaacgccg agcttggtag ttactctggc      1020
aacgagctca acgatgatta ctgcacagct gaggaggcag aattcggcgg atcctctttc      1080
tcagacaagg gcggcctgac tcagttcaag aaggctacct ctggcggcat ggttctggtc      1140
atgagtctgt gggatgatta ctacgccaac atgctgtggc tggactccac ctacccgaca      1200
aacgagacct cctccacacc cggtgccgtg cgcggaagct gctccaccag ctccggtgtc      1260
cctgctcagg tcgaatctca gtctcccaac gccaaggtca ccttctccaa catcaagttc      1320
ggacccattg gcagcaccgg caaccctagc ggcggcaacc ctcccggcgg aaacccgcct      1380
ggcaccacca ccacccgccg cccagccact accactggaa gctctcccgg acctacccag      1440
tctcactacg gccagtgcgg cggtattggc tacagcggcc ccacggtctg cgccagcggc      1500
acaacttgcc aggtcctgaa cccttactac tctcagtgcc tgtaa                      1545
```

<210> SEQ ID NO 20
<211> LENGTH: 514
<212> TYPE: PRT
<213> ORGANISM: Trichoderma reesei

<400> SEQUENCE: 20

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

```
Val Val Ile Asp Ala Asn Trp Arg Trp Thr His Ala Thr Asn Ser Ser
    50              55              60
Thr Asn Cys Tyr Asp Gly Asn Thr Trp Ser Ser Thr Leu Cys Pro Asp
65              70              75              80
Asn Glu Thr Cys Ala Lys Asn Cys Cys Leu Asp Gly Ala Ala Tyr Ala
                85              90              95
Ser Thr Tyr Gly Val Thr Thr Ser Gly Asn Ser Leu Ser Ile Gly Phe
            100             105             110
Val Thr Gln Ser Ala Gln Lys Asn Val Gly Ala Arg Leu Tyr Leu Met
        115             120             125
Ala Ser Asp Thr Thr Tyr Gln Glu Phe Thr Leu Leu Gly Asn Glu Phe
    130             135             140
Ser Phe Asp Val Asp Val Ser Gln Leu Pro Cys Gly Leu Asn Gly Ala
145             150             155             160
Leu Tyr Phe Val Ser Met Asp Ala Asp Gly Gly Val Ser Lys Tyr Pro
                165             170             175
Thr Asn Thr Ala Gly Ala Lys Tyr Gly Thr Gly Tyr Cys Asp Ser Gln
            180             185             190
Cys Pro Arg Asp Leu Lys Phe Ile Asn Gly Gln Ala Asn Val Glu Gly
        195             200             205
Trp Glu Pro Ser Ser Asn Asn Ala Asn Thr Gly Ile Gly Gly His Gly
    210             215             220
Ser Cys Cys Ser Glu Met Asp Ile Trp Glu Ala Asn Ser Ile Ser Glu
225             230             235             240
Ala Leu Thr Pro His Pro Cys Thr Thr Val Gly Gln Glu Ile Cys Glu
                245             250             255
Gly Asp Gly Cys Gly Gly Thr Tyr Ser Asp Asn Arg Tyr Gly Gly Thr
            260             265             270
Cys Asp Pro Asp Gly Cys Asp Trp Asn Pro Tyr Arg Leu Gly Asn Thr
        275             280             285
Ser Phe Tyr Gly Pro Gly Ser Ser Phe Thr Leu Asp Thr Thr Lys Lys
    290             295             300
Leu Thr Val Val Thr Gln Phe Glu Thr Ser Gly Ala Ile Asn Arg Tyr
305             310             315             320
Tyr Val Gln Asn Gly Val Thr Phe Gln Gln Pro Asn Ala Glu Leu Gly
                325             330             335
Ser Tyr Ser Gly Asn Glu Leu Asn Asp Asp Tyr Cys Thr Ala Glu Glu
            340             345             350
Ala Glu Phe Gly Gly Ser Ser Phe Ser Asp Lys Gly Gly Leu Thr Gln
        355             360             365
Phe Lys Lys Ala Thr Ser Gly Gly Met Val Leu Val Met Ser Leu Trp
    370             375             380
Asp Asp Tyr Tyr Ala Asn Met Leu Trp Leu Asp Ser Thr Tyr Pro Thr
385             390             395             400
Asn Glu Thr Ser Ser Thr Pro Gly Ala Val Arg Gly Ser Cys Ser Thr
                405             410             415
Ser Ser Gly Val Pro Ala Gln Val Glu Ser Gln Ser Pro Asn Ala Lys
            420             425             430
Val Thr Phe Ser Asn Ile Lys Phe Gly Pro Ile Gly Ser Thr Gly Asn
        435             440             445
Pro Ser Gly Gly Asn Pro Pro Gly Gly Asn Pro Pro Gly Thr Thr Thr
    450             455             460
```

-continued

```
Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu
```

<210> SEQ ID NO 21
<211> LENGTH: 1611
<212> TYPE: DNA
<213> ORGANISM: Trichoderma reesei

<400> SEQUENCE: 21

| | | | | |
|---|---|---|---|---|
| atgattgtcg | gcattctcac | cacgctggct | acgctggcca | cactcgcagc tagtgtgcct | 60 |
| ctagaggagc | ggcaagcttg | ctcaagcgtc | tggtaattat | gtgaaccctc tcaagagacc | 120 |
| caaatactga | gatatgtcaa | ggggccaatg | tggtggccag | aattggtcgg gtccgacttg | 180 |
| ctgtgcttcc | ggaagcacat | gcgtctactc | caacgactat | tactcccagt gtcttcccgg | 240 |
| cgctgcaagc | tcaagctcgt | ccacgcgcgc | gcgtcgacg | acttctcgag tatcccccac | 300 |
| aacatcccgg | tcgagctccg | cgacgcctcc | acctggttct | actactacca gagtacctcc | 360 |
| agtcggatcg | ggaaccgcta | cgtattcagg | caacccttt | gttggggtca ctccttgggc | 420 |
| caatgcatat | tacgcctctg | aagttagcag | cctcgctatt | cctagcttga ctggagccat | 480 |
| ggccactgct | gcagcagctg | tcgcaaaggt | tccctctttt | atgtggctgt aggtcctccc | 540 |
| ggaaccaagg | caatctgtta | ctgaaggctc | atcattcact | gcagagatac tcttgacaag | 600 |
| accccctctca | tggagcaaac | cttggccgac | atccgcaccg | ccaacaagaa tggcggtaac | 660 |
| tatgccggac | agtttgtggt | gtatgacttg | ccggatcgcg | attgcgctgc ccttgcctcg | 720 |
| aatggcgaat | actctattgc | cgatggtggc | gtcgccaaat | ataagaacta tatcgacacc | 780 |
| attcgtcaaa | ttgtcgtgga | atattccgat | atccggaccc | tcctggttat tggtatgagt | 840 |
| ttaaacacct | gcctcccccc | cccctttccct | tcctttcccg | ccggcatctt gtcgttgtgc | 900 |
| taactattgt | tccctcttcc | agagcctgac | tctcttgcca | acctggtgac caacctcggt | 960 |
| actccaaagt | gtgccaatgc | tcagtcagcc | taccttgagt | gcatcaacta cgccgtcaca | 1020 |
| cagctgaacc | ttccaaatgt | tgcgatgtat | ttggacgctg | ccatgcagg atggcttggc | 1080 |
| tggccggcaa | accaagaccc | ggccgctcag | ctatttgcaa | atgtttacaa gaatgcatcg | 1140 |
| tctccgagag | ctcttcgcgg | attggcaacc | aatgtcgcca | actacaacgg gtggaacatt | 1200 |
| accagccccc | catcgtacac | gcaaggcaac | gctgtctaca | cgagaagct gtacatccac | 1260 |
| gctattggac | gtcttcttgc | caatcacggc | tggtccaacg | ccttcttcat cactgatcaa | 1320 |
| ggtcgatcgg | gaaagcagcc | taccggacag | caacagtggg | gagactggtg caatgtgatc | 1380 |
| ggcaccggat | ttggtattcg | cccatccgca | aacactgggg | actcgttgct ggattcgttt | 1440 |
| gtctgggtca | agccaggcgg | cgagtgtgac | ggcaccagcg | acagcagtgc gccacgattt | 1500 |
| gactcccact | gtgcgctccc | agatgccttg | caaccggcgc | ctcaagctgg tgcttggttc | 1560 |
| caagcctact | ttgtgcagct | tctcacaaac | gcaaacccat | cgttcctgta a | 1611 |

<210> SEQ ID NO 22
<211> LENGTH: 471
<212> TYPE: PRT
<213> ORGANISM: Trichoderma reesei

<400> SEQUENCE: 22

```
Met Ile Val Gly Ile Leu Thr Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415
```

Trp Val Lys Pro Gly Gly Glu Cys Asp Gly Thr Ser Asp Ser Ser Ala
              420                 425                 430

Pro Arg Phe Asp Ser His Cys Ala Leu Pro Asp Ala Leu Gln Pro Ala
          435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 23
<211> LENGTH: 2615
<212> TYPE: DNA
<213> ORGANISM: Trichoderma reesei

<400> SEQUENCE: 23

```
atgggatttg gccgcaatgc tgccgagccc gagtgtttct gcaacgttat ccaggagatt     60
tgcgcttgcc caagagggag ttgacgggga gagtcccaac tggttccttc agtaacgcca    120
ccctggcaga ctatataact tgtggacaag actctgcttt gttgagttct tcctaccagt    180
cttgaccaag accattctgt tgagcccaat cagaaatgcg ttaccgaaca gcagctgcgc    240
tggcacttgc cactgggccc tttgctaggg cagacagtca gtatagctgg tccatactgg    300
gatgtatatg tatcctggag acaccatgct gactcttgaa tcaaggtagc tcaacatcgg    360
gggcctcggc tgaggcagtt gtacctcctg cagggactcc atggggaacc gcgtacgaca    420
aggcgaaggc cgcattggca aagctcaatc tccaagataa ggtcggcatc gtgagcggtg    480
tcggctggaa cggcggtcct tgcgttggaa acacatctcc ggcctccaag atcagctatc    540
catcgctatg ccttcaagac ggaccgctcg gtgttcgata ctcgacaggc agcacagcct    600
ttacgccggg cgttcaagcg gcctcgacgt gggatgtcaa tttgatccgc gaacgtggac    660
agttcatcgg tgaggaggtg aaggcctcgg ggattcatgt catacttggt cctgtggctg    720
ggccgctggg aaagactccg cagggcggtc gcaactggga gggcttcggt gtcgatccat    780
atctcacggg cattgccatg ggtcaaacca tcaacggcat ccagtcggta ggcgtgcagg    840
cgacagcgaa gcactatatc ctcaacgagc aggagctcaa tcgagaaacc atttcgagca    900
acccagatga ccgaactctc catgagctgt atacttggcc atttgccgac gcggttcagg    960
ccaatgtcgc ttctgtcatg tgctcgtaca caaggtcaa taccacctgg gcctgcgagg   1020
atcagtacac gctgcagact gtgctgaaag accagctggg gttcccaggc tatgtcatga   1080
cggactggaa cgcacagcac acgactgtcc aaagcgcgaa ttctgggctt gacatgtcaa   1140
tgcctggcac agacttcaac ggtaacaatc ggctctgggg tccagctctc accaatgcgg   1200
taaatagcaa tcaggtcccc acgagcagag tcgacgatat ggtgactcgt atcctcgccg   1260
catggtactt gacaggccag gaccaggcag ctatccgtc gttcaacatc agcagaaatg   1320
ttcaaggaaa ccacaagacc aatgtcaggg caattgccag gacggcatc gttctgctca   1380
agaatgacgc caacatcctg ccgctcaaga agcccgctag cattgccgtc gttggatctg   1440
ccgcaatcat tggtaaccac gccagaaact cgccctcgtg caacgacaaa ggctgcgacg   1500
acggggcctt gggcatgggt tggggttccg gcgccgtcaa ctatccgtac ttcgtcgcgc   1560
cctacgatgc catcaatacc agagcgtctt cgcagggcac ccaggttacc ttgagcaaca   1620
ccgacaacac gtcctcaggc gcatctgcag caagaggaaa ggacgtcgcc atcgtcttca   1680
tcaccgccga ctcgggtgaa ggctacatca ccgtggaggg caacgcgggc gatcgcaaca   1740
```

-continued

```
acctggatcc gtggcacaac ggcaatgccc tggtccaggc ggtggccggt gccaacagca    1800
acgtcattgt tgttgtccac tccgttggcg ccatcattct ggagcagatt cttgctcttc    1860
cgcaggtcaa ggccgttgtc tgggcgggtc ttccttctca ggagagcggc aatgcgctcg    1920
tcgacgtgct gtggggagat gtcagcccct ctggcaagct ggtgtacacc attgcgaaga    1980
gccccaatga ctataacact cgcatcgttt ccggcggcag tgacagcttc agcgagggac    2040
tgttcatcga ctataagcac ttcgacgacg ccaatatcac gccgcggtac gagttcggct    2100
atggactgtg taagtttgct aacctgaaca atctattaga caggttgact gacggatgac    2160
tgtggaatga tagcttacac caagttcaac tactcacgcc tctccgtctt gtcgaccgcc    2220
aagtctggtc ctgcgactgg ggccgttgtg ccgggaggcc cgagtgatct gttccagaat    2280
gtcgcgacag tcaccgttga catcgcaaac tctggccaag tgactggtgc cgaggtagcc    2340
cagctgtaca tcacctaccc atcttcagca cccaggaccc ctccgaagca gctgcgaggc    2400
tttgccaagc tgaacctcac gcctggtcag agcggaacag caacgttcaa catccgacga    2460
cgagatctca gctactggga cacggcttcg cagaaatggg tggtgccgtc ggggtcgttt    2520
ggcatcagcg tgggagcgag cagccgggat atcaggctga cgagcactct gtcggtagcg    2580
tagcgcgagg agggtgaagg cggttgacct gtgac                               2615
```

<210> SEQ ID NO 24
<211> LENGTH: 744
<212> TYPE: PRT
<213> ORGANISM: Trichoderma reesei

<400> SEQUENCE: 24

```
Met Arg Tyr Arg Thr Ala Ala Leu Ala Leu Ala Thr Gly Pro Phe
  1               5                  10                 15

Ala Arg Ala Asp Ser His Ser Thr Ser Gly Ala Ser Ala Glu Ala Val
                 20                  25                  30

Val Pro Pro Ala Gly Thr Pro Trp Gly Thr Ala Tyr Asp Lys Ala Lys
             35                  40                  45

Ala Ala Leu Ala Lys Leu Asn Leu Gln Asp Lys Val Gly Ile Val Ser
         50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                 85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220
```

```
Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
            245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
        290                 295                 300

Ala Val Asn Ser Asn Gln Val Pro Thr Ser Arg Val Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
            405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
            450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
            530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640
```

Leu Phe Gln Asn Val Ala Thr Val Thr Val Asp Ile Ala Asn Ser Gly
            645                 650                 655

Gln Val Thr Gly Ala Glu Val Ala Gln Leu Tyr Ile Thr Tyr Pro Ser
        660                 665                 670

Ser Ala Pro Arg Thr Pro Lys Gln Leu Arg Gly Phe Ala Lys Leu
    675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 25
<211> LENGTH: 752
<212> TYPE: DNA
<213> ORGANISM: Trichoderma reesei

<400> SEQUENCE: 25

```
atggttgcct tttccagcct catctgcgct ctcaccagca tcgccagtac tctggcgatg      60
cccacaggcc tcgagcctga gagcagtgtc aacgtcacag agcgtggcat gtacgacttt     120
gttcttggag ctcacaatga tcatcgccgt cgtgctagca tcaactacga ccaaaactac     180
caaactggcg gacaagtcag ctattcgcct tccaacactg gcttctcagt gaactggaac     240
actcaagatg actttgttgt gggcgttggt tggacgactg gatcttctgc gtaggaggac     300
tcctcatcat tctgcacttt gaaagcatct tctgaccaaa agcttctctt agtcccatca     360
actttggcgg ctctttttagt gtcaacagcg gaactggcct gctttccgtc tatggctgga     420
gcaccaaccc actggttgag tactacatca tggaggacaa ccacaactac ccagcacagg     480
gtaccgtcaa gggaaccgtc accagcgacg gagccactta ccatcctggg agaatacccc     540
gtgtcaacga gccttccatc cagggcacag cgaccttcaa ccagtacatt tccgtgcgga     600
actcgcccag gaccagcgga actgttactg tgcagaacca cttcaatgct tgggcctcgc     660
ttggcctgca ccttgggcag atgaactacc aggttgtcgc tgtcgaaggc tggggtggta     720
gtggttctgc ctcacagagt gtcagcaact ag                                    752
```

<210> SEQ ID NO 26
<211> LENGTH: 229
<212> TYPE: PRT
<213> ORGANISM: Trichoderma reesei

<400> SEQUENCE: 26

Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser

```
                         85                  90                  95
Ala Pro Ile Asn Phe Gly Gly Ser Phe Ser Val Asn Ser Gly Thr Gly
                100                 105                 110

Leu Leu Ser Val Tyr Gly Trp Ser Thr Asn Pro Leu Val Glu Tyr Tyr
            115                 120                 125

Ile Met Glu Asp Asn His Asn Tyr Pro Ala Gln Gly Thr Val Lys Gly
        130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225

<210> SEQ ID NO 27
<211> LENGTH: 796
<212> TYPE: DNA
<213> ORGANISM: Trichoderma reesei

<400> SEQUENCE: 27
caagaagaca tcaacatggt ctccttcacc tccctcctcg ccggcgtcgc cgccatctcg      60
ggcgtcttgg ccgctcccgc cgccgaggtc gaatccgtgg ctgtggagaa gcgccagacg     120
attcagcccg gcacgggcta caacaacggc tacttctact cgtactggaa cgatggccac     180
ggcggcgtga cgtacaccaa tggtcccggc gggcagttct ccgtcaactg gtccaactcg     240
ggcaactttg tcggcggcaa gggatggcag cccggcacca gaacaagta agactaccta     300 ctcttacccc ctttgaccaa cacagcacaa cacaatacaa cacatgtgac taccaatcat     360
ggaatcggat ctaacagctg tgttttcaaa aaaagggtc atcaacttct cgggcagcta     420
caaccccaac ggcaacagct acctctccgt gtacggctgg tcccgcaacc ccctgatcga     480
gtactacatc gtcgagaact ttggcaccta caacccgtcc acgggcgcca ccaagctggg     540
cgaggtcacc tccgacggca gcgtctacga catttaccgc acgcagcgcg tcaaccagcc     600
gtccatcatc ggcaccgcca ccttttacca gtactggtcc gtccgccgca accaccgctc     660
gagcggctcc gtcaacacgg cgaaccactt caacgcgtgg gctcagcaag gcctgacgct     720
cgggacgatg gattaccaga ttgttgccgt ggagggttac tttagctctg gctctgcttc     780
catcaccgtc agctaa                                                      796

<210> SEQ ID NO 28
<211> LENGTH: 223
<212> TYPE: PRT
<213> ORGANISM: Trichoderma reesei

<400> SEQUENCE: 28

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30
```

Arg Gln Thr Ile Gln Pro Gly Thr Gly Tyr Asn Asn Gly Tyr Phe Tyr
                35                  40                  45

Ser Tyr Trp Asn Asp Gly His Gly Gly Val Tyr Thr Asn Gly Pro
 50                  55                  60

Gly Gly Gln Phe Ser Val Asn Trp Ser Asn Ser Gly Asn Phe Val Gly
 65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
                100                 105                 110

Ser Arg Asn Pro Leu Ile Glu Tyr Tyr Ile Val Glu Asn Phe Gly Thr
                115                 120                 125

Tyr Asn Pro Ser Thr Gly Ala Thr Lys Leu Gly Glu Val Thr Ser Asp
                130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
                180                 185                 190

Ala Gln Gln Gly Leu Thr Leu Gly Thr Met Asp Tyr Gln Ile Val Ala
                195                 200                 205

Val Glu Gly Tyr Phe Ser Ser Gly Ser Ala Ser Ile Thr Val Ser
                210                 215                 220

<210> SEQ ID NO 29
<211> LENGTH: 1352
<212> TYPE: DNA
<213> ORGANISM: Trichoderma reesei

<400> SEQUENCE: 29
atgaaagcaa acgtcatctt gtgcctcctg gccccctgg tcgccgctct ccccaccgaa      60
accatccacc tcgaccccga gctcgccgct ctccgcgcca acctcaccga gcgaacagcc    120
gacctctggg accgccaagc tctcaaagc atcgaccagc tcatcaagag aaaaggcaag     180
ctctactttg gcaccgccac cgaccgcggc ctcctccaac gggaaaagaa cgcggccatc    240
atccaggcag acctcggcca ggtgacgccg agaacagca tgaagtggca gtcgctcgag     300
aacaaccaag gccagctgaa ctggggagac gccgactatc tcgtcaactt tgcccagcaa    360
aacggcaagt cgatacgcgg ccacactctg atctggcact cgcagctgcc tcgtgggtg    420 aacaatatca caacgcgga tactctgcgg caagtcatcc gcacccatgt ctctactgtg    480
gttgggcggt acaagggcaa gattcgtgct tgggtgagtt ttgaacacca catgcccctt    540
ttcttagtcc gctcctcctc ctcttggaac ttctcacagt tatagccgta caacattc     600 gacaggaaat ttaggatgac aactactgac tgacttgtgt gtgtgatggc gataggacgt    660
ggtcaatgaa atcttcaacg aggatggaac gctgcgctct tcagtctttt ccaggctcct    720
cggcgaggag tttgtctcga ttgccttttcg tgctgctcga gatgctgacc cttctgcccg   780
tctttacatc aacgactaca atctcgaccg cgccaactat ggcaaggtca cgggttgaa    840 gacttacgtc tccaagtgga tctctcaagg agttcccatt gacggtattg gtgagccacg    900 accctaaat gtccccatt agagtctctt tctagagcca aggcttgaag ccattcaggg     960
actgacacga gagcctctct tacaggaagc cagtcccatc tcagcggcgg cggaggctct   1020
ggtacgctgg gtgcgctcca gcagctggca acggtacccg tcaccgagct ggccattacc   1080

```
gagctggaca ttcaggggggc accgacgacg gattacaccc aagttgttca agcatgcctg   1140
agcgtctcca agtgcgtcgg catcaccgtg tggggcatca gtgacaaggt aagttgcttc   1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                 1352
```

<210> SEQ ID NO 30
<211> LENGTH: 347
<212> TYPE: PRT
<213> ORGANISM: Trichoderma reesei

<400> SEQUENCE: 30

```
Met Lys Ala Asn Val Ile Leu Cys Leu Leu Ala Pro Leu Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Gln Ala Cys Leu Ser Val Ser
    290                 295                 300

Lys Cys Val Gly Ile Thr Val Trp Gly Ile Ser Asp Lys Asp Ser Trp
305                 310                 315                 320
```

Arg Ala Ser Thr Asn Pro Leu Leu Phe Asp Ala Asn Phe Asn Pro Lys
            325                 330                 335

Pro Ala Tyr Asn Ser Ile Val Gly Ile Leu Gln
            340                 345

<210> SEQ ID NO 31
<211> LENGTH: 2564
<212> TYPE: DNA
<213> ORGANISM: Trichoderma reesei

<400> SEQUENCE: 31

| | | | | |
|---|---|---|---|---|
| ggacagccgg | acgcaatggt | gaataacgca | gctcttctcg | ccgccctgtc | ggctctcctg | 60 |
| cccacggccc | tggcgcagaa | caatcaaaca | tacgccaact | actctgctca | gggccagcct | 120 |
| gatctctacc | ccgagacact | tgccacgctc | acactctcgt | tccccgactg | cgaacatggc | 180 |
| cccctcaaga | acaatctcgt | ctgtgactca | tcggccggct | atgtagagcg | agcccaggcc | 240 |
| ctcatctcgc | tcttcaccct | cgaggagctc | attctcaaca | cgcaaaactc | gggccccggc | 300 |
| gtgcctcgcc | tgggtcttcc | gaactaccaa | gtctggaatg | aggctctgca | cggcttggac | 360 |
| cgcgccaact | tcgccaccaa | gggcggccag | ttcgaatggg | cgacctcgtt | ccccatgccc | 420 |
| atcctcacta | cggcggccct | caaccgcaca | ttgatccacc | agattgccga | catcatctcg | 480 |
| acccaagctc | gagcattcag | caacagcggc | cgttacggtc | tcgacgtcta | tgcgccaaac | 540 |
| gtcaatggct | tccgaagccc | cctctggggc | cgtggccagg | agacgcccgg | cgaagacgcc | 600 |
| tttttcctca | gctccgccta | tacttacgag | tacatcacgg | gcatccaggg | tggcgtcgac | 660 |
| cctgagcacc | tcaaggttgc | cgccacggtg | aagcactttg | ccggatacga | cctcgagaac | 720 |
| tggaacaacc | agtcccgtct | cggtttcgac | gccatcataa | ctcagcagga | cctctccgaa | 780 |
| tactacactc | cccagttcct | cgctgcggcc | cgttatgcaa | agtcacgcag | cttgatgtgc | 840 |
| gcatacaact | ccgtcaacgg | cgtgcccagc | tgtgccaaca | gcttcttcct | gcagacgctt | 900 |
| ttgcgcgaga | gctggggctt | ccccgaatgg | ggatacgtct | cgtccgattg | cgatgccgtc | 960 |
| tacaacgttt | tcaaccctca | tgactacgcc | agcaaccagt | cgtcagccgc | cgccagctca | 1020 |
| ctgcgagccg | gcaccgatat | cgactgcggt | cagacttacc | cgtggcacct | caacgagtcc | 1080 |
| tttgtggccg | gcgaagtctc | ccgcggcgag | atcgagcggt | ccgtcacccg | tctgtacgcc | 1140 |
| aacctcgtcc | gtctcggata | cttcgacaag | aagaaccagt | accgctcgct | cggttggaag | 1200 |
| gatgtcgtca | agactgatgc | ctggaacatc | tcgtacgagg | ctgctgttga | gggcatcgtc | 1260 |
| ctgctcaaga | acgatggcac | tctccctctg | tccaagaagg | tgcgcagcat | tgctctgatc | 1320 |
| ggaccatggg | ccaatgccac | aacccaaatg | caaggcaact | actatggccc | tgccccatac | 1380 |
| ctcatcagcc | ctctggaagc | tgctaagaag | gccggctatc | acgtcaactt | tgaactcggc | 1440 |
| acagagatcg | ccggcaacag | caccactggc | tttgccaagg | ccattgctgc | cgccaagaag | 1500 |
| tcggatgcca | tcatctacct | cggtggaatt | gacaacacca | ttgaacagga | gggcgctgac | 1560 |
| cgcacggaca | ttgcttggcc | cggtaatcag | ctggatctca | tcaagcagct | cagcgaggtc | 1620 |
| ggcaaacccc | ttgtcgtcct | gcaaatgggc | ggtggtcagg | tagactcatc | ctcgctcaag | 1680 |
| agcaacaaga | aggtcaactc | cctcgtctgg | ggcggatatc | ccggccagtc | gggaggcgtt | 1740 |
| gccctcttcg | acattctctc | tggcaagcgt | gctcctgccg | gccgactggt | caccactcag | 1800 |
| tacccggctg | agtatgttca | ccaattcccc | cagaatgaca | tgaacctccg | acccgatgga | 1860 |
| aagtcaaacc | ctggacagac | ttacatctgg | tacaccggca | aacccgtcta | cgagtttggc | 1920 |
| agtggtctct | tctacaccac | cttcaaggag | actctcgcca | gccaccccaa | gagcctcaag | 1980 |

```
ttcaacacct catcgatcct ctctgctcct cacccccggat acacttacag cgagcagatt    2040
cccgtcttca ccttcgaggc caacatcaag aactcgggca agacggagtc cccatatacg    2100
gccatgctgt ttgttcgcac aagcaacgct ggcccagccc cgtacccgaa caagtggctc    2160
gtcggattcg accgacttgc cgacatcaag cctggtcact cttccaagct cagcatcccc    2220
atccctgtca gtgctctcgc ccgtgttgat tctcacggaa accggattgt ataccccggc    2280
aagtatgagc tagccttgaa caccgacgag tctgtgaagc ttgagtttga gttggtggga    2340
gaagaggtaa cgattgagaa ctggccgttg gaggagcaac agatcaagga tgctacacct    2400
gacgcataag ggttttaatg atgttgttat gacaaacggg tagagtagtt aatgatggaa    2460
taggaagagg ccatagtttt ctgtttgcaa accattttttg ccattgcgaa aaaaaaaaa    2520 aaaaaaaaaa aaaaaaaaaa aaaaaaaaaa aaaaaaaaaa aaaa                     2564
```

<210> SEQ ID NO 32
<211> LENGTH: 780
<212> TYPE: PRT
<213> ORGANISM: Trichoderma reesei

<400> SEQUENCE: 32

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270
```

```
Leu Met Cys Ala Tyr Asn Ser Val Asn Gly Val Pro Ser Cys Ala Asn
            275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ala Ala Ser Ser Leu
                325                 330                 335

Arg Ala Gly Thr Asp Ile Asp Cys Gly Gln Thr Tyr Pro Trp His Leu
                340                 345                 350

Asn Glu Ser Phe Val Ala Gly Glu Val Ser Arg Gly Glu Ile Glu Arg
            355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
            435                 440                 445

Tyr Tyr Gly Pro Ala Pro Tyr Leu Ile Ser Pro Leu Glu Ala Ala Lys
            450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
                485                 490                 495

Asp Ala Ile Ile Tyr Leu Gly Gly Ile Asp Asn Thr Ile Glu Gln Glu
                500                 505                 510

Gly Ala Asp Arg Thr Asp Ile Ala Trp Pro Gly Asn Gln Leu Asp Leu
            515                 520                 525

Ile Lys Gln Leu Ser Glu Val Gly Lys Pro Leu Val Val Leu Gln Met
            530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
                580                 585                 590

Thr Thr Gln Tyr Pro Ala Glu Tyr Val His Gln Phe Pro Gln Asn Asp
            595                 600                 605

Met Asn Leu Arg Pro Asp Gly Lys Ser Asn Pro Gly Gln Thr Tyr Ile
            610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
                660                 665                 670

Glu Gln Ile Pro Val Phe Thr Phe Glu Ala Asn Ile Lys Asn Ser Gly
                675                 680                 685
```

```
Lys Thr Glu Ser Pro Tyr Thr Ala Met Leu Phe Val Arg Thr Ser Asn
    690                 695                 700
Ala Gly Pro Ala Pro Tyr Pro Asn Lys Trp Leu Val Gly Phe Asp Arg
705                 710                 715                 720
Leu Ala Asp Ile Lys Pro Gly His Ser Ser Lys Leu Ser Ile Pro Ile
                725                 730                 735
Pro Val Ser Ala Leu Ala Arg Val Asp Ser His Gly Asn Arg Ile Val
            740                 745                 750
Tyr Pro Gly Lys Tyr Glu Leu Ala Leu Asn Thr Asp Glu Ser Val Lys
        755                 760                 765
Leu Glu Phe Glu Leu Val Gly Glu Glu Val Thr Ile
    770                 775                 780

<210> SEQ ID NO 33
<211> LENGTH: 2502
<212> TYPE: DNA
<213> ORGANISM: Thermoascus aurantiacus

<400> SEQUENCE: 33
atgcgcgcaa ttggacttct gccaggcatc atcggcattg ctggtgctgc ctgtccttac      60
atgacaggcg agctgccgcg ctccttcgcc gagaaccctc atgctatcaa ccgtcgtgct     120
gagggtggtg gtggtgccgc tgccgagacg agaagttcc  tgtctcagtt ctacctgaac     180
gacaacgaca ccttcatgac caccgatgtt ggcggtccaa ttgaggatca gaacagtctc     240
agcgctggtg acagaggtcc taccctgctg gaggacttca tcctccgtca aaagatccag     300
cgctttgacc atgagcgggt aggttgatct ttactttcgg ccttcttcga gcggggtgat     360
attaaaacag gtaataggtg cccgagcgtg ctgtccatgc ccgaggagcg ggagcgcatg     420
gcgtgttcac atcctacgca gactggtcca acatcactgc cgcttccttc ctgtctgctg     480
caggaaagga gacacctgtc tttgtccggt tctccactgt agcaggaagc agaggaagcg     540
cagacacggc gcgtgacgtg cacggtttcg cgacgaggtt ctacacggat gaagggaact     600
tcggtaggca actatcatgc tctctttaaa tgttctcgat ctgacagcca gcagacattg     660
tcggcaacaa catccctgtc ttcttcattc aagatgcgat ccagttcccc gacctgatcc     720
atgctgtcaa gcccagcccg aacaacgaga tccctcaggc cgcaaccgcc catgactctg     780
cctgggactt tttcagccag cagccgagct ctttgcatac tctgttctgg gctatggccg     840
gtcatggcat tcctcgttcc tacaggaaca tggatggctt cggcatccac accttccgct     900 tgtgacgga  cgatggagct tccaagctcg tcaagttcca ctggacgtcg ctgcagggca     960
aggcgagcct tgtgtgggaa gaggcacagg ccgtggctgg aaagaacgcg gactatcacc    1020
gccaggactt gtgggacgca atcgaggctg gaaggtaccc tgagtgggag gtaggctctc    1080
cctgctatgt atggatgtgc cagaagctta ataatggcct agctcggcgt gcaaatcatg    1140
gatgaggaag accagctgcg ctttggcttc gatctgttgg acccgaccaa gatcgttccc    1200
gaggaatacg tgcccatcac gaagctcgga aagatgcagc tcaaccgcaa cccgctgaac    1260
tacttcgccg agactgaaca gatcatggtc agttcgccac cgtgttcggt tgctcgttgc    1320
tgaagtgcta acttgcaaca gttccaaccg ggtcacgttg tccgtggcat tgatttcacc    1380
gaggaccctc tgctccaggg acgtctcttc tcttacctcg acacccagct caaccgccac    1440
ggaggtccga acttcgagca gatccccatc aaccggccac gcactccaat tcacaacaac    1500
aaccgtgacg gagccggtat gctagcccat gtattccttt ctttatgcat ttttatatga    1560
tgcgttctaa cggcaacagc gcaaatgtac atccccctga acaaggcggc gtacacccc     1620
```

```
aacactctga caacggctc ccccaagcag gccaaccaga cggtcggaaa gggcttcttc   1680
acgactccag gccggacggc aagcggcagg cttgtgcgcg ccgtcagctc aaccttcgcc   1740
gacgtctggt cgcagcctcg tctgttctac aactccctcg tgccggcgga gcagcagttc   1800
ctgatcaacg cgatccgctt tgagacggcc cacatcacga gcgacgtcgt gaagaacaac   1860
gtcatcatcc agctgaaccg cgtgagcaac aacctcgcca agagagtcgc ccgggccatc   1920
ggtgtcgcgg agcccgagcc agacccaacc ttgtaccaca caacaagac cgccaacgtc    1980
ggggtgttcg gcaagccgct cgccagactc gacggcctgc aggtcggggt cctcgccacc   2040
gtcaacaagc ccgactcgat caagcaggcc gccagcctga aggccagctt cgcggcggac   2100
aacgtcgacg tcaaggtcgt cgcggagcgc ctcgccgacg cgtcgacga gacctactcg    2160
gccgccgacg cggtcaactt cgacgccatc ctggtcgcca acggcgctga gggcctcttc   2220
gcgcgcgaca gcttcaccgc caggccggcc aactcgacca ccgcgacgct ctaccccgcg   2280
ggccgcccgc tccagatcct ggtcgacggg ttccgctacg caagccggt cggggcgctc    2340
ggcagcggcg ccaaggcgct cgacgcagcg gagatttcga cgacccgggc cggcgtgtac   2400
gtcgccaact cgacgaccga cagcttcatc aatggcgtca gggacggtct gcggacgttc   2460
aagttcctgg accggttcgc gattgacgag gatgctgagt ga                      2502
```

<210> SEQ ID NO 34
<211> LENGTH: 740
<212> TYPE: PRT
<213> ORGANISM: Thermoascus aurantiacus

<400> SEQUENCE: 34

```
Met Arg Ala Ile Gly Leu Leu Pro Gly Ile Ile Gly Ile Ala Gly Ala
1               5                   10                  15

Ala Cys Pro Tyr Met Thr Gly Glu Leu Pro Arg Ser Phe Ala Glu Asn
            20                  25                  30

Pro His Ala Ile Asn Arg Arg Ala Glu Gly Gly Gly Ala Ala Ala
        35                  40                  45

Glu Thr Glu Lys Phe Leu Ser Gln Phe Tyr Leu Asn Asp Asn Asp Thr
50                  55                  60

Phe Met Thr Thr Asp Val Gly Pro Ile Glu Asp Gln Asn Ser Leu
65                  70                  75                  80

Ser Ala Gly Asp Arg Gly Pro Thr Leu Leu Glu Asp Phe Ile Leu Arg
                85                  90                  95

Gln Lys Ile Gln Arg Phe Asp His Glu Arg Val Pro Glu Arg Ala Val
            100                 105                 110

His Ala Arg Gly Ala Gly Ala His Gly Val Phe Thr Ser Tyr Ala Asp
        115                 120                 125

Trp Ser Asn Ile Thr Ala Ala Ser Phe Leu Ser Ala Ala Gly Lys Glu
    130                 135                 140

Thr Pro Val Phe Val Arg Phe Ser Thr Val Ala Gly Ser Arg Gly Ser
145                 150                 155                 160

Ala Asp Thr Ala Arg Asp Val His Gly Phe Ala Thr Arg Phe Tyr Thr
                165                 170                 175

Asp Glu Gly Asn Phe Asp Ile Val Gly Asn Asn Ile Pro Val Phe Phe
            180                 185                 190

Ile Gln Asp Ala Ile Gln Phe Pro Asp Leu Ile His Ala Val Lys Pro
        195                 200                 205

Ser Pro Asn Asn Glu Ile Pro Gln Ala Ala Thr Ala His Asp Ser Ala
```

```
            210                 215                 220
Trp Asp Phe Phe Ser Gln Gln Pro Ser Ser Leu His Thr Leu Phe Trp
225                 230                 235                 240

Ala Met Ala Gly His Gly Ile Pro Arg Ser Tyr Arg Asn Met Asp Gly
            245                 250                 255

Phe Gly Ile His Thr Phe Arg Phe Val Thr Asp Gly Ala Ser Lys
            260                 265                 270

Leu Val Lys Phe His Trp Thr Ser Leu Gln Gly Lys Ala Ser Leu Val
            275                 280                 285

Trp Glu Glu Ala Gln Ala Val Ala Gly Lys Asn Ala Asp Tyr His Arg
290                 295                 300

Gln Asp Leu Trp Asp Ala Ile Glu Ala Gly Arg Tyr Pro Glu Trp Glu
305                 310                 315                 320

Leu Gly Val Gln Ile Met Asp Glu Glu Asp Gln Leu Arg Phe Gly Phe
            325                 330                 335

Asp Leu Leu Asp Pro Thr Lys Ile Val Pro Glu Glu Tyr Val Pro Ile
            340                 345                 350

Thr Lys Leu Gly Lys Met Gln Leu Asn Arg Asn Pro Leu Asn Tyr Phe
            355                 360                 365

Ala Glu Thr Glu Gln Ile Met Phe Gln Pro Gly His Val Val Arg Gly
            370                 375                 380

Ile Asp Phe Thr Glu Asp Pro Leu Leu Gln Gly Arg Leu Phe Ser Tyr
385                 390                 395                 400

Leu Asp Thr Gln Leu Asn Arg His Gly Gly Pro Asn Phe Glu Gln Ile
            405                 410                 415

Pro Ile Asn Arg Pro Arg Thr Pro Ile His Asn Asn Arg Asp Gly
            420                 425                 430

Ala Ala Gln Met Tyr Ile Pro Leu Asn Lys Ala Ala Tyr Thr Pro Asn
            435                 440                 445

Thr Leu Asn Asn Gly Ser Pro Lys Gln Ala Asn Gln Thr Val Gly Lys
            450                 455                 460

Gly Phe Phe Thr Thr Pro Gly Arg Thr Ala Ser Gly Arg Leu Val Arg
465                 470                 475                 480

Ala Val Ser Ser Thr Phe Ala Asp Val Trp Ser Gln Pro Arg Leu Phe
            485                 490                 495

Tyr Asn Ser Leu Val Pro Ala Glu Gln Gln Phe Leu Ile Asn Ala Ile
            500                 505                 510

Arg Phe Glu Thr Ala His Ile Thr Ser Asp Val Val Lys Asn Asn Val
            515                 520                 525

Ile Ile Gln Leu Asn Arg Val Ser Asn Asn Leu Ala Lys Arg Val Ala
530                 535                 540

Arg Ala Ile Gly Val Ala Glu Pro Glu Pro Asp Pro Thr Leu Tyr His
545                 550                 555                 560

Asn Asn Lys Thr Ala Asn Val Gly Val Phe Gly Lys Pro Leu Ala Arg
            565                 570                 575

Leu Asp Gly Leu Gln Val Gly Val Leu Ala Thr Val Asn Lys Pro Asp
            580                 585                 590

Ser Ile Lys Gln Ala Ala Ser Leu Lys Ala Ser Phe Ala Ala Asp Asn
            595                 600                 605

Val Asp Val Lys Val Ala Glu Arg Leu Ala Asp Gly Val Asp Glu
            610                 615                 620

Thr Tyr Ser Ala Ala Asp Ala Val Asn Phe Asp Ala Ile Leu Val Ala
625                 630                 635                 640
```

```
Asn Gly Ala Glu Gly Leu Phe Ala Arg Asp Ser Phe Thr Ala Arg Pro
                645                 650                 655

Ala Asn Ser Thr Thr Ala Thr Leu Tyr Pro Ala Gly Arg Pro Leu Gln
            660                 665                 670

Ile Leu Val Asp Gly Phe Arg Tyr Gly Lys Pro Val Gly Ala Leu Gly
        675                 680                 685

Ser Gly Ala Lys Ala Leu Asp Ala Ala Glu Ile Ser Thr Thr Arg Ala
    690                 695                 700

Gly Val Tyr Val Ala Asn Ser Thr Thr Asp Ser Phe Ile Asn Gly Val
705                 710                 715                 720

Arg Asp Gly Leu Arg Thr Phe Lys Phe Leu Asp Arg Phe Ala Ile Asp
                725                 730                 735

Glu Asp Ala Glu
            740

<210> SEQ ID NO 35
<211> LENGTH: 3060
<212> TYPE: DNA
<213> ORGANISM: Aspergillus fumigatus

<400> SEQUENCE: 35
```

| | | | | | |
|---|---|---|---|---|---|
| atgagattcg | gttggctcga | ggtggccgct | ctgacggccg | cttctgtagc | caatgcccag | 60 |
| gtttgtgatg | ctttcccgtc | attgtttcgg | atatagttga | caatagtcat | ggaaataatc | 120 |
| aggaattggc | tttctctcca | ccattctacc | cttcgccttg | ggctgatggc | agggagagt | 180 |
| gggcagatgc | ccatcgacgc | gccgtcgaga | tcgtttctca | gatgacactg | gcggagaagg | 240 |
| ttaaccttac | aacgggtact | gggtgggttg | cgactttttt | gttgacagtg | agctttcttc | 300 |
| actgaccatc | tacacagatg | ggaaatggac | cgatgcgtcg | gtcaaaccgg | cagcgttccc | 360 |
| aggtaagctt | gcaattctgc | aacaacgtgc | aagtgtagtt | gctaaaacgc | ggtggtgcag | 420 |
| acttggtatc | aactggggtc | tttgtggcca | ggattcccct | tgggtatccc | gtgactgtga | 480 |
| gctataccg | cggagtcttt | cagtccttgt | attatgtgct | gatgattgtc | tctgtatagc | 540 |
| tgacctcaac | tccgccttcc | ctgctggtac | taatgtcgcc | gcgacatggg | acaagacact | 600 |
| cgcctacctt | cgtggcaagg | ccatgggtga | ggaattcaac | gacaagggcg | tggacatttt | 660 |
| gctgggggcct | gctgctggtc | ctctcggcaa | atacccggac | ggcggcagaa | tctgggaagg | 720 |
| cttctctcct | gatccggttc | tcactggtgt | acttttcgcc | gaaactatca | agggtatcca | 780 |
| agacgcgggt | gtgattgcta | ctgccaagca | ttacattctg | aatgaacagg | agcatttccg | 840 |
| acaggttggc | gaggcccagg | gatatggtta | caacatcacg | gagacgatca | gctccaacgt | 900 |
| ggatgacaag | accatgcacg | agttgtacct | tggtgagta | gttgacactg | caaatgagga | 960 |
| ccttgattga | tttgactgac | ctggaatgca | ggcccttgc | agatgctgtg | cgcggtaaga | 1020 |
| ttttccgtag | acttgacctc | gcgacgaaga | aatcgctgac | gaaccatcgt | agctggcgtt | 1080 |
| ggcgctgtca | tgtgttccta | caatcaaatc | aacaacagct | acggttgtca | aaacagtcaa | 1140 |
| actctcaaca | agctcctcaa | ggctgagctg | gcttccaag | gcttcgtcat | gagtgactgg | 1200 |
| ggcgctcacc | acagcggtgt | cggcgctgcc | ctcgctgggt | tggatatgtc | gatgcctgga | 1260 |
| gacatttcct | tcgacgacgg | actctccttc | tggggcacga | acctaactgt | cagtgttctt | 1320 |
| aacggcaccg | ttccagcctg | gcgtgtcgat | gacatggctg | ttcgtatcat | gaccgcgtac | 1380 |
| tacaaggttg | gtcgtgaccg | tcttcgtatt | cccctaact | tcagctcctg | gacccgggat | 1440 |
| gagtacggct | gggagcattc | tgctgtctcc | gagggagcct | ggaccaaggt | gaacgacttc | 1500 |

-continued

```
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct ccccgaccg cggctgtgat    1680
aacggcactc ttgctatggc ctggggtagt ggtactgccg agttcccta ccttgtcacc    1740
cccgagcagg ctatccagcg agaggtcatc agcaacggcg gcaatgtctt gctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt tacatcagtg tcgacggcaa cgagggtgac    1980
cgcaaaaatc tcactctgtg aagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aacccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 36
<211> LENGTH: 863
<212> TYPE: PRT
<213> ORGANISM: Aspergillus fumigatus

<400> SEQUENCE: 36

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

-continued

Gly Ile Arg Asp Ser Asp Leu Asn Ser Ala Phe Pro Ala Gly Thr Asn
              100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Gly Ala His His Ser Gly
            275                 280                 285

Val Gly Ala Ala Leu Ala Gly Leu Asp Met Ser Met Pro Gly Asp Ile
        290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Glu Phe Pro Tyr Leu Val Thr Pro Glu
        450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Tyr
            500                 505                 510

Ile Ser Val Asp Gly Asn Glu Gly Asp Arg Lys Asn Leu Thr Leu Trp

Lys Asn Gly Glu Ala Val Ile Asp Thr Val Ser His Cys Asn Asn
515                 520                 525

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
                820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
850                 855                 860

<210> SEQ ID NO 37
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 37
cgcaatctat cgaatagcag                                              20

<210> SEQ ID NO 38

```
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 38
ctacatcgaa gctgaaagca cgaga                                           25

<210> SEQ ID NO 39
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 39
cgcaatctat cgaatagcag                                                 20

<210> SEQ ID NO 40
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 40
gacgtgcaac ttccttcaaa c                                               21

<210> SEQ ID NO 41
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 41
cttctatctt gggatgcttc acgatacgtg a                                    31

<210> SEQ ID NO 42
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 42
cgcgcccttg aatatcggag aaggt                                           25

<210> SEQ ID NO 43
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 43
atagtcaacc gcggactgcg caccatgcgg tctctcctgg ctcttgcccc                50

<210> SEQ ID NO 44
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 44
```
tcaggctttc gccacggagc ttaattaatt agaaagaggg gttggcgttg          50

<210> SEQ ID NO 45
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 45
agatcaccct ctgtgtattg caccatgcgg tctctcctgg ctcttgcccc t          51

<210> SEQ ID NO 46
<211> LENGTH: 53
<212> TYPE: DNA
<213> ORGANISM: Artificial Sequence
<220> FEATURE:
<223> OTHER INFORMATION: Artificial DNA Primer

<400> SEQUENCE: 46
ccggtcacga aagccttaat taactattag aaagaggggt tggcgttggt aag          53

<210> SEQ ID NO 47
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 47
gcttaggccc ttaagcttag gccggcttgc ttact          35

<210> SEQ ID NO 48
<211> LENGTH: 58
<212> TYPE: DNA
<213> ORGANISM: Artificial Sequence
<220> FEATURE:
<223> OTHER INFORMATION: Artificial DNA Primer

<400> SEQUENCE: 48
aggggcaaga gccaggagag accgcatggt gcaatacaca gagggtgatc ttacaagc          58

<210> SEQ ID NO 49
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 49
ctctatagag gaatcagcgt          20

<210> SEQ ID NO 50
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 50
tacacctcgg acgagtattc          20

<210> SEQ ID NO 51
<211> LENGTH: 20
<212> TYPE: DNA

```
<213> ORGANISM: Artificial Sequence
<220> FEATURE:
<223> OTHER INFORMATION: Artificial DNA Primer

<400> SEQUENCE: 51
tctagaggca cactagctgc                                                    20

<210> SEQ ID NO 52
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 52
ggcatgacct tttgatgatc g                                                  21

<210> SEQ ID NO 53
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 53
ttacaacgta cctacctagt                                                    20

<210> SEQ ID NO 54
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 54
ctctatagag gaatcagcgt                                                    20

<210> SEQ ID NO 55
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 55
cgtgtccccg atatggggtc gtggg                                              25

<210> SEQ ID NO 56
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 56
tcttgagccg catcgcatag a                                                  21

<210> SEQ ID NO 57
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 57
tacggtcagc gctcatgcga a                                                  21
```

<210> SEQ ID NO 58
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 58
atagtcaacc gcggactgcg caccatggcc agcctcttct ctttcaagat g    51

<210> SEQ ID NO 59
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 59
caggctttcg ccacggagct taattaatta caggcactgg tagtagtagg ggttc    55

<210> SEQ ID NO 60
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 60
cagttgggtg cacgagtggg ttacatcgaa ctgg    34

<210> SEQ ID NO 61
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 61
gaaagagaag aggctggcca tggtgcgcag tccgcggttg actattg    47

<210> SEQ ID NO 62
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 62
caatagtcaa ccgcggactg cgcaccatgg ccagcctctt ctctttc    47

<210> SEQ ID NO 63
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 63
gcgtcaggct ttcgccacgg agc    23

<210> SEQ ID NO 64
<211> LENGTH: 20
<212> TYPE: DNA
<213> ORGANISM: Artificial Sequence
<220> FEATURE:

<223> OTHER INFORMATION: Artificial DNA Primer

<400> SEQUENCE: 64
gtaatttgcc tgcttgaccg                                          20

<210> SEQ ID NO 65
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 65
tgaagatctg gtaggttgtg                                          20

<210> SEQ ID NO 66
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 66
tcattgactg tctgtcctct                                          20

<210> SEQ ID NO 67
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 67
taccatgact gtcacgatag                                          20

<210> SEQ ID NO 68
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 68
gtaatttgcc tgcttgaccg                                          20

<210> SEQ ID NO 69
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 69
tgaagatctg gtaggttgtg                                          20

<210> SEQ ID NO 70
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 70
cgagatgacg gccaacttcc                                          20

```
<210> SEQ ID NO 71
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 71
tcattgactg tctgtcctct                                                   20

<210> SEQ ID NO 72
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 72
ggaagttggc cgtcatctcg                                                   20

<210> SEQ ID NO 73
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 73
taccatgact gtcacgatag                                                   20

<210> SEQ ID NO 74
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 74
ttccccaacc acgaccacct                                                   20

<210> SEQ ID NO 75
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 75
taccatgact gtcacgatag                                                   20

<210> SEQ ID NO 76
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 76
ggcatgacct tttgatgatc g                                                 21

<210> SEQ ID NO 77
<211> LENGTH: 20
<212> TYPE: DNA
<213> ORGANISM: Artificial Sequence
<220> FEATURE:
<223> OTHER INFORMATION: Artificial DNA Primer
```

```
<400> SEQUENCE: 77
taccatgact gtcacgatag                                               20

<210> SEQ ID NO 78
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 78
aatgacccat agggagacaa acagcataat                                    30

<210> SEQ ID NO 79
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 79
tgttggacgc aggatttttgg a                                            21

<210> SEQ ID NO 80
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 80
cgctgaaatg cgcccgccac ct                                            22

<210> SEQ ID NO 81
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 81
gggcggacag acggggcaaa                                               20

<210> SEQ ID NO 82
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 82
cgctgaaatg cgcccgccac ct                                            22

<210> SEQ ID NO 83
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 83
cgttctcgcc ggcgtttgcc                                               20

<210> SEQ ID NO 84
<211> LENGTH: 22
```

```
<212> TYPE: DNA
<213> ORGANISM: Artificial Sequence
<220> FEATURE:
<223> OTHER INFORMATION: Artificial DNA Primer

<400> SEQUENCE: 84
cagagaaagg tagctggaga gc                                          22

<210> SEQ ID NO 85
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 85
gtccatttcg attccgcata g                                           21

<210> SEQ ID NO 86
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 86
atcaccctct gtgtattgca ccatgctgtc ttcgacgact cgc                   43

<210> SEQ ID NO 87
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 87
gcccggtcac gaaagcctta tcgacttctt ctagaacgtc ggc                   43

<210> SEQ ID NO 88
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 88
gccgacgttc tagaagaagt cgataaggct tcgtgaccg ggc                    43

<210> SEQ ID NO 89
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 89
caggtgtcag tcacctctag ttaattaact cggagttgtt atacgctact cg         52

<210> SEQ ID NO 90
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 90
```

-continued tataagctta agcatgcgtt cctccccct c    31

<210> SEQ ID NO 91
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 91
ctgcagaatt ctacaggcac tgatggtacc ag    32

<210> SEQ ID NO 92
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 92
acgcgtcgac gaattctagg ctaggtatgc gaggca    36

<210> SEQ ID NO 93
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 93
catggtgcaa tacacagagg gtg    23

<210> SEQ ID NO 94
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 94
gtgtattgca ccatggcgtt cctccccct cc    32

<210> SEQ ID NO 95
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 95
ggagggggga ggaacgccat ggtgcaatac a    31

<210> SEQ ID NO 96
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 96
ccctctgtgt attgcaccat gatgactccc acggcgat    38

<210> SEQ ID NO 97
<211> LENGTH: 38
<212> TYPE: DNA
<213> ORGANISM: Artificial Sequence

```
<220> FEATURE:
<223> OTHER INFORMATION: Artificial DNA Primer

<400> SEQUENCE: 97
gatctgcggc cgcgaattttt attgctgcag cacccccg                             38

<210> SEQ ID NO 98
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 98
ccgcggactg cgcaccatgg tccatctttc ttccct                                36

<210> SEQ ID NO 99
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 99
ttcgccacgg agcttattac aggcactggt agtagt                                36

<210> SEQ ID NO 100
<211> LENGTH: 2223
<212> TYPE: DNA
<213> ORGANISM: Thermoascus aurantiacus

<400> SEQUENCE: 100
atgcgagcaa tcggcttgtt gcctggcatc atcggtatcg cgggtgccgc atgtccctac       60
atgacaggcg agctccctcg gtcgttcgcc gaaaaccctc acgccattaa caggcgagcg      120
gagggaggag gaggcgcagc agccgaaaca gaaaagttct tgtcccagtt ctatttgaac      180
gataacgaca cgttcatgac tacgatgtc ggtggaccga ttgaggacca gaactccctc       240
tcggcaggag atcgaggacc caccctcttg gaagatttca tcctccgtca gaaaattcag      300
cggttcgacc acgaaagggt gccggaacgc gcagtccatg cccgaggcgc aggtgcccat      360
ggcgtgttca cttcctacgc agactggtcg aacatcactg cagcgtcgtt cctctccgca      420
gcaggcaagg agacacccgt gttcgtcagg ttctcgactg tggcaggctc aggggatcg       480 gcagacactg cacgcgatgt ccatggtttc gccacaaggt tctataccga tgagggtaac      540
ttcgatatcg tgggcaacaa cattcccgtc ttcttcatcc aggacgccat ccagttcccc      600
gacttgatcc atgcggtgaa gccgtcgccc aacaacgaaa ttcctcaggc agccacagca      660
cacgattcgg catgggactt cttctcgcag cagccgtcgt cgttgcatac cctcttctgg      720
gccatggcag gacacggaat tcctcggtcc tatcgaaaca tggacggatt cggcatccac      780
accttcaggt tcgtcacaga cgatggagcg tcgaagttgg tgaagttcca ctggacctcc      840
ctccagggca aggcgtcgtt ggtctgggaa gaagcacagg ccgtcgcagg caaaaacgcc      900
gattaccaca ggcaggattt gtgggatgcg atcgaagcag gacgctatcc tgaatgggaa      960
ttgggtgtgc agatcatgga cgaagaagac cagttgcggt tcggattcga tttgttggac     1020
cctaccaaga tcgtccccga agaatacgtc cccatcacca aattgggcaa gatgcagttg     1080
aaccgtaacc cgttgaacta tttcgcggaa actgaacaga ttatgttcca gcctggccac     1140
gtggtgaggg gcatcgattt caccgaggac cctttgctcc agggccggtt gttctcgtac     1200
```

-continued

| | |
|---|---|
| ctcgacaccc agctcaaccg gcatggcgga cccaacttcg agcagattcc catcaaccga | 1260 |
| cctcgcactc cgatccataa caacaacagg gatggtgcag cacagatgta catccccttg | 1320 |
| aacaaggcag cgtacactcc caacacgctc aacaacggtt cgcccaagca ggcgaaccag | 1380 |
| actgtgggca agggcttctt caccactcct ggacgcactg cctccggcag gctcgtccga | 1440 |
| gcggtctcgt cgactttcgc ggacgtctgg tcgcagccca ggctcttcta caactcgctc | 1500 |
| gtgcctgccg aacagcagtt cctcattaac gcaatccgat tcgagacggc ccacattacg | 1560 |
| tcggatgtgg tcaagaacaa cgtgatcatc cagctcaacc gagtctccaa caacttggcg | 1620 |
| aaacgggtgg caagggcgat cggcgtggcc gagcccgaac ccgaccccac cttgtaccac | 1680 |
| aacaacaaga cagcaaacgt gggcgtgttc ggaaagccgt tggccaggct cgacggattg | 1740 |
| caggtcggcg tcctcgcaac cgtcaacaag ccggactcca tcaagcaggc agcctccctc | 1800 |
| aaggcctcgt tcgcagcaga taacgtcgac gtcaaagtcg tcgcggagag gctcgcagat | 1860 |
| ggcgtggacg aaacctactc cgcagccgat gccgtcaact tcgacgcgat cctcgtggca | 1920 |
| aacggagccg agggattgtt cgcacgggac tcgttcacag cacgccctgc aaactcgacc | 1980 |
| actgccacac tctaccctgc aggccgaccg ctccagattt tggtggacgg attcaggtac | 2040 |
| ggcaagcctg tgggtgcact cggatcggga gcaaaggccc tcgatgcagc cgaaatctcg | 2100 |
| actacaaggg caggcgtcta tgtcgcgaac tcgacaaccg attccttcat caacggtgtc | 2160 |
| agggacggcc tccgtacttt caaattcctc gatcgcttcg ccatcgacga agacgccgag | 2220 |
| tga | 2223 |

<210> SEQ ID NO 101
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 101
cggactgcgc accatgcgag caatcggctt gtt                                33

<210> SEQ ID NO 102
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 102
tcgccacgga gcttatcact cggcgtcttc gtcga                              35

<210> SEQ ID NO 103
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 103
cggactgcgc accatgcgta ccttctcgtc tctt                               34

<210> SEQ ID NO 104
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 104
tcgccacgga gcttatcaag ccgcaagagc agacg    35

<210> SEQ ID NO 105
<211> LENGTH: 1008
<212> TYPE: DNA
<213> ORGANISM: Thermoascus aurantiacus

<400> SEQUENCE: 105

| | |
|---|---|
| atgaagctcg gctctctcgt gctcgctctc agcgcagcta ggcttacact gtcggcccct | 60 |
| ctcgcagaca gaaagcagga gaccaagcgt gcgaaagtat tccaatggtt cggttcgaac | 120 |
| gagtccggtg ctgaattcgg aagccagaac cttccaggag tcgagggaaa ggattatata | 180 |
| tggcctgatc ccaacaccat tgacacattg atcagcaagg ggatgaacat ctttcgtgtc | 240 |
| ccctttatga tggagagatt ggttcccaac tcaatgaccg gctctccgga tccgaactac | 300 |
| ctggcagatc tcatagcgac tgtaaatgca atcacccaga aggtgcctac cgccgtcgtc | 360 |
| gatcctcata actacggcag atactacaat tctataatct cgagcccttc cgatttccag | 420 |
| accttctgga aaacggtcgc ctcacagttt gcttcgaatc cactggtcat cttcgacact | 480 |
| aataacgaat accacgatat ggaccagacc ttagtcctca atctcaacca ggccgctatc | 540 |
| gacggcatcc gttccgccgg agccacttcc cagtacatct ttgtcgaggg caattcgtgg | 600 |
| accggggcat ggacctggac gaacgtgaac gataacatga aaagcctgac cgacccatct | 660 |
| gacaagatca tatacgagat gcaccagtac ctggactctg acggatccgg gacatcagcg | 720 |
| acctgcgtat cttcgaccat cggtcaagag cgaatcacca gcgcaacgca gtggctcagg | 780 |
| gccaacggga gaagggcat catcggcgag tttgcgggcg gagccaacga cgtctgcgag | 840 |
| acggccatca cgggcatgct ggactacatg gcccagaaca cagacgtctg gactggcgcc | 900 |
| atctggtggg cggccgggcc gtggtgggga gactacatat ctccatgga gccggacaat | 960 |
| ggcatcgcgt atcagcagat acttcctatt ttgactccgt atctttga | 1008 |

<210> SEQ ID NO 106
<211> LENGTH: 335
<212> TYPE: PRT
<213> ORGANISM: Thermoascus aurantiacus

<400> SEQUENCE: 106

Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
                20                  25                  30

Val Phe Gln Trp Phe Gly Ser Asn Glu Ser Gly Ala Glu Phe Gly Ser
            35                  40                  45

Gln Asn Leu Pro Gly Val Glu Gly Lys Asp Tyr Ile Trp Pro Asp Pro
        50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
                100                 105                 110

Gln Lys Gly Ala Tyr Ala Val Val Asp Pro His Asn Tyr Gly Arg Tyr
            115                 120                 125

-continued

```
Tyr Asn Ser Ile Ile Ser Ser Pro Ser Asp Phe Gln Thr Phe Trp Lys
    130             135             140

Thr Val Ala Ser Gln Phe Ala Ser Asn Pro Leu Val Ile Phe Asp Thr
145             150             155             160

Asn Asn Glu Tyr His Asp Met Asp Gln Thr Leu Val Leu Asn Leu Asn
            165             170             175

Gln Ala Ala Ile Asp Gly Ile Arg Ser Ala Gly Ala Thr Ser Gln Tyr
            180             185             190

Ile Phe Val Glu Gly Asn Ser Trp Thr Gly Ala Trp Thr Trp Thr Asn
        195             200             205

Val Asn Asp Asn Met Lys Ser Leu Thr Asp Pro Ser Asp Lys Ile Ile
    210             215             220

Tyr Glu Met His Gln Tyr Leu Asp Ser Asp Gly Ser Gly Thr Ser Ala
225             230             235             240

Thr Cys Val Ser Ser Thr Ile Gly Gln Glu Arg Ile Thr Ser Ala Thr
            245             250             255

Gln Trp Leu Arg Ala Asn Gly Lys Lys Gly Ile Ile Gly Glu Phe Ala
            260             265             270

Gly Gly Ala Asn Asp Val Cys Glu Thr Ala Ile Thr Gly Met Leu Asp
        275             280             285

Tyr Met Ala Gln Asn Thr Asp Val Trp Thr Gly Ala Ile Trp Trp Ala
    290             295             300

Ala Gly Pro Trp Trp Gly Asp Tyr Ile Phe Ser Met Glu Pro Asp Asn
305             310             315             320

Gly Ile Ala Tyr Gln Gln Ile Leu Pro Ile Leu Thr Pro Tyr Leu
            325             330             335
```

ENZYME COMPOSITIONS AND USES THEREOF

CROSS-REFERENCE TO RELATED APPLICATIONS

This application is a 35 U.S.C. § 371 national application of PCT/US2015/034179 filed Jun. 4, 2015, which claims priority or the benefit under 35 U.S.C. § 119 of U.S. Provisional Application No. 62/093,230 filed Dec. 17, 2014 and U.S. Provisional Application No. 62/009,018 filed Jun. 6, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to enzyme compositions, recombinant fungal host cells producing the enzyme compositions, and processes of producing and using the enzyme compositions.

Description of the Related Art

Lignocellulose, the world's largest renewable biomass resource, is composed mainly of lignin, cellulose, and hemicellulose. Cellulose is a polymer of glucose linked by beta-1,4-bonds known as beta-linked glucans. Hemicellulose is composed of xylans, which are polysaccharides formed from 1,4-β-glycoside-linked D-xylopyranoses.

Many microorganisms produce enzymes that hydrolyze the beta-linked glucans and xylans. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Xylanases (e.g., endo-1,4-beta-xylanase, EC 3.2.1.8) hydrolyze internal β-1,4-xylosidic linkages in xylan to produce smaller molecular weight xylose and xylo-oligomers. Beta-xylosidases catalyze the exo-hydrolysis of short beta (1→4)-xylooligosaccharides to remove successive D-xylose residues from non-reducing termini.

The conversion of lignocellulosic feedstocks into ethanol has the advantages of the availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art for new enzyme compositions that can deconstruct cellulosic or hemicellulosic material more efficiently.

The present invention provides enzyme compositions and processes of producing and using the enzyme compositions.

SUMMARY OF THE INVENTION

The present invention relates to enzyme compositions, comprising (A) (i) a cellobiohydrolase I, (ii) a cellobiohydrolase II, and (iii) at least one enzyme selected from the group consisting of a beta-glucosidase or a variant thereof, an AA9 polypeptide having cellulolytic enhancing activity, a GH10 xylanase, and a beta-xylosidase; (B) (i) a GH10 xylanase and (ii) a beta-xylosidase; or (C) (i) a cellobiohydrolase I, (ii) a cellobiohydrolase II, (iii) a GH10 xylanase, and (iv) a beta-xylosidase;

wherein the cellobiohydrolase I is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70% sequence identity to the mature polypeptide of SEQ ID NO: 2; (iii) a cellobiohydrolase I encoded by a polynucleotide comprising or consisting of a nucleotide sequence having at least 70% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof;

wherein the cellobiohydrolase II is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70% sequence identity to the mature polypeptide of SEQ ID NO: 4; (iii) a cellobiohydrolase II encoded by a polynucleotide comprising or consisting of a nucleotide sequence having at least 70% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof;

wherein the beta-glucosidase is selected from the group consisting of: (i) a beta-glucosidase comprising or consisting of the mature polypeptide of SEQ ID NO: 6; (ii) a beta-glucosidase comprising or consisting of an amino acid sequence having at least 70% sequence identity to the mature polypeptide of SEQ ID NO: 6; (iii) a beta-glucosidase encoded by a polynucleotide comprising or consisting of a nucleotide sequence having at least 70% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof;

wherein the xylanase is selected from the group consisting of: (i) a xylanase comprising or consisting of the mature polypeptide of SEQ ID NO: 10 or the mature polypeptide of SEQ ID NO: 12; (ii) a xylanase comprising or consisting of an amino acid sequence having at least 70% sequence identity to the mature polypeptide of SEQ ID NO: 10 or the mature polypeptide of SEQ ID NO: 12; (iii) a xylanase encoded by a polynucleotide comprising or consisting of a nucleotide sequence having at least 70% sequence identity to the mature polypeptide coding sequence of SEQ ID NO: 9 or the mature polypeptide coding sequence of SEQ ID NO: 11; and (iv) a xylanase encoded by a polynucleotide that hybridizes under at least high stringency conditions, e.g., very high stringency conditions, with the mature polypeptide coding sequence of SEQ ID NO: 9 or the mature polypeptide coding sequence of SEQ ID NO: 11; or the full-length complement thereof; and wherein the beta-xylosidase is selected from the group consisting of: (i) a beta-xylosidase comprising or consisting of the mature polypeptide of SEQ ID NO: 14; (ii) a beta-xylosidase comprising or consisting of an amino acid sequence having at least 70% sequence identity to the mature polypeptide of SEQ ID NO: 14; (iii) a beta-xylosidase encoded by a polynucleotide comprising or consisting of a nucleotide sequence having at least 70% sequence identity to the mature polypeptide coding sequence of SEQ ID NO: 13; and (iv) a beta-xylosidase encoded by a polynucleotide that hybridizes under at least high stringency conditions, e.g., very high stringency conditions, with the mature polypeptide coding sequence of SEQ ID NO: 13 or the full-length complement thereof. In one aspect, the enzyme compositions further comprise an endoglucanase I. In another aspect, the enzyme compositions further comprise an endoglucanase II. In another aspect, the enzyme compositions further comprise an endoglucanase I and an endoglucanase II. In another aspect, the enzyme compositions further or even further comprise a catalase.

The present invention also relates to recombinant fungal host cells, comprising polynucleotides encoding the enzyme compositions of the present invention.

The present invention also relates to processes of producing an enzyme composition, comprising: (a) cultivating one or more (e.g., several) fungal host cells of the present invention under conditions conducive for production of the enzyme composition; and optionally (b) recovering the enzyme composition.

The present invention also relates to processes for degrading a cellulosic or hemicellulosic material, comprising: treating the cellulosic or hemicellulosic material with an enzyme composition of the present invention. In one aspect, the processes further comprise recovering the degraded cellulosic or hemicellulosic material.

The present invention also relates to processes for producing a fermentation product, comprising: (a) saccharifying a cellulosic or hemicellulosic material with an enzyme composition of the present invention; (b) fermenting the saccharified cellulosic or hemicellulosic material with one or more (e.g., several) fermenting microorganisms to produce the fermentation product; and (c) recovering the fermentation product from the fermentation.

The present invention further relates to processes of fermenting a cellulosic or hemicellulosic material, comprising: fermenting the cellulosic or hemicellulosic material with one or more (e.g., several) fermenting microorganisms, wherein the cellulosic or hemicellulosic material is saccharified with an enzyme composition of the present invention. In one aspect, the fermenting of the cellulosic or hemicellulosic material produces a fermentation product. In another aspect, the processes further comprise recovering the fermentation product from the fermentation.

DEFINITIONS

Figure 1:
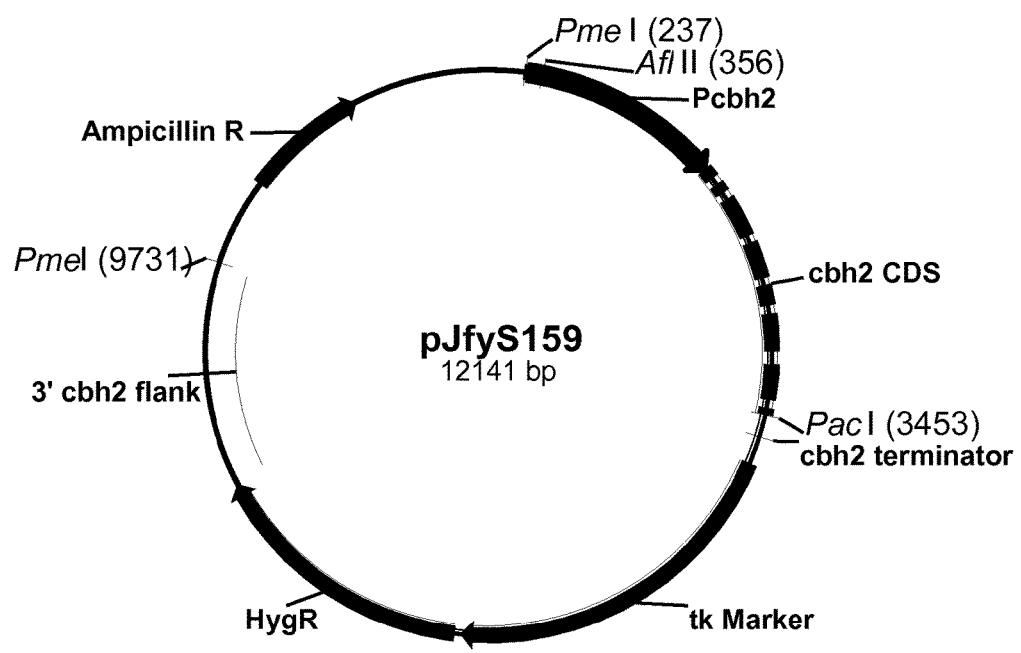
FIG. 1 shows a restriction map of plasmid pJfyS159.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity, e.g., cellulase composition. Cellulolytic enhancing activity can be determined by measuring the increase in reducing sugars or the increase of the total of cellobiose and glucose from the hydrolysis of the cellulosic material by the cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at leas 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., manganese or copper.

The AA9 polypeptide can also be used in the presence of a dioxy compound, a bicylic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Aspartic protease: The term "aspartic protease" means a protease that involves an aspartate residue(s) for catalyzing the hydrolysis of peptide bonds in peptides and proteins. Aspartic proteases are a family of protease enzymes that generally have two highly-conserved aspartates in the active site and are optimally active at acidic pH (Szecsi, 1992, *Scand. J. Clin. Lab. In vest.* Suppl. 210: 5-22). Aspartic protease activity can be determined according to the procedure described by Aikawa et al., 2001, *J. Biochem.* 129: 791-794.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of $2H_2O_2$ to $O_2 + 2 H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics, in Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, sugar cane straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24:

452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide having one or more (e.g., several) amino acids absent from the amino and/or carboxyl terminus of a mature polypeptide, wherein the fragment has enzyme activity. In one aspect, a fragment contains at least 85%, e.g., at least 90% or at least 95% of the amino acid residues of the mature polypeptide of an enzyme.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of a cellobiohydrolase I is amino acids 26 to 532 of SEQ ID NO: 2 based on the SignalP 3.0 program (Bendtsen et al., 2004, *J. Mol. Biol.* 340: 783-795) that predicts amino acids 1 to 25 of SEQ ID NO: 2 are a signal peptide. In another aspect, the mature polypeptide of a cellobiohydrolase II is amino acids 19 to 464 of SEQ ID NO: 4 based on the SignalP 3.0 program that predicts amino acids 1 to 18 of SEQ ID NO: 4 are a signal peptide. In another aspect, the mature polypeptide of a beta-glucosidase is amino acids 20 to 863 of SEQ ID NO: 6 based on the SignalP 3.0 program that predicts amino acids 1 to 19 of SEQ ID NO: 6 are a signal peptide. In another aspect, the mature polypeptide of a beta-glucosidase variant is amino acids 20 to 863 of SEQ ID NO: 36 based on the SignalP 3.0 program that predicts amino acids 1 to 19 of SEQ ID NO: 36 are a signal peptide. In another aspect, the mature polypeptide of an AA9 polypeptide is amino acids 26 to 253 of SEQ ID NO: 8 based on the SignalP 3.0 program that predicts amino acids 1 to 25 of SEQ ID NO: 8 are a signal peptide. In another aspect, the mature polypeptide of a GH10 xylanase is amino acids 21 to 405 of SEQ ID NO: 10 based on the SignalP 3.0 program that predicts amino acids 1 to 20 of SEQ ID NO: 10 are a signal peptide. In another aspect, the mature polypeptide of a GH10 xylanase is amino acids 20 to 398 of SEQ ID NO: 12 based on the SignalP 3.0 program that predicts amino acids 1 to 19 of SEQ ID NO: 12 are a signal peptide. In another aspect, the mature polypeptide of a beta-xylosidase is amino acids 22 to 796 of SEQ ID NO: 14 based on the SignalP 3.0 program that predicts amino acids 1 to 21 of SEQ ID NO: 14 are a signal peptide. In another aspect, the mature polypeptide of an endoglucanase I is amino acids 23 to 459 of SEQ ID NO: 16 based on the SignalP 3.0 program that predicts amino acids 1 to 22 of SEQ ID NO: 16 are a signal peptide. In another aspect, the mature polypeptide of an endoglucanase II is amino acids 22 to 418 of SEQ ID NO: 18 based on the SignalP 3.0 program that predicts amino acids 1 to 21 of SEQ ID NO: 18 are a signal peptide. In another aspect, the mature polypeptide of a *Trichoderma reesei* cellobiohydrolase I is amino acids 18 to 514 of SEQ ID NO: 20 based on the SignalP 3.0 program that predicts amino acids 1 to 17 of SEQ ID NO: 20 are a signal peptide. In another aspect, the mature polypeptide of a *Trichoderma reesei* cellobiohydrolase II is amino acids 19 to 471 of SEQ ID NO: 22 based on the SignalP 3.0 program that predicts amino acids 1 to 18 of SEQ ID NO: 22 are a signal peptide. In another aspect, the mature polypeptide of a *Trichoderma reesei* beta-glucosidase is amino acids 20 to 744 of SEQ ID NO: 24 based on the SignalP 3.0 program that predicts amino acids 1 to 19 of SEQ ID NO: 24 are a signal peptide. In another aspect, the mature polypeptide of a *Trichoderma reesei* xylanase I is amino acids 20 to 229 of SEQ ID NO: 26 based on the SignalP 3.0 program that predicts amino acids 1 to 19 of SEQ ID NO: 26 are a signal peptide. In another aspect, the mature polypeptide of a *Trichoderma reesei* xylanase II is amino acids 20 to 223 of SEQ ID NO: 28 based on the SignalP 3.0 program that predicts amino acids 1 to 19 of SEQ ID NO: 28 are a signal peptide. In another aspect, the mature polypeptide of a *Trichoderma reesei* xylanase III is amino acids 17 to 347 of SEQ ID NO: 30 based on the SignalP 3.0 program that predicts amino acids 1 to 16 of SEQ ID NO: 30 are a signal peptide. In another aspect, the mature polypeptide of a *Trichoderma reesei* beta-xylosidase is amino acids 21 to 796 of SEQ ID NO: 32 based on the SignalP 3.0 program that predicts amino acids 1 to 20 of SEQ ID NO: 32 are a signal peptide. In another aspect, the mature polypeptide of a catalase is amino acids 17 to 740 of SEQ ID NO: 34 based on the SignalP 3.0 program that predicts amino acids 1 to 16 of SEQ ID NO: 34 are a signal peptide. In another aspect, the mature polypeptide of an endoglucanase II is amino acids 19 to 335 of SEQ ID NO: 106 based on the SignalP 3.0 program that predicts amino acids 1 to 18 of SEQ ID NO: 106 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity. In one aspect, the mature polypeptide coding sequence of a cellobiohydrolase I is nucleotides 76 to 1727 of SEQ ID NO: 1 or the cDNA sequence thereof based on the SignalP 3.0 program that predicts nucleotides 1 to 75 of SEQ ID NO: 1 encode a signal peptide. In another aspect, the mature polypeptide coding sequence of a cellobiohydrolase II is nucleotides 55 to 1895 of SEQ ID NO: 3 or the cDNA sequence thereof based on the SignalP 3.0 program that predicts nucleotides 1 to 54 of SEQ ID NO: 3 encode a signal peptide. In another aspect, the mature polypeptide coding sequence of a beta-glucosidase is nucleotides 58 to 3057 of SEQ ID NO: 5 or the cDNA sequence thereof based on the SignalP 3.0 program that predicts nucleotides 1 to 57 of SEQ ID NO: 5 encode a signal peptide. In another aspect, the mature polypeptide coding sequence of a beta-glucosidase variant is nucleotides 58 to 3057 of SEQ ID NO: 35 or the cDNA sequence thereof based on the SignalP 3.0 program that predicts nucleotides 1 to 57 of SEQ ID NO: 35 encode a signal peptide. In another aspect, the mature polypeptide coding sequence of an AA9 polypeptide is nucleotides 76 to 832 of SEQ ID NO: 7 or the cDNA sequence thereof based on the SignalP 3.0 program that predicts nucleotides 1 to 75 of SEQ ID NO: 7 encode a signal peptide. In another aspect, the mature polypeptide coding sequence of a GH10 xylanase is nucleotides 124 to 1517 of SEQ ID NO: 9 or the cDNA sequence thereof based on the SignalP 3.0 program that predicts nucleotides 1 to 123 of SEQ ID NO: 9 encode a signal peptide. In another aspect, the mature polypeptide coding sequence of a GH10 xylanase is nucleotides 58 to 1194 of SEQ ID NO: 11 based on the SignalP 3.0 program that predicts nucleotides 1 to 57 of SEQ ID NO: 11 encode a signal peptide. In another aspect, the mature polypeptide coding sequence of a beta-xylosidase is nucleotides 64 to 2388 of SEQ ID NO: 13 based on the SignalP 3.0 program that predicts nucleotides 1 to 63 of SEQ ID NO: 13 encode a signal peptide. In another aspect, the mature polypeptide coding sequence of an endoglucanase I is nucleotides 67 to 1504 of SEQ ID NO: 15 or the cDNA sequence thereof based on the SignalP 3.0 program that predicts nucleotides 1 to 66 of SEQ ID NO: 15 encode a signal peptide. In another aspect, the mature polypeptide coding sequence of an endoglucanase II is nucleotides 64 to 1504 of SEQ ID NO: 17 based on the SignalP 3.0 program that predicts nucleotides 1 to 63 of SEQ ID NO: 17 encode a signal peptide. In another aspect, the mature polypeptide coding sequence of a *Trichoderma reesei* cellobiohydrolase I is nucleotides 52 to 1545 of SEQ ID NO: 19 or the cDNA sequence thereof based on the SignalP 3.0 program that predicts nucleotides 1 to 51 of SEQ ID NO: 19 encode a signal peptide. In another aspect, the mature polypeptide coding sequence of a *Trichoderma reesei* cellobiohydrolase II is nucleotides 55 to 1608 of SEQ ID NO: 21 or the cDNA sequence thereof based on the SignalP 3.0 program that predicts nucleotides 1 to 54 of SEQ ID NO: 21 encode a signal peptide. In another aspect, the mature polypeptide coding sequence of a *Trichoderma reesei* beta-glucosidase is nucleotides 58 to 2612 of SEQ ID NO: 23 or the cDNA sequence thereof based on the SignalP 3.0 program that predicts nucleotides 1 to 57 of SEQ ID NO: 23 encode a signal peptide. In another aspect, the mature polypeptide coding sequence of a *Trichoderma reesei* xylanase I is nucleotides 58 to 749 of SEQ ID NO: 25 or the cDNA sequence thereof based on the SignalP 3.0 program that predicts nucleotides 1 to 57 of SEQ ID NO: 25 encode a signal peptide. In another aspect, the mature polypeptide coding sequence of a *Trichoderma reesei* xylanase II is nucleotides 58 to 778 of SEQ ID NO: 27 or the cDNA sequence thereof based on the SignalP 3.0 program that predicts nucleotides 1 to 57 of SEQ ID NO: 27 encode a signal peptide. In another aspect, the mature polypeptide coding sequence of a *Trichoderma reesei* xylanase III is nucleotides 49 to 1349 of SEQ ID NO: 29 or the cDNA sequence thereof based on the SignalP 3.0 program that predicts nucleotides 1 to 48 of SEQ ID NO: 29 encode a signal peptide. In another aspect, the mature polypeptide coding sequence of a *Trichoderma reesei* beta-xylosidase is nucleotides 61 to 2391 of SEQ ID NO: 31 or the cDNA sequence thereof based on the SignalP 3.0 program that predicts nucleotides 1 to 60 of SEQ ID NO: 31 encode a signal peptide. In another aspect, the mature polypeptide coding sequence of a catalase is nucleotides 49 to 2499 of SEQ ID NO: 33 or the cDNA sequence thereof based on the SignalP 3.0 program that predicts nucleotides 1 to 48 of SEQ ID NO: 33 encode a signal peptide. In another aspect, the mature polypeptide coding sequence of an endoglucanase II is nucleotides 55 to 1005 of SEQ ID NO: 105 or the genomic DNA sequence thereof based on the SignalP 3.0 program that predicts nucleotides 1 to 54 of SEQ ID NO: 105 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency Conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence, wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that involves a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem A G, Bubendorf, Switzerland) in 100 mM NaCl-100 mM MOPS pH 7.0 at 50° C. for 3 hours and then the absorbance at 405 nm is measured.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Trypsin-like serine protease: The term "trypsin-like serine protease" means a protease with a substrate specificity similar to trypsin that involves a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Whole broth preparation: The term "whole broth preparation" means a composition produced by a naturally-occurring source, i.e., a naturally-occurring microorganism that is unmodified with respect to the cellulolytic and/or hemicellulolytic enzymes produced by the naturally-occurring microorganism, or a non-naturally-occurring source, i.e., a non-naturally-occurring microorganism, e.g., mutant, that is unmodified with respect to the cellulolytic and/or hemicellulolytic enzymes produced by the non-naturally-occurring microorganism.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270.

Xylan degrading activity can also be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

DETAILED DESCRIPTION OF THE INVENTION

Enzyme Compositions

The present invention relates to enzyme compositions, comprising: (A) (i) a cellobiohydrolase I, (ii) a cellobiohydrolase II, and (iii) at least one enzyme selected from the group consisting of a beta-glucosidase or a variant thereof, an AA9 polypeptide having cellulolytic enhancing activity, a GH10 xylanase, and a beta-xylosidase; (B) (i) a GH10 xylanase and (ii) a beta-xylosidase; or (C) (i) a cellobiohydrolase I, (ii) a cellobiohydrolase II, (iii) a GH10 xylanase, and (iv) a beta-xylosidase;

wherein the cellobiohydrolase I is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof;

wherein the cellobiohydrolase II is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof;

wherein the beta-glucosidase is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof;

wherein the xylanase is selected from the group consisting of: (i) a xylanase comprising or consisting of the mature polypeptide of SEQ ID NO: 10 or the mature polypeptide of SEQ ID NO: 12; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10 or the mature polypeptide of SEQ ID NO: 12; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the mature polypeptide coding sequence of SEQ ID NO: 11; and (iv) a xylanase encoded by a polynucleotide that hybridizes under at least high stringency conditions, e.g., very high stringency conditions, with the mature polypeptide coding sequence of SEQ ID NO: 9 or the mature polypeptide coding sequence of SEQ ID NO: 11; or the full-length complement thereof; and wherein the beta-xylosidase is selected from the group consisting of: (i) a beta-xylosidase comprising or consisting of the mature polypeptide of SEQ ID NO: 14; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13; and (iv) a beta-xylosidase encoded by a polynucleotide that hybridizes under at least high stringency conditions, e.g., very high stringency conditions, with the mature polypeptide coding sequence of SEQ ID NO: 13 or the full-length complement thereof.

In one aspect, the AA9 (GH61) polypeptide is any AA9 polypeptide having cellulolytic enhancing activity. Examples of AA9 polypeptides include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, WO 2009/033071, WO 2012/027374, and WO 2012/068236), *Aspergillus fumigatus* (WO 2010/138754), *Penicillium pinophilum* (WO 2011/005867), *Thermoascus* sp. (WO 2011/039319), *Penicillium* sp. (*emersonii*) (WO 2011/041397 and WO 2012/000892), *Thermoascus crustaceous* (WO 2011/041504), *Aspergillus aculeatus* (WO 2012/125925), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206), *Talaromyces emersonii* (WO 2012/000892), *Trametes versicolor* (WO 2012/092676 and WO 2012/093149), and *Talaromyces thermophilus* (WO 2012/129697 and WO 2012/130950); which are incorporated herein by reference in their entireties.

In another aspect, the AA9 polypeptide having cellulolytic enhancing activity is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

In one embodiment, the enzyme composition comprises the cellobiohydrolase I, the cellobiohydrolase II, and the beta-glucosidase or a variant thereof, described above.

In another embodiment, the enzyme composition comprises the cellobiohydrolase I, the cellobiohydrolase II, and the AA9 polypeptide having cellulolytic enhancing activity, described above.

In another embodiment, the enzyme composition comprises the cellobiohydrolase I, the cellobiohydrolase II, and the GH10 xylanase, described above.

In another embodiment, the enzyme composition comprises the cellobiohydrolase I, the cellobiohydrolase II, and the beta-xylosidase, described above.

In another embodiment, the enzyme composition comprises the cellobiohydrolase I, the cellobiohydrolase II, the beta-glucosidase or a variant thereof, and the AA9 polypeptide having cellulolytic enhancing activity, described above.

In another embodiment, the enzyme composition comprises the cellobiohydrolase I, the cellobiohydrolase II, the beta-glucosidase or a variant thereof, and the GH10 xylanase, described above.

In another embodiment, the enzyme composition comprises the cellobiohydrolase I, the cellobiohydrolase II, the beta-glucosidase or a variant thereof, and the beta-xylosidase, described above.

In another embodiment, the enzyme composition comprises the cellobiohydrolase I, the cellobiohydrolase II, the AA9 polypeptide having cellulolytic enhancing activity, and the GH10 xylanase, described above.

In another embodiment, the enzyme composition comprises the cellobiohydrolase I, the cellobiohydrolase II, the AA9 polypeptide having cellulolytic enhancing activity, and the beta-xylosidase, described above.

In another embodiment, the enzyme composition comprises the cellobiohydrolase I, the cellobiohydrolase II, the GH10 xylanase, and the beta-xylosidase, described above.

In another embodiment, the enzyme composition comprises the cellobiohydrolase I, the cellobiohydrolase II, the beta-glucosidase or a variant thereof, the AA9 polypeptide having cellulolytic enhancing activity, and the GH10 xylanase, described above.

In another embodiment, the enzyme composition comprises the cellobiohydrolase I, the cellobiohydrolase II, the beta-glucosidase or a variant thereof, the AA9 polypeptide having cellulolytic enhancing activity, and the beta-xylosidase, described above.

In another embodiment, the enzyme composition comprises the cellobiohydrolase I, the cellobiohydrolase II, the beta-glucosidase or a variant thereof, the GH10 xylanase, and the beta-xylosidase, described above.

In another embodiment, the enzyme composition comprises the cellobiohydrolase I, the cellobiohydrolase II, the AA9 polypeptide having cellulolytic enhancing activity, the GH10 xylanase, and the beta-xylosidase, described above.

In another embodiment, the enzyme composition comprises the cellobiohydrolase I, the cellobiohydrolase II, the beta-glucosidase or a variant thereof, the AA9 polypeptide having cellulolytic enhancing activity, the GH10 xylanase, and the beta-xylosidase, described above.

Each of the enzyme compositions described above may further or even further comprise an endoglucanase I, an endoglucanase II, or an endoglucanase I and an endoglucanase II. In one embodiment, the enzyme compositions described above may further or even further comprise an endoglucanase I. In another embodiment, the enzyme compositions described above may further or even further comprise an endoglucanase II. In another embodiment, the enzyme compositions described above may further or even further comprise an endoglucanase I and an endoglucanase II.

In one aspect, the endoglucanase I is selected from the group consisting of: (i) an endoglucanase I comprising or consisting of the mature polypeptide of SEQ ID NO: 16; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15; and (iv) an endoglucanase I encoded by a polynucleotide that hybridizes under at least high stringency conditions, e.g., very high stringency conditions, with the mature polypeptide coding sequence of SEQ ID NO: 15 or the full-length complement thereof.

In another aspect, the endoglucanase II is selected from the group consisting of: (i) an endoglucanase II comprising or consisting of the mature polypeptide of SEQ ID NO: 18; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17; and (iv) an endoglucanase II encoded by a polynucleotide that hybridizes under at least high stringency conditions, e.g., very high stringency conditions, with the mature polypeptide coding sequence of SEQ ID NO: 17 or the full-length complement thereof.

In another aspect, the endoglucanase II is selected from the group consisting of: (i) an endoglucanase II comprising or consisting of the mature polypeptide of SEQ ID NO: 106; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 106; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 105; and (iv) an endoglucanase II encoded by a polynucleotide that hybridizes under at least high stringency conditions, e.g., very high stringency conditions with the mature polypeptide coding sequence of SEQ ID NO: 105 or the full-length complement thereof.

In another aspect, the enzyme composition further or even further comprises a *Trichoderma* endoglucanase I or a homolog thereof. In another aspect, the enzyme composition further comprises a *Trichoderma reesei* endoglucanase I or a homolog thereof. In another aspect, the enzyme composition further comprises a *Trichoderma reesei* Cel7B endoglucanase I (GENBANK™ accession no. M15665) or homolog thereof. In another aspect, the *Trichoderma reesei* endoglucanase I or a homolog thereof is native to the host cell.

In another aspect, the enzyme composition further or even further comprises a *Trichoderma* endoglucanase II or a homolog thereof. In another aspect, the enzyme composition further comprises a *Trichoderma reesei* endoglucanase II or a homolog thereof. In another aspect, the enzyme composition further comprises a *Trichoderma reesei* Cel5A endoglucanase II (GENBANK™ accession no. M19373) or a homolog thereof. In another aspect, the *Trichoderma reesei* endoglucanase II or a homolog thereof is native to the host cell.

Each of the enzyme compositions described above may further or even further comprise a catalase.

In one aspect, the catalase is selected from the group consisting of: (i) a catalase comprising or consisting of the mature polypeptide of SEQ ID NO: 34; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 34; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 33; and (iv) a catalase encoded by a polynucleotide that hybridizes under at least high stringency conditions, e.g., very high stringency conditions, with the mature polypeptide coding sequence of SEQ ID NO: 33 or the full-length complement thereof.

The polynucleotides of SEQ ID NO: 1, 3, 5, 7, 9, 11, 13, 15, 17, 33, and 105, or subsequences thereof, as well as the polypeptides of SEQ ID NO: 2, 4, 6, 8, 10, 12, 14, 16, 18, 34, and 106, or fragments thereof, may be used to design nucleic acid probes to identify and clone DNA encoding enzymes according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library may be screened for DNA that hybridizes with the probes described above and encodes an enzyme. Genomic or other DNA may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 33, or 105, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 33, or 105; (ii) the mature polypeptide coding sequence of SEQ ID NO: 1, 3, 5, 7, 9, 11, 13, 15, 17, 33, or 105; (iii) the genomic DNA or cDNA sequence thereof, as appropriate; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is SEQ ID NO: 1, 3, 5, 7, 9, 11, 13, 15, 17, 33, or 105, or the mature polypeptide coding sequence thereof. In another aspect, the nucleic acid probe is a polynucleotide that encodes the polypeptide of SEQ ID NO: 2, 4, 6, 8, 10, 12, 14, 16, 18, 34, or 106; the mature polypeptide thereof; or a fragment thereof.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applica-*

*tion*, Academic Press, New York. Other nucleic acid amplification procedures such as ligase chain reaction (LCR), ligation activated transcription (LAT) and polynucleotide-based amplification (NASBA) may be used. The polynucleotides may be an allelic or species variant of the polypeptide encoding region of the polynucleotide.

A protein engineered variant of an enzyme above (or protein) may also be used.

In one aspect, the variant is a beta-glucosidase variant. In another aspect, the variant is an *Aspergillus fumigatus* beta-glucosidase variant. In another aspect, the *A. fumigatus* beta-glucosidase variant comprises a substitution at one or more (e.g., several) positions corresponding to positions 100, 283, 456, and 512 of SEQ ID NO: 6, wherein the variant has beta-glucosidase activity.

In an embodiment, the variant has a sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the amino acid sequence of the parent beta-glucosidase.

In another embodiment, the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the mature polypeptide of SEQ ID NO: 6.

For purposes of the present invention, the full-length polypeptide disclosed in SEQ ID NO: 6 is used to determine the corresponding amino acid residue in another beta-glucosidase where methionine is position 1 or the mature polypeptide thereof where the N-terminus is position 20 (Gln). The amino acid sequence of another beta-glucosidase is aligned with the full-length polypeptide disclosed in SEQ ID NO: 6 or the mature polypeptide thereof, and based on the alignment, the amino acid position number corresponding to any amino acid residue in the full-length polypeptide disclosed in SEQ ID NO: 6 or the mature polypeptide thereof is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix.

Identification of the corresponding amino acid residue in another beta-glucosidase can be determined by alignment of multiple polypeptide sequences using several computer programs including, but not limited to, MUSCLE (multiple sequence comparison by log-expectation; version 3.5 or later; Edgar, 2004, *Nucleic Acids Research* 32: 1792-2797), MAFTT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

In one aspect, a variant comprises a substitution at one or more (e.g., several) positions corresponding to positions 100, 283, 456, and 512. In another aspect, a variant comprises a substitution at two positions corresponding to any of positions 100, 283, 456, and 512. In another aspect, a variant comprises a substitution at three positions corresponding to any of positions 100, 283, 456, and 512. In another aspect, a variant comprises a substitution at each position corresponding to positions 100, 283, 456, and 512.

In another aspect, the variant comprises or consists of a substitution at a position corresponding to position 100. In another aspect, the amino acid at a position corresponding to position 100 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution F100D of the full-length polypeptide of SEQ ID NO: 6 or the mature polypeptide thereof.

In another aspect, the variant comprises or consists of a substitution at a position corresponding to position 283. In another aspect, the amino acid at a position corresponding to position 283 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly In another aspect, the variant comprises or consists of the substitution S283G of the full-length polypeptide of SEQ ID NO: 6 or the mature polypeptide thereof.

In another aspect, the variant comprises or consists of a substitution at a position corresponding to position 456. In another aspect, the amino acid at a position corresponding to position 456 is substituted with Ala, Arg, Asn, Asp, Cys, Gin, Glu, Gly, His, Ile, Leu, Lys, Met, Phe, Pro, Ser, Thr, Trp, Tyr, or Val, preferably with Glu. In another aspect, the variant comprises or consists of the substitution N456E of the full-length polypeptide of SEQ ID NO: 6 or the mature polypeptide thereof.

In another aspect, the variant comprises or consists of a substitution at a position corresponding to position 512. In another aspect, the amino acid at a position corresponding to position 512 is substituted with Ala, Arg, Asn, Asp, Cys, Gin, Glu, Gly, His, Ile, Leu, Lys, Met, Phe, Pro, Ser, Thr, Trp, Tyr, or Val, preferably with Tyr. In another aspect, the variant comprises or consists of the substitution F512Y of the full-length polypeptide of SEQ ID NO: 6 or the mature polypeptide thereof.

In another aspect, the variant comprises or consists of a substitution at positions corresponding to positions 100 and 283, such as those described above.

In another aspect, the variant comprises or consists of substitutions at positions corresponding to positions 100 and 456, such as those described above.

In another aspect, the variant comprises or consists of substitutions at positions corresponding to positions 100 and 512, such as those described above.

In another aspect, the variant comprises or consists of substitutions at positions corresponding to positions 283 and 456, such as those described above.

In another aspect, the variant comprises or consists of substitutions at positions corresponding to positions 283 and 512, such as those described above.

In another aspect, the variant comprises or consists of substitutions at positions corresponding to positions 456 and 512, such as those described above.

In another aspect, the variant comprises or consists of substitutions at positions corresponding to positions 100, 283, and 456, such as those described above.

In another aspect, the variant comprises or consists of substitutions at positions corresponding to positions 100, 283, and 512, such as those described above.

In another aspect, the variant comprises or consists of substitutions at positions corresponding to positions 100, 456, and 512, such as those described above.

In another aspect, the variant comprises or consists of substitutions at positions corresponding to positions 283, 456, and 512, such as those described above.

In another aspect, the variant comprises or consists of substitutions at positions corresponding to positions 100, 283, 456, and 512, such as those described above.

In another aspect, the variant comprises or consists of one or more (e.g., several) substitutions selected from the group consisting of F100D, S283G, N456E, and F512Y.

In another aspect, the variant comprises or consists of the substitutions F100D+S283G of the full-length polypeptide of SEQ ID NO: 6 or the mature polypeptide thereof.

In another aspect, the variant comprises or consists of the substitutions F100D+N456E of the full-length polypeptide of SEQ ID NO: 6 or the mature polypeptide thereof.

In another aspect, the variant comprises or consists of the substitutions F100D+F512Y of the full-length polypeptide of SEQ ID NO: 6 or the mature polypeptide thereof.

In another aspect, the variant comprises or consists of the substitutions S283G+N456E of the full-length polypeptide of SEQ ID NO: 6 or the mature polypeptide thereof.

In another aspect, the variant comprises or consists of the substitutions S283G+F512Y of the full-length polypeptide of SEQ ID NO: 6 or the mature polypeptide thereof.

In another aspect, the variant comprises or consists of the substitutions N456E+F512Y of the full-length polypeptide of SEQ ID NO: 6 or the mature polypeptide thereof.

In another aspect, the variant comprises or consists of the substitutions F100D+S283G+N456E of the full-length polypeptide of SEQ ID NO: 6 or the mature polypeptide thereof.

In another aspect, the variant comprises or consists of the substitutions F100D+S283G+F512Y of the full-length polypeptide of SEQ ID NO: 6 or the mature polypeptide thereof.

In another aspect, the variant comprises or consists of the substitutions F100D+N456E+F512Y of the full-length polypeptide of SEQ ID NO: 6 or the mature polypeptide thereof.

In another aspect, the variant comprises or consists of the substitutions S283G+N456E+F512Y of the full-length polypeptide of SEQ ID NO: 6 or the mature polypeptide thereof.

In another aspect, the variant comprises or consists of the substitutions F100D+S283G+N456E+F512Y of the full-length polypeptide of SEQ ID NO: 6 or the mature polypeptide thereof.

The variants may consist of 720 to 863 amino acids, e.g., 720 to 739, 740 to 759, 760 to 779, 780 to 799, 800 to 819, 820 to 839, and 840 to 863 amino acids.

In one aspect, a variant beta-glucosidase comprises or consists of the mature polypeptide of SEQ ID NO: 36.

The variants may further comprise an alteration at one or more (e.g., several) other positions.

In one embodiment, the amount of cellobiohydrolase I in an enzyme composition of the present invention is 5% to 60% of the total protein of the enzyme composition, e.g., 7.5% to 55%, 10% to 50%, 12.5% to 45%, 15% to 40%, 17.5% to 35%, and 20% to 30% of the total protein of the enzyme composition.

In another embodiment, the amount of cellobiohydrolase II in an enzyme composition of the present invention is 2.0-40% of the total protein of the enzyme composition, e.g., 3.0% to 35%, 4.0% to 30%, 5% to 25%, 6% to 20%, 7% to 15%, 7.5% to 12%, 10% to 20%, and 11 to 17% of the total protein of the enzyme composition.

In another embodiment, the amount of beta-glucosidase in an enzyme composition of the present invention is 0% to 30% of the total protein of the enzyme composition, e.g., 1% to 27.5%, 1.5% to 25%, 2% to 22.5%, 3% to 20%, 4% to 19%, % 4.5 to 18%, 5% to 17%, and 6% to 16% of the total protein of the enzyme composition.

In another embodiment, the amount of AA9 polypeptide in an enzyme composition of the present invention is 0% to 50% of the total protein of the enzyme composition, e.g., 2.5% to 45%, 5% to 40%, 7.5% to 35%, 10% to 30%, 10% to 25%, 12.5% to 25%, and 15% to 25% of the total protein of the enzyme composition.

In another embodiment, the amount of xylanase in an enzyme composition of the present invention is 0% to 30% of the total protein of the enzyme composition, e.g., 0.125% to 30%, 0.25% to 25%, 0.5% to 30%, 1.0% to 27.5%, 1.5% to 25%, 2% to 22.5%, 0.5% to 20%, 2.5% to 20%, 3% to 19%, 3.5% to 18%, 4% to 17%, 0.75% to 15%, and 1% to 10% of the total protein of the enzyme composition.

In another embodiment, the amount of beta-xylosidase in an enzyme composition of the present invention is 0% to 50% of the total protein of the enzyme composition, e.g., 0.125% to 30%, 0.25% to 25%, 0.75% to 17.5%, 0.5% to 30%, 1.0% to 27.5%, 1.5% to 25%, 2% to 22.5%, 0.5% to 20%, 2.5% to 20%, 3% to 19%, 3.5% to 18%, 4% to 17%, and 1% to 15% of the total protein of the enzyme composition.

In another embodiment, the amount of endoglucanase I in an enzyme composition of the present invention is 0.5% to 30% of the total protein of the enzyme composition, e.g., 1.0% to 25%, 2% to 20%, 4% to 25%, 5% to 20%, 16% to 15%, and 7% to 12% of the total protein of the enzyme composition.

In another embodiment, the amount of endoglucanase II in an enzyme composition of the present invention is 0.5% to 30% of the total protein of the enzyme composition, e.g., 1.0% to 25%, 2% to 20%, 4% to 25%, 5% to 20%, 16% to 15%, and 7% to 12% of the total protein of the enzyme composition.

In another embodiment, the amount of catalase in an enzyme composition of the present invention is 0% to 25% of the total protein of the enzyme composition, e.g., 0.25% to 20%, 0.5% to 15%, 0.75% to 10%, 1% to 9.5%, 1.25% to 9%, 1.5% to 8%, 1.75% to 8%, 1.75% to 7%, and 1.75% to 6% of the total protein of the enzyme composition.

The amount of protein can be determined as described in Example 17.

The enzyme composition may further or even further comprise one or more (e.g., several) enzymes selected from the group consisting of a cellulase, an AA9 polypeptide having cellulolytic enhancing activity, a cellulose inducible protein (GENESEQP:ADW12302), a hemicellulase, an esterase, an expansin, a laccase, a ligninolytic enzyme, a pectinase, a catalase, a peroxidase, a protease, and a swollenin (GENESEQP:BBA42745). In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a beta-glucanase, a coumaric acid esterase, a feruloyl esterase, a galactosidase, a glucuronidase, a glucuronoyl esterase, a mannanase, a mannosidase, a xylanase, and a xylosidase. The sources for the above enzymes may be fungal or bacterial, and may be present as single domain enzymes or polypeptides comprising multiple catalytic domains.

One or more (e.g., several) of the enzymes in the enzyme composition may be wild-type proteins expressed by the host strain, recombinant proteins, or a combination of wild-type proteins expressed by the host strain and recombinant proteins. For example, one or more (e.g., several) enzymes may be native proteins of a cell, which is used as a host cell to express recombinantly the enzyme composition.

In another aspect, the enzyme compositions can further comprise a whole broth preparation of a *Trichoderma* strain. In another aspect, the enzyme compositions can further comprise a whole broth preparation of a *Trichoderma reesei* strain.

In another aspect, the enzyme compositions can further comprise a whole broth preparation of a *Talaromyces emersonii* strain.

In another aspect, the enzyme compositions can further comprise a whole broth preparation of a *Myceliophthora* strain. In another aspect, the enzyme compositions can further comprise a whole broth preparation of a *Myceliophthora thermophila* strain.

In another aspect, the enzyme compositions can further comprise a combination of two or more of a *Trichoderma* whole broth preparation (e.g., a *Trichoderma reesei* whole broth preparation); a *Myceliophthora* whole broth preparation (e.g., a *Myceliophthora thermophila* whole broth preparation); and a *Talaromyces emersonii* whole broth preparation.

The enzyme compositions may be prepared in accordance with methods known in the art and may be in the form of a liquid or a dry composition. The compositions may be stabilized in accordance with methods known in the art.

The enzyme compositions may result from a single fermentation or may be a blend of two or more fermentations, e.g., three, four, five, six, seven, etc. fermentations. For example, one fermentation may produce cellulases (e.g., endoglucanases, cellobiohydrolases, beta-glucosidase) and a second fermentation may produce hemicellulases (e.g., xylanase and beta-xylosidase), which are then blended in a specific ratio, e.g., 10/90 v/v, 25/75 v/v, 50:50 v/v, 75:25 v/v, or 90/10 v/v, respectively, to produce an enzyme composition. In another example, one fermentation may produce cellulases (e.g., endoglucanases, cellobiohydrolases, beta-glucosidase), a second fermentation may produce hemicellulases (e.g., xylanase and beta-xylosidase), and a third fermentation may produce an AA9 (GH61) polypeptide, which are then blended in a specific ratio, e.g., 10:80:20 v/v/v, 20:60:20 v/v/v, 40:40:20 v/v/v, 40:20:40 v/v/v, or 50:10:40 v/v/v, respectively, to produce an enzyme composition.

The enzyme compositions may be in any form suitable for use, such as, for example, a crude fermentation broth with or without cells removed, a cell lysate with or without cellular debris, a semi-purified or purified enzyme preparation, or a host cell (e.g., *T. reesei*, *T. emersonii*, or *M. thermophila*) as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The enzyme compositions may also be a fermentation broth formulation or a cell composition. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains live cells, killed cells and/or cell debris. In one embodiment, the composition comprises live cells. In another embodiment, killed cells, and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid slurry, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by the method described in WO 90/15861 or WO 2010/096673.

The effective amount of an enzyme composition of the present invention in deconstructing a cellulosic or hemicellulosic material depends on several factors including, but not limited to, the cellulosic or hemicellulosic material, the concentration of cellulosic or hemicellulosic material, the pretreatment(s) of the cellulosic or hemicellulosic material, temperature, time, pH, and inclusion of fermenting organism (e.g., yeast for Simultaneous Saccharification and Fermentation).

In one aspect, an effective amount of an enzyme composition of the present invention to the cellulosic or hemicellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg protein per g of the cellulosic or hemicellulosic material.

The enzyme compositions of the present invention are more efficient at high temperatures in the deconstruction of cellulosic or hemicellulosic material. The enzyme compositions of the present invention enable efficient conversion of cellulosic or hemicellulosic material at significantly lower dosages relative to a commercial benchmark cocktail. For example, 75% conversion of glucan was achieved at 5 mg enzyme protein per g cellulose while equivalent conversion with the benchmark cocktail required approximately 14 mg enzyme protein per g cellulose (see FIG. 12).

Nucleic Acid Constructs

Nucleic acid constructs comprising a polynucleotide encoding an enzyme or protein can be constructed by operably linking one or more (e.g., several) control sequences to the polynucleotide to direct the expression of the coding sequence in a fungal host cell under conditions compatible with the control sequences. Manipulation of the polynucleotide prior to its insertion into a vector may be desirable or necessary depending on the expression vector. The techniques for modifying polynucleotides utilizing recombinant DNA methods are well known in the art. The nucleic acid constructs may comprise one or more polynucleotides encoding an enzyme component or enzyme components of the compositions.

The control sequence may be a promoter, a polynucleotide that is recognized by a fungal host cell for expression of a polynucleotide encoding an enzyme or protein. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147, which is incorporated herein in its entirety.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a fungal host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a leader, a nontranslated region of an mRNA that is important for translation by a fungal host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by a fungal host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, *Fusarium oxysporum* trypsin-like protease, *Trichoderma reesei* cellobiohydrolase I, *Trichoderma reesei* cellobiohydrolase II, and *Trichoderma reesei* endoglucanase V.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, and *Trichoderma reesei* endoglucanase V.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of a fungal host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

Recombinant expression vectors can be constructed comprising a polynucleotide encoding an enzyme, a promoter, a terminator, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vectors may comprise one or more polynucleotides encoding an enzyme component or enzyme components of the compositions.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hpt (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are the adeA, adeB, amdS, hpt, and pyrG genes. Suitable markers for yeast host cells include, but are not limited to, ADE2, HIS3, LEU2, LYS2, MET3, TRP1, and URA3.

The selectable marker may be a dual selectable marker system as described in WO 2010/039889, which is incorporated herein by reference in its entirety. In one aspect, the dual selectable marker is an hpt-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in a fungal host cell. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal host cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

Examples of origins of replication for use in a yeast host cell are the 2 micron origin of replication, ARS1, ARS4, the combination of ARS1 and CEN3, and the combination of ARS4 and CEN6.

More than one copy of a polynucleotide may be inserted into a fungal host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, *Molecular Cloning, A Laboratory Manual*, 2d edition, Cold Spring Harbor, N.Y.).

Host Cells

The present invention also relates to recombinant fungal host cells, comprising polynucleotides encoding an enzyme composition comprising: (A) (i) a cellobiohydrolase I, (ii) a cellobiohydrolase II, and (iii) at least one enzyme selected from the group consisting of a beta-glucosidase or a variant thereof, an AA9 polypeptide having cellulolytic enhancing activity, a GH10 xylanase, and a beta-xylosidase; (B) (i) a GH10 xylanase and (ii) a beta-xylosidase; or (C) (i) a cellobiohydrolase I, (ii) a cellobiohydrolase II, (iii) a GH10 xylanase, and (iv) a beta-xylosidase, as described herein. The recombinant fungal host cells may further or even further comprise one or more polynucleotides encoding an endoglucanase I, an endoglucanase II, or an endoglucanase I and an endoglucanase II, as described herein. The recombinant fungal host cells may further or even further comprise a polynucleotide encoding a catalase, as described herein.

The recombinant fungal host cells can further comprise one or more polynucleotides encoding enzymes selected from the group consisting of a cellulase, an AA9 polypeptide having cellulolytic enhancing activity, a cellulose inducible protein, a hemicellulase, an esterase, an expansin, a laccase, a ligninolytic enzyme, a pectinase, a catalase, a peroxidase, a protease, and a swollenin, as described herein. One or more (e.g., several) of the enzymes may be wild-type proteins, recombinant proteins, or a combination of wild-type proteins and recombinant proteins.

The host cell may be any fungal cell useful in the recombinant production of an enzyme or protein. The term "host cell" encompasses any progeny of a parent cell that is not identical to the parent cell due to mutations that occur during replication.

"Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities* of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed with one or more constructs and/or vectors described herein by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Suitable procedures for transformation of Myceliophthora thermophila are described in WO 2000/020555. Suitable procedures for transformation of Talaromyces emersonii are described in WO 2011/054899 and Jain et al., 1992, Mol. Gen. Genet. 234: 489. Yeast may be transformed using the procedures described by Becker and Guarente, In Abelson, J. N. and Simon, M.I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

In one aspect, the filamentous fungal cell is any Trichoderma cell useful in the recombinant production of an enzyme or protein. For example, the Trichoderma cell may be a Trichoderma harzianum, Trichoderma koningii, Trichoderma longibrachiatum, Trichoderma reesei, or Trichoderma viride cell. In another aspect, the Trichoderma cell is a Trichoderma harzianum cell. In another aspect, the Trichoderma cell is a Trichoderma koningii cell. In another aspect, the Trichoderma cell is a Trichoderma longibrachiatum cell. In another aspect, the Trichoderma cell is a Trichoderma reesei cell. In another aspect, the Trichoderma cell is a Trichoderma viride cell.

In another aspect, the Trichoderma reesei cell is Trichoderma reesei RutC30. In another aspect, the Trichoderma reesei cell is Trichoderma reesei TV10. In another aspect, the Trichoderma reesei cell is a mutant of Trichoderma reesei RutC30. In another aspect, the Trichoderma reesei cell is mutant of Trichoderma reesei TV10. In another aspect, the Trichoderma reesei cell is a morphological mutant of Trichoderma reesei. See, for example, WO 97/26330, which is incorporated herein by reference in its entirety.

In another aspect, the filamentous fungal cell is any Aspergillus oryzae cell useful in the recombinant production of an enzyme or protein.

In another aspect, the filamentous fungal cell is any Aspergillus niger cell useful in the recombinant production of an enzyme or protein.

In another aspect, the filamentous fungal cell is any Myceliophthora thermophila cell useful in the recombinant production of an enzyme or protein.

In another aspect, the filamentous fungal cell is any Talaromyces emersonii cell useful in the recombinant production of an enzyme or protein.

One or more (e.g., several) native cellulase and/or hemicellulase genes may be inactivated in the filamentous fungal host cell (e.g., Trichoderma) by disrupting or deleting the genes, or a portion thereof, which results in the mutant cell producing less or none of the cellulase and/or hemicellulase than the parent cell when cultivated under the same conditions. In one aspect, the one or more (e.g., several) cellulase genes encode enzymes selected from the group consisting of cellobiohydrolase I, cellobiohydrolase II, endoglucanase I, endoglucanase II, beta-glucosidase, and swollenin. In another aspect, the one or more (e.g., several) hemicellulase genes encode enzymes selected from the group consisting of xylanase I, xylanase II, xylanase III, and beta-xylosidase. In another aspect, the one or more (e.g., several) hemicellulase genes encode enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, and a mannosidase.

The mutant cell may be constructed by reducing or eliminating expression of a polynucleotide encoding a cellulase or hemicellulase using methods well known in the art, for example, insertions, disruptions, replacements, or deletions. In a preferred aspect, the polynucleotide is inactivated.

The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more (e.g., several) nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

Modification or inactivation of the polynucleotide may also be accomplished by inhibiting expression of an enzyme encoded by the polynucleotide in a cell by administering to the cell or expressing in the cell a double-stranded RNA (dsRNA) molecule, wherein the dsRNA comprises a subsequence of a polynucleotide encoding the enzyme. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation. In another aspect, the double-stranded RNA (dsRNA) molecules comprise a portion of the mature polypeptide coding sequence of SEQ ID NO: 19, SEQ ID NO: 21, SEQ ID NO: 23, SEQ ID NO: 25, SEQ ID NO: 27, SEQ ID NO: 29, and/or SEQ ID NO: 31 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs can be used in gene-silencing to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

In one aspect, a gene encoding a cellobiohydrolase I is inactivated. In another aspect, a gene encoding a *Trichoderma* cellobiohydrolase I is inactivated. In another aspect, a gene encoding a *Trichoderma reesei* cellobiohydrolase I is inactivated. In another aspect, the cellobiohydrolase I is selected from the group consisting of: (i) a cellobiohydrolase I comprising or consisting of the mature polypeptide of SEQ ID NO: 20; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 19; and (iv) a cellobiohydrolase I encoded by a polynucleotide that hybridizes under at least high stringency conditions, e.g., very high stringency conditions, with the mature polypeptide coding sequence of SEQ ID NO: 19 or the full-length complement thereof.

In another aspect, a gene encoding a cellobiohydrolase II is inactivated. In another aspect, a gene encoding a *Trichoderma* cellobiohydrolase II is inactivated. In another aspect, a gene encoding a *Trichoderma reesei* cellobiohydrolase II is inactivated. In another aspect, the cellobiohydrolase II is selected from the group consisting of: (i) a cellobiohydrolase II comprising or consisting of the mature polypeptide of SEQ ID NO: 22; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 21; and (iv) a cellobiohydrolase II encoded by a polynucleotide that hybridizes under at least high stringency conditions, e.g., very high stringency conditions, with the mature polypeptide coding sequence of SEQ ID NO: 21 or the full-length complement thereof.

In another aspect, a gene encoding a beta-glucosidase is inactivated. In another aspect, a gene encoding a *Trichoderma* beta-glucosidase is inactivated. In another aspect, a gene encoding a *Trichoderma reesei* beta-glucosidase is inactivated. In another aspect, the beta-glucosidase is selected from the group consisting of: (i) a beta-glucosidase comprising or consisting of the mature polypeptide of SEQ ID NO: 24; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a beta-glucosidase encoded by a polynucleotide that hybridizes under at least high stringency conditions, e.g., very high stringency conditions, with the mature polypeptide coding sequence of SEQ ID NO: 23 or the full-length complement thereof.

In another aspect, a gene encoding a xylanase is inactivated. In another aspect, a gene encoding a *Trichoderma* xylanase is inactivated. In another aspect, a gene encoding a *Trichoderma reesei* xylanase is inactivated. In another aspect, the xylanase is selected from the group consisting of: (i) a xylanase comprising or consisting of the mature polypeptide of SEQ ID NO: 26, SEQ ID NO: 28, or SEQ ID NO: 30; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26, SEQ ID NO: 28, or SEQ ID NO: 30; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25, SEQ ID NO: 27, or SEQ ID NO: 29; and (iv) a xylanase encoded by a polynucleotide that hybridizes under at least high stringency conditions, e.g., very high stringency conditions, with the mature polypeptide coding sequence of SEQ ID NO: 25, SEQ ID NO: 27, or SEQ ID NO: 29; or the full-length complement thereof.

In another aspect, a gene encoding a beta-xylosidase is inactivated. In another aspect, a gene encoding a *Trichoderma* beta-xylosidase is inactivated. In another aspect, a gene encoding a *Trichoderma reesei* beta-xylosidase is inactivated. In another aspect, the beta-xylosidase is selected from the group consisting of: (i) a beta-xylosidase comprising or consisting of the mature polypeptide of SEQ ID NO: 32; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 32; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 31; and (iv) a beta-xylosidase encoded by a polynucleotide that hybridizes under at least high stringency conditions, e.g., very high stringency conditions, with the mature polypeptide coding sequence of SEQ ID NO: 31 or the full-length complement thereof.

In another aspect, a cellobiohydrolase I gene is inactivated. In another aspect, a *Trichoderma* cellobiohydrolase I gene is inactivated. In another aspect, a *Trichoderma reesei* cellobiohydrolase I gene is inactivated. In another aspect, a *Trichoderma* cellobiohydrolase II gene is inactivated. In another aspect, a *Trichoderma reesei* cellobiohydrolase II gene is inactivated. In another aspect, a *Trichoderma* beta-glucosidase gene is inactivated. In another aspect, a *Trichoderma reesei* beta-glucosidase gene is inactivated. In another aspect, a *Trichoderma* xylanase gene is inactivated. In another aspect, a *Trichoderma reesei* xylanase gene is inactivated. In another aspect, a *Trichoderma* beta-xylosidase gene is inactivated. In another aspect, a *Trichoderma reesei* beta-xylosidase gene is inactivated.

In another aspect, a *Trichoderma* cellobiohydrolase I gene and a *Trichoderma* cellobiohydrolase II gene are inactivated. In another aspect, a *Trichoderma reesei* cellobiohydrolase I gene and a *Trichoderma reesei* cellobiohydrolase II gene are inactivated.

In another aspect, two or more (e.g., several) genes selected from the group consisting of cellobiohydrolase I, cellobiohydrolase II, beta-glucosidase, xylanase I, xylanase II, xylanase III, and beta-xylosidase are inactivated. In another aspect, three or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, four or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, five or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, six or more (e.g., several) genes selected from the group consisting of cellobiohydrolase I, cellobiohydrolase II, beta-glucosidase, xylanase I, xylanase II, xylanase III, and beta-xylosidase genes are inactivated.

In another aspect, the cellobiohydrolase I, cellobiohydrolase II, beta-glucosidase, xylanase I, xylanase II, xylanase III, and beta-xylosidase genes are inactivated.

In another aspect, one or more (e.g., several) protease genes are inactivated. In another aspect, the one or more (e.g., several) protease genes are subtilisin-like serine protease, aspartic protease, and trypsin-like serine protease genes as described in WO 2011/075677, which is incorporated herein by reference in its entirety.

Processes of Production

The present invention also relates to processes of producing an enzyme composition of the present invention described herein, comprising: (a) cultivating one or more (e.g., several) fungal host cells of the present invention under conditions conducive for production of the enzyme composition; and optionally (b) recovering the enzyme composition.

The fungal host cells are cultivated in a nutrient medium suitable for production of the enzyme composition using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the enzymes to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The activity of the enzyme compositions may be determined using methods known in the art. These methods include, but are not limited to, use of specific antibodies, formation of an enzyme product, or disappearance of an enzyme substrate.

The enzyme compositions may be recovered using methods known in the art. For example, the enzyme may be recovered from the nutrient medium by conventional procedures including, but not limited to, collection, centrifugation, filtration, extraction, spray-drying, evaporation, or precipitation. In one aspect, the whole fermentation broth is recovered.

Uses

The present invention is also directed to the following processes for using the enzyme compositions of the present invention.

The present invention also relates to processes for degrading a cellulosic or hemicellulosic material, comprising: treating the cellulosic or hemicellulosic material with an enzyme composition of the present invention. In one aspect, the processes further comprise recovering the degraded cellulosic or hemicellulosic material. Soluble products from the degradation of the cellulosic or hemicellulosic material can be separated from insoluble cellulosic or hemicellulosic material using methods known in the art such as, for example, centrifugation, filtration, or gravity settling.

The present invention also relates to processes of producing a fermentation product, comprising: (a) saccharifying a cellulosic or hemicellulosic material with an enzyme composition of the present invention; (b) fermenting the saccharified cellulosic or hemicellulosic material with one or more (e.g., several) fermenting microorganisms to produce the fermentation product; and (c) recovering the fermentation product from the fermentation.

The present invention also relates to processes of fermenting a cellulosic or hemicellulosic material, comprising: fermenting the cellulosic or hemicellulosic material with one or more (e.g., several) fermenting microorganisms, wherein the cellulosic or hemicellulosic material is saccharified with an enzyme composition of the present invention. In one aspect, the fermenting of the cellulosic or hemicellulosic material produces a fermentation product. In another aspect, the processes further comprise recovering the fermentation product from the fermentation.

The processes of the present invention can be used to saccharify the cellulosic or hemicellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic or hemicellulosic material typically involves pretreatment, enzymatic hydrolysis (saccharification), and fermentation.

The processing of the cellulosic or hemicellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic or hemicellulosic material to fermentable sugars, e.g., glucose, cellobiose, and pentose monomers, and then ferment the fermentable sugars to ethanol. In SSF, the enzymatic hydrolysis of the cellulosic or hemicellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic or hemicellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic or hemicellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic or hemicellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or hemicellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or hemicellulosic material is heated to disrupt the plant cell wall components, including lignin, hemicellulose, and cellulose to make the cellulose and other fractions, e.g., hemicellulose, accessible to enzymes. The cellulosic or hemicellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic or hemicellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or hemicellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic or hemicellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic or hemicellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic or hemicellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or hemicellulosic material is present during pretreatment in amounts preferably between 10-80 wt. %, e.g., 20-70 wt. % or 30-60 wt. %, such as around 40 wt. %. The pretreated cellulosic or hemicellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or hemicellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or hemicellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic or hemicellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification. In the hydrolysis step, also known as saccharification, the cellulosic or hemicellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by one or more enzyme compositions of the present invention in one or more stages. The hydrolysis can be carried out as a batch process or series of batch processes. The hydrolysis can be carried out as a fed batch or continuous process, or series of fed batch or continuous processes, where the cellulosic or hemicellulosic material is fed gradually to, for example, an enzyme containing hydrolysis solution.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s).

The saccharification is generally performed in stirred-tank reactors or fermentors under controlled pH, temperature, and mixing conditions. Suitable process time, temperature and pH conditions can readily be determined by one skilled in the art. For example, the total saccharification time can last up to 200 hours, but is typically performed for preferably about 4 to about 120 hours, e.g., about 12 to about 96 hours or about 24 to about 72 hours. The temperature is in the range of preferably about 25° C. to about 80° C., e.g., about 30° C. to about 70° C., about 40° C. to about 60° C., or about 50° C. to about 55° C. The pH is in the range of preferably about 3 to about 9, e.g., about 3.5 to about 8, about 4 to about 7, about 4.2 to about 6, or about 4.3 to about 5.5.

The dry solids content is in the range of preferably about 5 to about 50 wt. %, e.g., about 10 to about 40 wt. % or about 20 to about 30 wt. %.

In one aspect, the saccharification is performed in the presence of dissolved oxygen at a concentration of at least 0.5% of the saturation level.

In an embodiment of the invention, the dissolved oxygen concentration during saccharification is in the range of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level. In a preferred embodiment, the dissolved oxygen concentration is maintained at a concentration of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level during at least 25% of the saccharification period, such as at least 50% or at least 75% of the saccharification period. When the enzyme composition comprises an oxidoreductase the dissolved oxygen concentration may be higher up to 70% of the saturation level.

Oxygen is added to the vessel in order to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, MO, USA.

In the processes of the present invention, an enzyme composition of the present invention can be added prior to or during fermentation, e.g., during saccharification or during or after propagation of the fermenting microorganism(s).

Fermentation. The fermentable sugars obtained from the hydrolyzed cellulosic or hemicellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or hemicellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic or hemicellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Xylose fermenting yeast include strains of *Candida,* preferably *C. sheatae* or *C. sonorensis;* and strains of *Pichia,* e.g., *P. stipitis,* such as *P. stipitis* CBS 5773. Pentose fermenting yeast include strains of *Pachysolen,* preferably *P. tannophilus.* Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, G. P., 1996, Cellulose bioconversion technology, in *Handbook on Bioethanol: Production and Utilization,* Wyman, C. E., ed., Taylor & Francis, Washington, D.C., 179-212).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum;* and *Zymomonas,* such as *Zymomonas mobilis.*

Commercially available yeast suitable for ethanol production include, e.g., BIO-FERM® AFT and XR (Lallemand Specialities, Inc., USA), ETHANOL RED® yeast (Lesaffre et Compagnie, France), FALI® (AB Mauri Food Inc., USA), FERMIOL® (Rymco International AG, Denmark), GERT STRAND™ (Gert Strand AB, Sweden), and SUPER-START™ and THERMOSACC® fresh yeast (Lallemand Specialities, Inc., USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises one or more polynucleotides encoding one or more cellulolytic enzymes, hemicellulolytic enzymes, and accessory enzymes.

It is well known in the art that the organisms described above can also be used to produce other substances, as described herein.

The fermenting microorganism is typically added to the degraded cellulosic or hemicellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or hemicellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, or xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36 (6-7): 41-47; and Gunaseelan, 1997, *Biomass and Bioenergy* 13 (1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or hemicellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Strains

*Trichoderma reesei* RutC30 is a mutagenized *T. reesei* strain of original isolate QM6A (Montenecourt and Eveleigh, 1979, *Adv. Chem. Ser.* 181: 289-301).

*T. reesei* strain 981-O8-D4 is a mutagenized strain of *T. reesei* RutC30.

*T. reesei* AgJg115-104-7B1 is strain *T. reesei* 981-08-D4 strain containing a disruption of ku70 rendering it deficient in non-homologous end joining of DNA (WO 2011/075677).
Media and Buffer Solutions Cellulase inducing medium (CIM) was composed of 20 g of Arbocel-natural cellulose fibers (J. Rettenmaier USA LP), 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *T. reesei* trace metals solution, 2 drops of anti-foam, and deionized water to 1 liter; pH 6.0.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g or 1 g of $MnSO_4.H_2O$, 0.8 g of $Na_2MoO_2.2H_2O$, 10 g of $ZnSO_4.7H_2O$, and deionized water to 1 liter.

LB+Amp medium was composed of 10 g of tryptone, 5 g of yeast extract, 5 g of NaCl, and deionized water to 1 liter. After autoclaving 1 ml of a 100 mg/ml solution of ampicillin in water was added.

Overlay PDA medium was composed of 39 g of Potato Dextrose Agar (Difco) and deionized water to 1 liter.

PDA plates were composed of 39 g of Potato Dextrose Agar (Difco) and deionized water to 1 liter.

PEG buffer was composed of 500 g of PEG 4000, 10 mM $CaCl_2$, 10 mM Tris-HCl pH 7.5, and deionized water to 1 liter; filter sterilized.

SOC medium was composed of 20 g of tryptone, 5 g of yeast extract, 0.5 g of NaCl, 10 ml of 250 mM KCl, and deionized water to 1 liter.

STC was composed of 0.8 M or 1 M sorbitol, 10 mM or 25 mM $CaCl_2$, and 10 mM Tris-HCl, pH 7.5; filter sterilized.

TAE buffer was composed of 4.84 g of Tris Base, 1.14 ml of Glacial acetic acid, 2 ml of 0.5 M EDTA pH 8, and deionized water to 1 liter.

TBE buffer was composed of 10.8 g of Tris Base, 5 g of boric acid, 4 ml of 0.5 M EDTA pH 8, and deionized water to 1 liter.

TE buffer was composed of 1 M Tris pH 8.0 and 0.5 M EDTA pH 8.0 in deionized water.

TrMM-G plates were composed of 20 ml of COVE salt solution, 6 g of $(NH_4)_2SO_4$, 0.6 g of $CaCl_2$, 25 g of Nobel Agar (Difco), 20 g of glucose, and deionized water to 1 liter.

*T. reesei* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_4$, 336 g of citric acid, and deionized water to 1 liter.

2XYT+Amp plates were composed of 10 g of tryptone, 5 g of yeast extract, 5 g of sodium chloride, 15 g of Bacto Agar, and deionized water to 1 liter, followed by 2 ml of a filter-sterilized solution of 50 mg/ml ampicillin after autoclaving.

YP medium was composed of 10 g of yeast extract, 20 g of Bacto peptone, and deionized water to 1 liter.

Example 1

Protoplast Generation and Transformation of *Trichoderma reesei* Strain AgJg115-104-7B1 to Delete the *T. reesei* 42 kDa Aspartic Protease Protoplast preparation and transformation were performed using a modified protocol of Penttila et al., 1987, *Gene* 61: 155-164. Briefly, *Trichoderma reesei* strain AgJg115-104-7B1 was cultivated in 25 ml of YP medium supplemented with 2% (w/v) glucose and 10 mM uridine at 27° C. for 17 hours with gentle agitation at 90 rpm. Mycelia were collected by filtration using a Millipore Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a hemocytometer and re-suspended to a final concentration of $1 \times 10^8$ protoplasts/ml in STC. Excess protoplasts were stored in cryotubes and frozen in a Cryo 1° C. Freezing Container (Nalgene, Rochester, N.Y., USA) at −80° C.

A deletion construct pAgJg118 (WO 2011/075677) contains the *E. coli* hygromycin phosphotransferase (hpt) gene and the Herpes simplex virus thymidine kinase (tk) gene flanked by direct repeats. The direct repeats were inserted to facilitate the excision of the hpt and tk selectable markers and generate a clean deletion of a 42 kDa aspartic protease gene. Ninety-six μg of the transforming plasmid, pAgJg118, were digested with Pme I. The digestion reaction was purified by 1% agarose gel electrophoresis using TAE buffer where a 7.9 kb DNA band was excised from the gel, and extracted using a QIAQUICK® Gel Extraction Kit (QIAGEN Inc., Valencia, Calif., USA). Briefly 3 volumes of Kit-supplied buffer QG were added to the gel slice and dissolved at 50° C. for approximately 10 minutes. The dissolved gel slice was applied to a Kit-supplied spin column by transferring to the column and centrifuging at 13,000 rpm for 1 minute. The column was washed with 750 μl of Kit-supplied buffer PE and the centrifugation was repeated. DNA was eluted with 25 μl of Kit-supplied buffer EB. Approximately 1 μg of the resulting purified DNA fragment was added to 100 μl of the protoplast solution and mixed gently. PEG buffer (250 μl) was added, mixed, and incubated at 34° C. for 30 minutes. STC (3 ml) was then added, mixed, and spread onto PDA plates supplemented with 1 M sucrose. After incubation at 28° C. for 16 hours, 20 ml of overlay PDA medium supplemented with 35 µg of hygromycin B per ml were added to each plate. The plates were incubated at 28° C. for 4-7 days. Seven transformants were sub-cultured onto PDA plates to generate spores.

Transformants of *T. reesei* strain AgJg115-104-7B1 containing the pAgJg118 deletion vector at the 42 kDa aspartic protease locus were screened by Fungal Colony PCR. A small amount of spores from each transformant was suspended in 20 µl of Dilution buffer (PHIRE® Plant Direct PCR Kit, Thermo Fisher Scientific, Waltham, Mass., USA). The spore suspension was used as a template in a PCR reaction to screen for the aspartic protease deletion. The reaction was composed of 0.5 µl of the spore suspension, 50 µmol of primer 069134 (shown below), 50 µmol of primer 067947 (shown below), 10 µl of 2×PHIRE® Plant PCR Buffer (PHIRE® Plant Direct PCR Kit, Thermo Fisher Scientific), and 0.4 µl of PHIRE® Hot Start II DNA Polymerase (PHIRE® Plant Direct PCR Kit, Thermo Fisher Scientific) in a 20 µl reaction. The reaction was incubated in an EPPENDORF® MASTERCYCLER® (Eppendorf Scientific, Inc., Westbury, N.Y., USA) programmed for 1 cycle at 98° C. for 5 minutes; 40 cycles each at 98° C. for 5 seconds, 58° C. for 5 seconds, and 72° C. for 2 minutes 20 seconds; 1 cycle at 72° C. for 2 minutes; and a 10° C. hold. Primer 069134 is located upstream of the 5' flanking region and primer 067947 is located at the beginning of the *E. coli* hygromycin phosphotransferase (hpt) gene coding region. If the deletion vector was integrated into the aspartic protease locus, the amplified PCR fragment should be 2.4 kb in length. One transformant designated *T. reesei* AgJg115-118-1 was identified as having the aspartic protease gene deleted.

```
Forward primer:
                                    (SEQ ID NO: 37)
5'-CGCAATCTATCGAATAGCAG-3'

Reverse primer:
                                    (SEQ ID NO: 38)
5'-CTACATCGAAGCTGAAAGCACGAGA-3'
```

Spores from *T. reesei* AgJg115-118-1 were spread onto TrMM-G plates supplemented with 1 µM 5-fluoro-2'-deoxyuridine (FdU) and incubated at 28° C. for 6 days. Nine isolates were sub-cultured onto PDA plates and incubated at 28° C. for 6 days. The isolates were then screened for the absence of the hpt and tk markers by Fungal Colony PCR in a similar manner described above. The PCR screen was composed of 0.5 µl of each spore suspension, 50 µmol of forward and reverse primers listed below, 10 µl of 2×PHIRE® Plant PCR Buffer, and 0.4 µl of PHIRE® Hot Start II DNA Polymerase in a 20 µl reaction.

```
Forward primer:
                                    (SEQ ID NO: 39)
5'-CGCAATCTATCGAATAGCAG-3'

Reverse primer:
                                    (SEQ ID NO: 40)
5'-GACGTGCAACTTCCTTCAAAC-3'
```

The reactions were incubated in an EPPENDORF® MASTERCYCLER® programmed for 1 cycle at 98° C. for 5 minutes; 40 cycles each at 98° C. for 5 seconds, 58° C. for 5 seconds, and 72° C. for 1 minute 45 seconds; 1 cycle at 72° C. for 1 minute; and a 10° C. hold. The forward primer location is upstream of the 5' flanking region and the reverse primer location is downstream of the 3' flanking region. If the aspartic protease coding sequence has been deleted and the hpt and tk markers have been looped out, the amplified PCR fragments should be 3.6 kb in length.

Genomic DNA from the isolates was prepared as described below and analyzed by Southern blot analysis to confirm the deletion of the 42 kDa aspartic protease coding sequence.

The *T. reesei* AgJg115-118-1 isolates were grown in 50 ml of YP medium supplemented with 2% glucose (w/v) in a 250 ml baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA) according to the manufacturer's protocol with the exception that the lytic incubation was extended to 2 hours. Briefly 5 ml of Kit-supplied buffer AP1 were added to 1 g of tissue in a 15 ml conical bottom tube and incubated for 2 hours at 65° C. Then 1.8 ml of Kit-supplied buffer AP2 were added. The tube was incubated on ice for 5 minutes and centrifuged at 3300 rpm for 5 minutes using a LEGEND™ RT swinging bucket centrifuge (Thermo Fisher Scientific Inc., Waltham, Mass., USA). The supernatant was transferred to a QIAShredder™ column (QIAGEN Inc., Valencia, Calif., USA) and the centrifugation was repeated. Supernatant was transferred to a new 50 ml conical tube to which 1.5 volumes of Kit-supplied buffer AP3/E were added and transferred to a Kit-supplied DNA spin column and the centrifugation was repeated. The column was washed with 12 ml of Kit-supplied buffer AW and the centrifugation was repeated. The column was dried by repeating the centrifugation without any addition. The DNA was eluted by adding 1 ml of Kit-supplied buffer AE and the centrifugation was repeated.

For Southern blot analysis, 2 µg of genomic DNA were digested with 10 units of Nco I in a 30 µl reaction volume and subjected to 0.7% agarose electrophoresis using TAE buffer. The DNA in the gel was depurinated, denatured, neutralized, and transferred to a NYTRAN® SuPerCharge nylon membrane (Whatman, Kent UK) using a TURBOBLOTTER™ (Whatman, Kent UK). The DNA was UV cross-linked to the membrane using a UV STRATALINKER™ (Stratagene, La Jolla, Calif., USA) and prehybridized for 1 hour at 42° C. in 20 ml of DIG Easy Hyb (Roche Diagnostics Corporation, Indianapolis, Ind., USA).

The membrane was hybridized with a 500 bp digoxigenin-labeled *Trichoderma reesei* 42 kDa aspartic protease gene probe, which was synthesized by incorporation of digoxigenin-11-dUTP by PCR using the forward and reverse primers shown below.

```
Forward Primer:
                                    (SEQ ID NO: 41)
5'-CTTCTATCTTGGGATGCTTCACGATACGTGA-3'

Reverse Primer:
                                    (SEQ ID NO: 42)
5'-CGCGCCCTTGAATATCGGAGAAGGT-3'
```

The amplification reaction was composed of 5 µl of 10× Taq Buffer (New England Biolabs, Ipswich, Mass., USA), 2.5 µl of PCR DIG Labeling Mix, 5 ng of pAgJg118, 10 µmol each primer, 2.5 µl of 10 mM dNTPs, 5 units of Taq DNA polymerase (New England Biolabs, Ipswich, Mass., USA), and 36.5 µl of water. The reaction was incubated in an EPPENDORF® MASTERCYCLER® programmed for 1 cycle at 95° C. for 2 minutes; 30 cycles each at 95° C. for 30 seconds, 56° C. for 30 seconds, and 72° C. for 40 seconds; 1 cycle at 72° C. for 15 minutes; and a 4° C. hold. The probe was purified by 1% agarose gel electrophoresis using TAE buffer, excised from the gel, and extracted using a QIAQUICK® Gel Extraction Kit. Briefly 3 volumes of Kit-supplied buffer QG were added to the gel slice and dissolved at 50° C. for approximately 10 minutes. The dissolved gel slice was transferred to a spin column and centrifuged at 13,000 rpm for 1 minute. The column was washed with 750 µl of Kit-supplied buffer PE and then the centrifugation was repeated. DNA was eluted with 25 µl of Kit-supplied buffer EB.

The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed twice under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern blot analysis identified primary transformant *T. reesei* AgJg115-118-1H1 as containing the replacement and being void of the hpt/tk markers.

Example 2

Construction of a cbh2 Replacement Vector pGMER169

A cbh2 coding sequence (SEQ ID NO: 3 [DNA sequence] and SEQ ID NO: 4 [amino acid sequence]) was PCR amplified from pP23YSW (WO 2012/103288) as template with the primers shown below. The underlined portions are overhang to match the pMJ09 vector (US 20080233613).

Forward Primer:
(SEQ ID NO: 43)
5'-ATAGTCAACCGCGGACTGCGCACCATGCGGTCTCTCCTGGCTCTTG

CCCC-3'

Reverse Primer:
(SEQ ID NO: 44)
5'-TCAGGCTTTCGCCACGGAGCTTAATTAATTAGAAAGAGGGGTTGGC

GTTG-3'

The amplification reaction was composed of 10 ng of pP23YSYW, 200 µM dNTP's, 0.5 µM primers, 1×PHUSION® Reaction Buffer (New England Biolabs, Ipswich, Mass., USA), and 1 unit of PHUSION® High Fidelity DNA polymerase (New England Biolabs, Ipswich, Mass., USA) in a final volume of 50 µl. The amplification reaction was incubated in an EPPENDORF® MASTERCYCLER® programmed for 1 cycle at 98° C. for 30 seconds; 30 cycles each at 98° C. for 10 seconds, 59° C. for 30 seconds, and 72° C. for 1 minute; and 1 cycle at 72° C. for 10 minutes.

The PCR product was separated by 1% agarose electrophoresis using TAE buffer where a 1.9 kb band was excised from the gel and the DNA was extracted using a QIAQUICK® Gel Extraction Kit (Example 1). The fragment was inserted into Nco I/Pac I-digested pMJ09 using a GENEART® Seamless Cloning and Assembly Kit (LifeTechnologies, Carlsbad, Calif., USA). The reaction was composed of 4 µl of Kit-supplied 5× Enzyme Buffer, 100 ng of pMJ09, 54 ng of PCR product, and 2 µl of Kit-supplied Enzyme Mix in a 20 µl reaction volume. The reaction was incubated for 30 minutes at room temperature and then placed on ice. Then 8 µl were used to transform ONE SHOT® TOP10 *E. coli* chemically competent cells (Invitrogen, Carlsbad, Calif., USA) by addition to a single use tube containing the competent cells and incubating the cells on ice for 20 minutes. The tube was incubated at 42° C. for 30 seconds after which 250 µl of SOC medium were added. The tube was then incubated at 37° C. for 1 hour with mixing at 200 rpm and 200 µl were transferred to a 150 mm 2XYT+Amp plate and incubated overnight at 37° C. *E. coli* colonies were inoculated into 3 ml of LB+Amp medium in a 14 ml Falcon round-bottom polypropylene tube and incubated at 37° C. overnight with mixing at 200 rpm. Plasmid DNA was isolated from the resulting transformants using a BIOROBOT® 9600 (QIAGEN Inc., Valencia, Calif., USA). The resulting transformants were screened by restriction digestion analysis with Sca I to determine the presence and orientation of the insert. Positive clones were DNA sequenced using an Applied Biosystems 377 XL Automated DNA Sequencer (Applied Biosystems Inc., Foster City, Calif., USA) and dye-terminator chemistry (Giesecke et al., 1992, *J. Virol. Methods* 38: 47-60). The resulting plasmid was designated pAyGm8.

Expression plasmid pGMEr169 contains the cbh2 coding sequence of SEQ ID NO: 3 under control of the *Trichoderma reesei* cbh2 promoter and terminator. Plasmid pGMEr169 was constructed by first PCR amplifying the cbh2 coding sequence from plasmid pAYGm8 using the forward and reverse primers shown below.

Forward primer:
(SEQ ID NO: 45)
5'-AGATCACCCTCTGTGTATTGCACCATGCGGTCTCTCCTGGCTCTTG

CCCCT-3'

Reverse primer:
(SEQ ID NO: 46)
5'-CCGGTCACGAAAGCCTTAATTAACTATTAGAAAGAGGGGTTGGCGT

TGGTAAG-3'

The reverse primer added a Pac I restriction site at the 3' end of the fragment indicated by the underlined portion.

The amplification reaction (50 µl) was composed of 50 ng of plasmid pAYGm8 DNA, 1×PHUSION® HF buffer (New England Biolabs, Inc., Ipswich, Mass., USA), 50 µmol of each primer, 200 µM each dNTP, 3% DMSO (New England Biolabs, Inc., Ipswich, Mass., USA), and 1 unit of PHUSION® High Fidelity DNA polymerase. The reaction was performed in an EPPENDORF® MASTERCYCLER® programmed for 1 cycle at 98° C. for 5 minutes; 35 cycles each at 98° C. for 30 seconds, 60° C. for 30 seconds, and 72° C. for 2 minutes; and a final extension cycle at 72° C. for 7 minutes. The completed PCR was submitted to 0.8% agarose gel electrophoresis using TBE buffer where an approximately 1948 bp PCR product was excised from the gel and purified using a NUCLEOSPIN® Gel and PCR Clean-Up Kit (Macherey Nagel., Bethlehem, Pa., USA).

A second PCR reaction was performed to create a *Trichoderma reesei* cbh2 promoter fragment containing 3' homology to the PCR product above and including an Afl II restriction site at its 5' end. This fragment was PCR amplified from plasmid pJfyS159 (FIG. 1) using the following forward and reverse primers:

Forward primer:
(SEQ ID NO: 47)
5'-GCTTAGGCC<u>CTTAAG</u>CTTAGGCCGGCTTGCTTACT-3'

Reverse primer:
(SEQ ID NO: 48)
5'-AGGGGCAAGAGCCAGGAGAGACCGCATGGTGCAATACACAGAGGGT
GATCTTACAGC-3'

The forward primer added an Afl II restriction site at the 5' end of the fragment while the reverse primer added, at its 3' end, a region of homology to the cbh2 coding sequence described above (sequence in Italics).

The PCR (50 µl) was composed of about 50 ng of plasmid pJfyS159 DNA, 1× PHUSION® HF buffer, 50 µmol of each primer above, 200 µM each of dNTP, 3% DMSO, and 1 unit of PHUSION® High Fidelity DNA polymerase. The reaction was performed in an EPPENDORF® MASTERCYCLER® programmed for 1 cycle at 98° C. for 5 minutes; 35 cycles each at 98° C. for 30 seconds, 60° C. for 30 seconds, and 72° C. for 1.5 minutes; and a final extension cycle at 72° C. for 7 minutes. The completed PCR was submitted to 0.8% agarose gel electrophoresis using TBE buffer where an approximately 1340 bp PCR product was excised from the gel and purified using a NUCLEOSPIN® Gel and PCR Clean-Up Kit.

The 1948 bp and 1340 bp fragments were fused together by splicing by overlap extension (SOE) PCR using the forward primer directly above and reverse primer from the cbh2 PCR above, resulting in a 3237 bp fragment in which the *Trichoderma reesei* cbh2 promoter fragment was added upstream of the cbh2 coding sequence.

The PCR (50 µl) was composed of about 120 ng of each of the fragments for a total amount of template DNA of about 240 ng, 1×PHUSION® HF buffer, 50 µmol of primer 1201537, 50 µmol of primer 1201280, 200 µM each of dATP, dCTP, dGTP, and dTTP, 1.5 µl of 100% DMSO, and 1 unit of PHUSION® High Fidelity DNA polymerase. The reaction was performed in an EPPENDORF® MASTER-CYCLER® programmed for 1 cycle at 98° C. for 3 minutes; 35 cycles each at 98° C. for 30 seconds, 60° C. for 30 seconds, and 72° C. for 2.5 minutes; and a final extension cycle at 72° C. for 7 minutes. The completed PCR was submitted to 0.8% agarose gel electrophoresis using TBE buffer where an approximately 3237 bp PCR product was excised from the gel and purified using a NUCLEOSPIN® Gel and PCR Clean-Up Kit. Briefly, 2 volumes of Buffer NT were added to the gel slice and the sample was heated 10 minutes at 50° C. The entire solution was transferred to a Kit-supplied centrifugal column. The column was centrifuged at 13,000 rpm for 1 minute and washed with Kit-supplied wash buffer NT3 and re-centrifuged. DNA was eluted with 20 µl of Kit-supplied elution buffer and centrifuged at 13,000 rpm for 1 minute.

The resulting 3237 bp fragment was digested with Afl II and Pac I and ligated to the 9044 bp Afl II/Pac I fragment from plasmid pJfyS159. About 20 µg of plasmid pJfyS159 were digested with Afl II and Pac I at 37° C. overnight. Before stopping the digestion reaction, 1 µl of calf intestinal alkaline phosphatase (New England Biolabs, Ipswich, Mass., USA) was added to the pJfyS159-Afl II/Pac I digestion in order to de-phosphorylate the plasmid ends. The reaction was incubated again at 37° C. for 1 hour. The resulting reaction was submitted to 0.8% agarose gel electrophoresis using TBE buffer where a 9044 bp vector fragment was excised from the gel and purified using a NUCLEOSPIN® Gel and PCR Clean-up Kit. The 3237 bp PCR product comprising the *T. reesei* cbh2 promoter and the cbh2 coding sequence was digested with restriction enzymes Afl II and Pac I at 37° C. for 3 hours. The resulting digested 3209 bp fragment was cleaned up using a NUCLEOSPIN® Gel and PCR Clean-up Kit.

Figure 2:
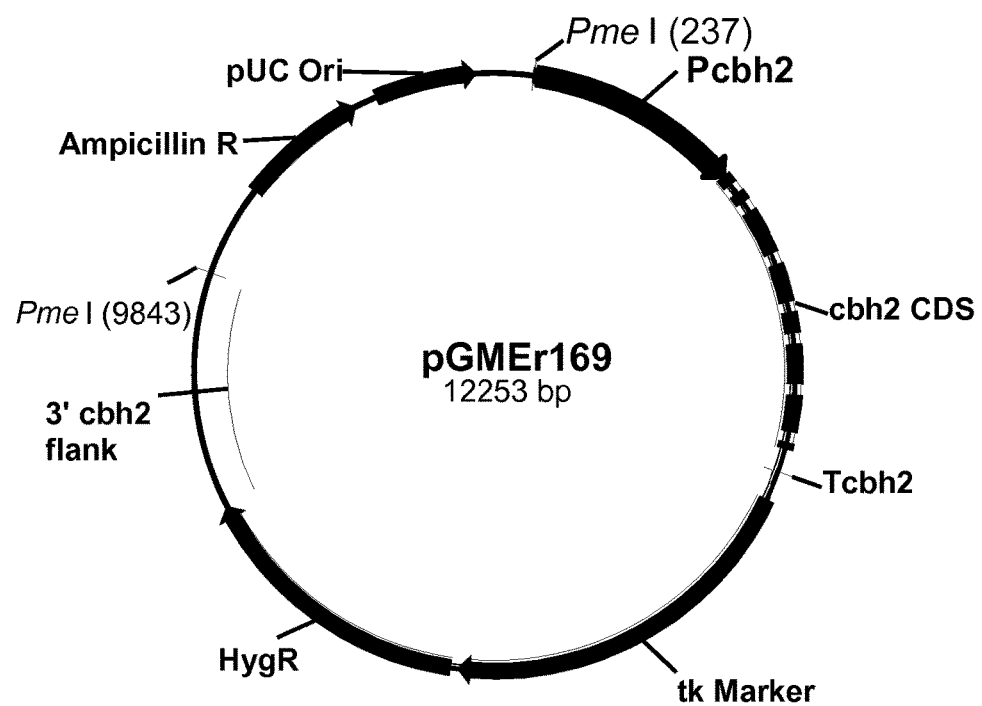
FIG. 2 shows a restriction map of plasmid pGMEr169.

The ligation reaction was performed using a QUICK LIGATION™ Kit (New England Biolabs, Inc., Ipswich, Mass., USA). The ligation reaction was composed of 3 µl of vector fragment, 3 µl of the *T. reesei* cbh2 promoter/cbh2 coding sequence insert fragment, 4 µl of sterile deionized water, 10 µl of 2× Quick Ligation Buffer (New England Biolabs, Ipswich, Mass., USA), and 1 µl of Quick T4 Ligase (New England Biolabs, Ipswich, Mass., USA). The ligation reaction was incubated for 1 hour at room temperature. A 5 µl aliquot of the ligation reaction was transformed into ONE SHOT® TOP10 *E. coli* chemically competent cells. Briefly, 5 µl of the ligation reaction were added to one tube containing the competent cells and the mixture was incubated on ice for 30 minutes. The tube was then incubated at 42° C. for 30 seconds after which 250 µl of SOC medium were added. The tube was then incubated at 37° C. for 1 hour with mixing at 200 rpm and 250 µl were transferred to a 150 mm 2XYT+Amp plate and incubated overnight at 37° C. Several of the resulting transformants were screened for proper insertion of the desired insert by Hind III restriction digestion. *E. coli* transformant colonies were inoculated into 3 ml of LB+Amp medium in a 14 ml Falcon round-bottom polypropylene tube and incubated at 37° C. overnight with mixing at 200 rpm. Plasmid DNA was isolated using a BIOROBOT® 9600. Plasmid DNA was extracted and purified using a Plasmid Mini Kit (QIAGEN Inc., Valencia, Calif., USA). Four transformants yielding the desired Hind III bands of 9168 bp, 2764 bp, 208 bp, and 113 bp were submitted to sequencing analysis for final insert confirmation. DNA sequencing was performed using an Applied Biosystems 377 XL Automated DNA Sequencer and dye-terminator chemistry (Giesecke et al., 1992, supra). The resulting plasmid was designated pGMER169 (FIG. 2), which comprises the cbh2 coding sequence of SEQ ID NO: 3 under transcriptional control of the *Trichoderma reesei* cbh2 gene promoter and terminator.

Example 3

Replacement of the Native Cbh2 Gene in *Trichoderma reesei* Strain AgJg115-118-1H1

Approximately 200 µg of plasmid pGMEr169 (Example 2) were digested with Pme I. The digestion reaction was purified by 1% agarose gel electrophoresis using TAE buffer. A 9.6 kb DNA band was excised from the gel and extracted using a QIAQUICK® Gel Extraction Kit (Example 1). *T. reesei* strain AgJg115-118-1H1 (Example 1) was transformed with Pme I digested pGMer169 DNA selecting for hygromycin resistance (hpt) as described in Example 1. Thirty-five transformants were obtained and each one was transferred to a PDA plate and incubated for 2-4 days at 28° C. A spore PCR using a PHIRE® Plant Direct PCR Kit was utilized to identify transformants which had integrated the pGMer169 Pme I fragment at the cbh2 locus. Briefly, spores from each transformant were collected with a sterile 1 µl inoculation loop and transferred to 15 µl of Kit-supplied dilution buffer in 0.2 ml PCR strip tubes and incubated for 5 minutes at room temperature. Each spore suspension was centrifuged briefly in a strip-fuge mini centrifuge (Sigma Aldrich, St Louis, Mo., USA) and 1 µl of each supernatant was used in the spore PCR reaction. The Spore PCR reaction (20 μl) was composed of 1×PHIRE® Plant Direct PCR buffer (contains dNTPs and Mg), 10 pmol of gene specific forward and reverse primers shown below, and 0.4 μl of PHIRE® II Hot Start DNA Polymerase.

```
Forward primer (homologous to 5' flank of cbh2
of SEQ ID NO: 3):
                                    (SEQ ID NO: 49)
5'-CTCTATAGAGGAATCAGCGT-3'

Reverse primer1 (homologous to cbh2 of SEQ ID
NO: 3):
                                    (SEQ ID NO: 50)
5'-TACACCTCGGACGAGTATTC-3'

Reverse primer2 (homologous to T. reesei cbh2
coding sequence):
                                    (SEQ ID NO: 51)
5'-TCTAGAGGCACACTAGCTGC-3'
```

The amplification reactions were incubated in an EPPENDORF® MASTERCYCLER® programmed for 1 cycle at 98° C. for 5 minutes; 40 cycles each at 98° C. for 5 seconds, 57° C. for 5 seconds, and 72° C. for 45 seconds; and 1 cycle at 72° C. for 1 minute.

The completed PCRs were subjected to 0.8% agarose gel electrophoresis using TBE buffer. Transformants with the correct replacement of the native *T. reesei* cbh2 gene with the cbh2 coding sequence of SEQ ID NO: 3 produced a 2.1 kb fragment, whereas transformants with the intact native cbh2 gene produced a 1.7 kb fragment.

Two transformants produced the correct replacement fragment and were chosen for spore isolation. Spores from a 6 day old PDA plate were collected in 4 ml of 0.01% TWEEN® 20 and the spore concentration was determined using a hemocytometer. Spores were diluted appropriately to a concentration of 10³ spores per ml using sterile water and 100 spores were spread onto PDA plates. Plates were incubated for 2 days at 30° C. Isolated colonies from each transformant were picked with a sterile 10 μl inoculation loop and transferred to a new 50 mm PDA plate and incubated at 30° C. Spore PCR using a PHIRE® Plant Direct PCR Kit (protocol and primers described above) was utilized to identify spore isolates with the correct gene replacement. Correct spore isolates were chosen and the hpt/tk markers were looped out using 5-fluorodeoxyuridine (FdU) counter-selection. Spores from the PDA plate were collected in 4 ml of 0.01% TWEEN® 20 and approximately 30 μl of the spore suspension were added to the middle of a 50 mm TrMM-G plate supplemented with 1 μM FdU. The FdU plates were incubated for 6 days at 30° C. A chunk of mycelia was cut from the outer edge of the growth area and transferred to a PDA plate and the plate was incubated at 30° C. Spore PCR using a PHIRE® Plant Direct PCR Kit (as described above) was utilized to identify isolates with the correct loop out of the hpt/tk markers.

Screen for hpt marker

```
Forward primer (homologous to hpt marker):
                                    (SEQ ID NO: 52)
5'-GGCATGACCTTTTGATGATCG-3'

Reverse primer (homologous to 3' flank of
T. reesei cbh2 locus):
                                    (SEQ ID NO: 53)
5'-TTACAACGTACCTACCTAGT-3'

Screen for tk marker:
Forward primer (homologous to 5' flank of
T. reesei cbh2 locus):
                                    (SEQ ID NO: 54)
5'-CTCTATAGAGGAATCAGCGT-3'

Reverse primer (homologous to tk marker):
                                    (SEQ ID NO: 55)
5'-CGTGTCCCCGATATGGGTCGTGGG-3'
```

The amplification reactions were incubated in an EPPENDORF® MASTERCYCLER® programmed for 1 cycle at 98° C. for 5 minutes; 40 cycles each at 98° C. for 7 seconds, 57° C. for 7 seconds, and 72° C. for 2 minutes; and 1 cycle at 72° C. for 2 minutes.

The completed PCRs were subjected to 0.8% agarose gel electrophoresis using TAE buffer. Isolates that still contained the hpt marker produced a 1.8 kb fragment and isolates that still contained the tk marker produced a 5.5 kb fragment. Isolates that were void of the hpt and tk markers were carried forward.

Spores from a 6 day old PDA plate were transferred to 1 ml of 0.01% TWEEN® 20 using an inoculation loop and the spore concentration was determined using a hemocytometer. Spores were diluted appropriately to a concentration of 10³ spores per ml and 100 spores were spread onto PDA plates. Plates were incubated at 30° C. for 2 days. Colonies were picked with a sterile 10 μl inoculation loop and transferred to new 50 mm PDA plates and incubated for 5 days at 28° C. The final Isolates were checked again for the absence of the hpt marker by spore PCR as described above.

Genomic DNA from the final isolates was prepared as described below and analyzed by Southern blot analysis.

The *Trichoderma reesei* isolates were each grown in 25 ml of YP medium supplemented with 2% glucose (w/v) in a 125 ml baffled shake flask at 28° C. for 2 days with agitation at 200 rpm. Mycelia were harvested from each culture by vacuum filtration through Whatman 1 filter paper in a Buchner funnel. The mycelia preparations were each washed twice in deionized water, dried under vacuum, and then transferred to a 2 ml microfuge tube. The mycelia preparations were dried approximately 16 hours in a Savant ISS110 SpeedVac concentrator (Thermo Fisher Scientific, Waltham, Mass., USA). The dried mycelia preparations were ground to a fine powder and total DNA was isolated using a MasterPure™ Yeast DNA Purification Kit (Epicentre, Madison, Wis., USA). Ground mycelia equivalent to approximately a 50 μl volume were each transferred to a 2 ml microfuge tube. Yeast Cell Lysis Solution (300 μl; Epicentre, Madison, Wis., USA) was added to each mycelia sample and each sample was vortexed. Each sample was incubated at 65° C. for 20 minutes. The samples were placed on ice for 5 minutes. MPC Protein Precipitation Reagent (150 μl; Epicentre, Madison, Wis., USA) was added to each sample and the samples were vortexed for 10 seconds. The samples were centrifuged in a microcentrifuge for 10 minutes at ≥10,000 rpm. The supernatants were each transferred to a clean 1.7 ml microcentrifuge tube and 500 μl of isopropanol were added. The samples were mixed thoroughly by inversion. The DNAs were pelleted by centrifugation in a microcentrifuge for 10 minutes at ≥10,000 rpm. The supernatants were discarded. The pellets containing the DNA were washed with 0.5 ml of 70% ethanol. The samples were centrifuged in a microcentrifuge for 4 minutes at ≥10,000 rpm. The ethanol was removed with a pipette and the pellets were air dried for 7 minutes at room temperature. The DNA pellets were resuspended in 60 μl of TE. A 1.5 μl aliquot of 5 μg/μl RNase A was added to each tube and the samples were incubated 30 minutes at 37° C.

For Southern blot analysis approximately 1 µg of genomic DNA was digested with 20 units of Hind III and subjected to 0.8% agarose electrophoresis using TAE buffer. The DNA in the gel was depurinated, denatured, neutralized, and transferred to a NYTRAN® SuPerCharge nylon membrane using a TURBOBLOTTER™. The DNA was UV cross-linked to the membrane using a UV STRATALINKER™ and prehybridized for 1 hour at 42° C. in 20 ml of DIG Easy Hyb.

A template for a probe hybridizing to the 3' flanking region of the *T. reesei* cbh2 gene was generated using PHUSION™ High-Fidelity Hot Start DNA Polymerase (New England Biolabs, Ipswich, Mass., USA) and gene-specific forward and reverse primers shown below.

```
Forward primer:
                                      (SEQ ID NO: 56)
5'-TCTTGAGCCGCATCGCATAGA-3'

Reverse primer:
                                      (SEQ ID NO: 57)
5'-TACGGTCAGCGCTCATGCGAA-3'
```

Fifty picomoles of each of the primers were used in a PCR composed of 100 ng of *T. reesei* RutC30 genomic DNA, 1×PHUSION™ High-Fidelity Hot Start DNA Polymerase buffer (New England Biolabs, Ipswich, Mass., USA), 1 µl of a 10 mM blend of dATP, dTTP, dGTP, and dCTP, and 1 unit of PHUSION™ High-Fidelity Hot Start DNA Polymerase in a final volume of 50 µl. The amplification was performed using an EPPENDORF® MASTERCYCLER® 5333 epgradient S (Eppendorf Scientific, Inc., Westbury, N.Y., USA) programmed for 1 cycle at 98° C. for 2 minutes; 34 cycles each at 98° C. for 15 seconds, 60° C. for 30 seconds, and 72° C. for 1 minute 30 seconds, and 1 cycle at 72° C. for 10 minutes. The completed PCR was purified by 0.8% agarose gel electrophoresis using TAE buffer where a 0.46 kb DNA band was excised from the gel and the DNA was extracted using a NUCLEOSPIN® Extract II Kit. Briefly, 3 volumes of Buffer NT were added to the gel slice and the sample was heated 10 minutes at 50° C. The entire solution was transferred to a Kit-supplied centrifugal column. The column was centrifuged at 13,000 rpm for 1 minute and washed with Kit-supplied wash buffer NT3 and re-centrifuged. DNA was eluted with 30 µl of Kit-supplied elution buffer and centrifuged at 13,000 rpm for 1 minute.

A probe hybridizing to the 3' flanking region of the *T. reesei* cbh2 gene was generated using a PCR Dig Probe Synthesis Kit (Roche Diagnostics Corporation, Indianapolis, Ind., USA) with the forward and reverse primers shown directly above.

The 50 µl PCR reaction was composed of 1×PCR DIG Probe Synthesis mix, 50 pmol of each primer, 1×PCR buffer with MgCl$_2$, 24 ng purified probe template (described above), and 2.6 units of EXPAND® High Fidelity DNA polymerase (Roche Applied Science, Penzberg, Germany). The cycling parameters were as follows: 1 cycle at 95° C. for 2 minute; 30 cycles each at 95° C. for 30 seconds, 59° C. for 30 seconds, and 72° C. for 45 seconds; and 1 cycle at 72° C. for 7 minutes.

The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern blot analysis identified final spore isolates that contained the cbh2 replacement (3.3 kb hybridizing fragment) and did not contain the hpt/tk markers. The native *T. reesei* cbh2 locus produces a 4.7 kb hybridizing fragment. One spore isolate was chosen as the final strain and designated *T. reesei* KM1000-34.

Example 4

Generation of cbh1 Replacement Vector pAyGm10

To construct plasmid pAyGm7, a cbh1 coding sequence (SEQ ID NO: 1 [DNA sequence] and SEQ ID NO: 2 [amino acid sequence]) was amplified by PCR from plasmid pP23YSY (WO 2012/103293) as template with the primers shown below. The underlined portions are overhangs to match the site of insertion into plasmid pMJ09 (WO 2005/056772).

```
Forward Primer
                                      (SEQ ID NO: 58)
5'-ATAGTCAACCGCGGACTGCGCACCATGGCCAGCCTCTTCTCTTTCA

AGATG-3'

Reverse Primer
                                      (SEQ ID NO: 59)
5'-CAGGCTTTCGCCACGGAGCTTAATTAATTACAGGCACTGGTAGTAG

TAGGGGTTC-3'
```

The amplification reaction was composed of 15 ng of pP23YSY, 200 µM dNTP's, 0.5 µM primers, 1×PHUSION® HF Reaction Buffer, and 1 unit of PHUSION® High Fidelity DNA polymerase in a final volume of 50 µl. The reaction was incubated in an EPPENDORF® MASTERCYCLER® programmed for 1 cycle at 98° C. for 30 seconds; 30 cycles each at 98° C. for 10 seconds, 62° C. for 30 seconds, and 72° C. for 1 minute; and 1 cycle at 72° C. for 10 minutes.

The fragment was inserted directly into Nco I/Pac I-digested pMJ09 following PCR using a GENEART® Seamless Cloning and Assembly Kit. The reaction was composed of 4 µl of Kit-supplied 5× Enzyme Buffer, 100 ng of pMJ09, 45.8 ng of PCR product, and 2 µl of Kit-supplied Enzyme Mix in a 20 µl reaction volume. The reaction was incubated at room temperature for 30 minutes and then placed on ice. Then 1.3 µl were used to transform ONE SHOT® TOP10 *E. coli* chemically competent cells by addition to a single use tube containing the competent cells and incubating the cells on ice for 20 minutes. The tube was incubated at 42° C. for 30 seconds after which 250 µl of SOC medium were added. The tube was then incubated at 37° C. with mixing at 200 rpm for 1 hour and 200 µl were transferred to a 150 mm 2XYT+Amp plate and incubated overnight at 37° C. *E. coli* transformant colonies were each inoculated into 3 ml of LB+Amp medium in a 14 ml Falcon round-bottom polypropylene tube and incubated at 37° C. overnight with agitation at 200 rpm. Plasmid DNA was isolated from the resulting transformants using a BIOROBOT® 9600. The resulting transformants were screened by restriction digestion analysis with Sal I to determine the presence and orientation of the insert and positive clones were DNA sequenced using an Applied Biosystems 377 XL Automated DNA Sequencer and dye-terminator chemistry (Giesecke et al., 1992, supra). The resulting plasmid was designated pAyGm7.

Figure 3:
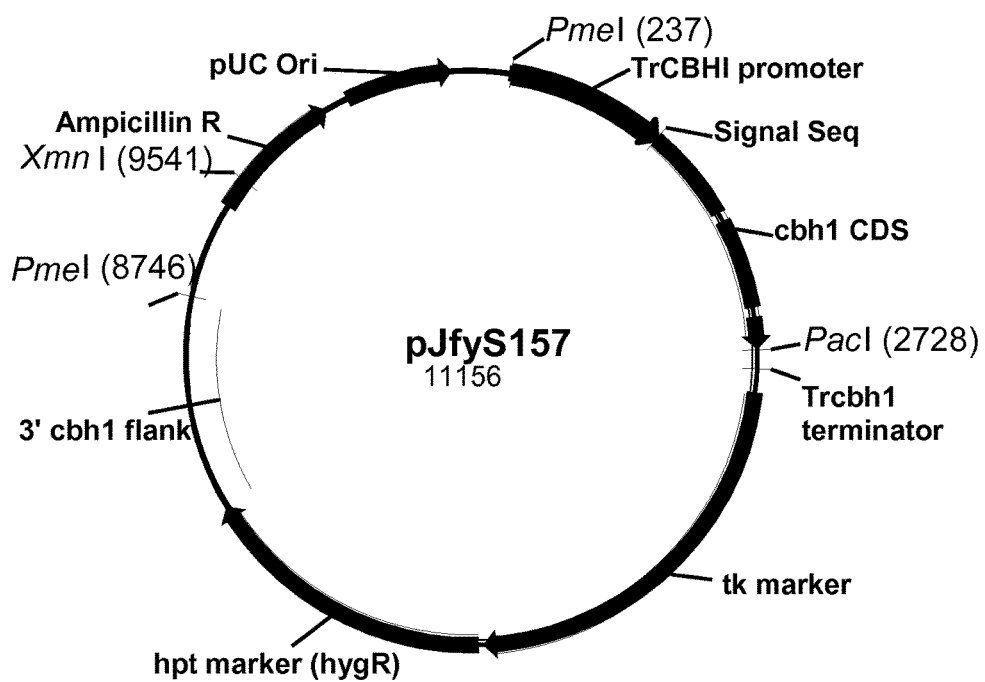
FIG. 3 shows a restriction map of plasmid pJfyS157.

To generate plasmid pAyGm10, two individual PCRs were combined by SOE PCR. First, the individual fragments were amplified from either pJfyS157 (FIG. 3) or pAyGm7 using the forward and reverse primers shown below.

pJfyS157:

```
Forward Primer:
                                         (SEQ ID NO: 60)
5'-CAGTTGGGTGCACGAGTGGGTTACATCGAACTGG-3'

Reverse Primer:
                                         (SEQ ID NO: 61)
5'-GAAAGAGAAGAGGCTGGCCATGGTGCGCAGTCCGCGGTTGACTAT

TG-3' pAyGm7:
Forward Primer:
                                         (SEQ ID NO: 62)
5'-CAATAGTCAACCGCGGACTGCGCACCATGGCCAGCCTCTTCTCTT

TC-3'

Reverse Complement Primer:
                                         (SEQ ID NO: 63)
5'-GCGTCAGGCTTTCGCCACGGAGC-3'
```

The amplification reactions were composed of 10 ng of the respective plasmid template, 200 µM dNTP's, 0.5 µM primers, 1×PHUSION® HF Reaction Buffer, and 1 unit of PHUSION® High Fidelity DNA polymerase in a final volume of 50 µl. Both PCR reactions were incubated in an EPPENDORF® MASTERCYCLER®. Cycling conditions for pJfyS157 were 1 cycle at 98° C. for 30 seconds; 30 cycles each at 98° C. for 10 seconds, 70° C. for 30 seconds, and 72° C. for 1 minute and 30 seconds; and 1 cycle at 72° C. for 10 minutes. Cycling conditions for pAyGm7 were 1 cycle at 98° C. for 30 seconds; 30 cycles each at 98° C. for 10 seconds, 67° C. for 30 seconds, and 72° C. for 1 minute; and 1 cycle at 72° C. for 10 minutes.

The PCR products were separated by 1% agarose electrophoresis using TAE buffer where a 1.6 kb band for the pAyGm10 fragment and a 2.8 kb band for the pJFYS157 fragment were excised from the gels and extracted using a QIAQUICK® Gel Extraction Kit (Example 1). The two fragments were then spliced together using SOE PCR with the forward and reverse primers of SEQ ID NO: 60 and SEQ ID NO: 63, respectively.

The amplification reaction was composed of 125 ng of the pJFYS157 fragment and 218 ng of the pAyGm7 fragment, 200 µM dNTP's, 0.5 µM primers, 1×PHUSION® HF Reaction Buffer, and 1 unit of PHUSION® High Fidelity DNA polymerase in a final volume of 50 µl. The reaction was incubated in an EPPENDORF® MASTERCYCLER® programmed for 1 cycle at 98° C. for 30 seconds; 30 cycles each at 98° C. for 10 seconds, 67° C. for 30 seconds, and 72° C. for 2 minute 30 seconds; and 1 cycle at 72° C. for 10 minutes.

Figure 4:
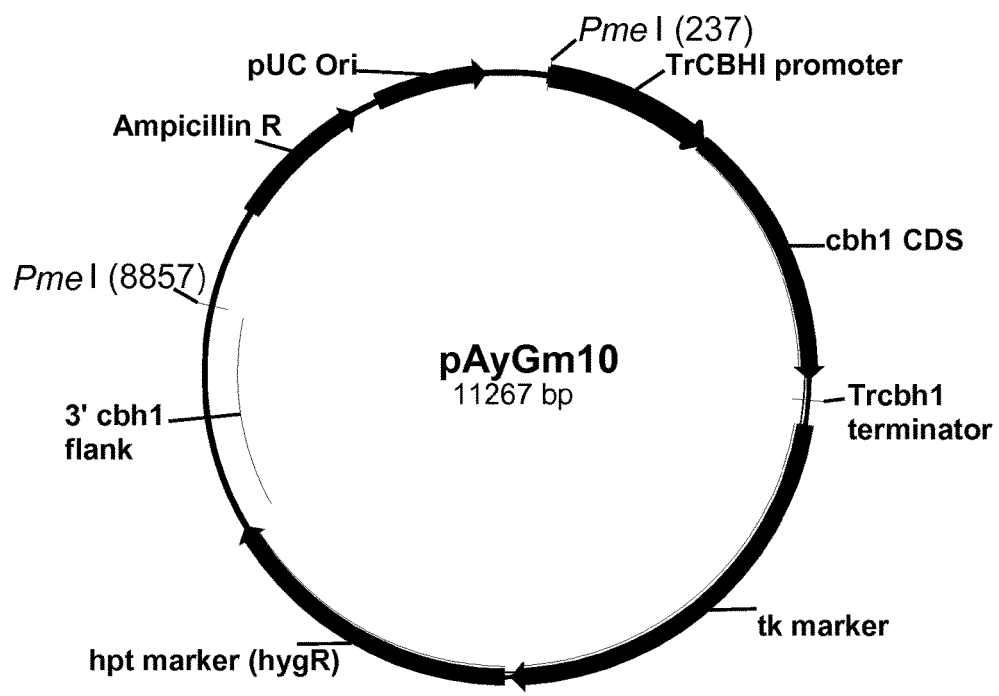
FIG. 4 shows a restriction map of plasmid pAyGm10.

The PCR fragment was then digested with Pac I and Xmn I and subjected to a QIAQUICK® PCR Purification Kit (QIAGEN Inc., Valencia, Calif., USA). Briefly, 5 volumes of Kit-supplied buffer PB1 were added to the PCR reaction and subsequently added to a Kit-supplied spin column by transferring to the column and centrifuging at 13,000 rpm for 1 minute. The column was washed with 750 µl of Kit-supplied buffer PE and the centrifugation was repeated. DNA was eluted with 25 µl of Kit-supplied buffer EB. The 4.4 kb Pac I and Xmn I digested PCR fragment was ligated to Pac I and Xmn I digested pJfyS157 using T4 DNA ligase (Roche, Indianapolis, Ind., USA). The ligation reaction was composed of 50 ng of the Pac I and Xmn I digested pJfyS157, 140 ng of the Pac I and Xmn I digested 4.4 kb PCR fragment, 1× Ligase Buffer (Roche, Indianapolis, Ind., USA), and 2 units of T4 DNA ligase in a final volume of 20 µl. The reaction was incubated at room temperature for 10 minutes and 5 µl of the reaction were transformed into ONE SHOT® TOP10 *E. coli* chemically competent cells by addition to a single use tube containing the competent cells and incubating the cells on ice for 20 minutes. The tube was incubated at 42° C. for 30 seconds after which 250 µl of SOC medium were added. The tube was then incubated at 37° C. with mixing at 200 rpm for 1 hour and 200 µl were transferred to a 150 mm 2XYT+Amp plate and incubated overnight at 37° C. *E. coli* transformant colonies were inoculated into 3 ml of LB+Amp medium in a 14 ml Falcon round-bottom polypropylene tube and incubated at 37° C. overnight with agitation at 200 rpm. Plasmid DNA was isolated from the resulting transformants using a BIOROBOT® 9600. The resulting transformants were screened by restriction digestion analysis with Hind III to determine the presence and orientation of the insert and positive clones were DNA sequenced using an Applied Biosystems 377 XL Automated DNA Sequencer and dye-terminator chemistry (Giesecke et al., 1992, supra). The resulting plasmid was designated pAyGm10 (FIG. 4).

Example 5

Replacement of the Native *Trichoderma reesei* cbh1

Approximately 200 µg of plasmid pAyGm10 (Example 4) were digested with Pme I. The digestion reaction was purified by 0.8% agarose gel electrophoresis using TAE buffer where an 8.6 kb DNA band was excised from the gel and extracted using a NUCLEOSPIN® Extract II Kit. Three volumes of Kit-supplied NT buffer were added to the gel slice and the sample was heated 10 minutes at 50° C. The solution was transferred to 6 Kit-supplied centrifugal columns. The columns were centrifuged at 13,000 rpm for 1 minute and washed with Kit-supplied wash buffer NT3 and re-centrifuged. The DNA was eluted with 70 µl of 65° C. Kit-supplied NE buffer per column. The 6 eluted DNA samples were combined. *T. reesei* strain KM1000-34 (Example 3) was transformed with Pme I-digested pAyGm10 DNA selecting for hygromycin resistance (hpt) as described in Example 1. Five transformants were obtained and each one was picked and transferred to a PDA plate and incubated for 2-4 days at 30° C. Spore PCR using a PHIRE® Plant Direct PCR Kit was employed to identify transformants which had integrated the pAyGm10 Pme I fragment at the *T. reesei* cbh1 locus. Briefly, spores from the transformants were collected with a sterile 1 µl inoculation loop and transferred to 15 µl of Kit-supplied dilution buffer in 0.2 ml PCR strip tubes and incubated at room temperature for 5 minutes. The spore suspension was centrifuged briefly in a strip-fuge mini centrifuge (Sigma Aldrich, St Louis, Mo., USA) and 1 µl of supernatant was used in the spore PCR. The 20 µl spore PCR reaction was composed of 1×PHIRE® Plant Direct PCR buffer (contains dNTPs and Mg), 10 µmol of gene specific forward and reverse primers shown below, and 0.4 µl of PHIRE® II Hot Start DNA Polymerase.

Screening primers for 5' end of *T. reesei* cbh1 locus

```
Forward primer (homologous to 5' flank of cbh1
locus):
                                       (SEQ ID NO: 64)
5'-GTAATTTGCCTGCTTGACCG-3'

Reverse primer (homologous to cbh1 coding
sequence of SEQ ID NO: 1):
                                       (SEQ ID NO: 65)
5'-TGAAGATCTGGTAGGTTGTG-3'

Screening primers for 3' end of T. reesei cbh1
locus
Forward primer (homologous to hpt marker):
                                       (SEQ ID NO: 66)
5'-TCATTGACTGTCTGTCCTCT-3'

Reverse primer (homologous to 3' flank of cbh1
locus):
                                       (SEQ ID NO: 67)
5'-TACCATGACTGTCACGATAG-3'
```

The amplification reaction was incubated in an EPPENDORF® MASTERCYCLER® programmed for 1 cycle at 98° C. for 5 minutes; 40 cycles each at 98° C. for 5 seconds, 57° C. for 5 seconds, and 72° C. for 1 minute; and 1 cycle at 72° C. for 1 minute.

The completed PCRs were subjected to 1% agarose gel electrophoresis using TAE buffer. Transformants having the correct replacement of the native cbh1 gene with the cbh1 coding sequence of SEQ ID NO: 1 produced a 1.46 kb fragment with the 5' end screening primers and a 1.64 kb fragment with the 3' end screening primers.

Two transformants produced the correct replacement fragments and were chosen for spore isolation and loop out of the hpt/tk markers. Spores from a 6 day old PDA plate were collected in 5 ml of 0.01% TWEEN® 20 and the spore concentration was determined using a hemocytometer. Spores were diluted appropriately to a concentration of 10³ spores per ml and 100 spores were spread onto PDA plates. The plates were incubated for 2 days at 30° C. Nine colonies from each transformant were picked with a sterile 10 µl inoculation loop and transferred to a new 50 mm PDA plate and incubated for 2 days at 30° C. Spore PCR using a PHIRE® Plant Direct PCR Kit was utilized as described above to identify spore isolates with the correct gene replacement.

Screening primers for 5' end of *T. reesei* cbh1 locus

```
Forward primer (homologous to 5' flank of cbh1
locus):
                                       (SEQ ID NO: 68)
5'-GTAATTTGCCTGCTTGACCG-3'

Reverse primer1 (homologous to cbh1 coding
sequence of SEQ ID NO: 1):
                                       (SEQ ID NO: 69)
5'-TGAAGATCTGGTAGGTTGTG-3'

Reverse primer2 (homologous to T. reesei cbh1
gene):
                                       (SEQ ID NO: 70)
5'-CGAGATGACGGCCAACTTCC-3'

Screening primers for 3' end of T. reesei cbh1
locus
Forward primer1 (homologous to hpt marker):
                                       (SEQ ID NO: 71)
5'-TCATTGACTGTCTGTCCTCT-3'

Forward primer2 (homologous to T. reesei cbh1
gene):
                                       (SEQ ID NO: 72)
5'-GGAAGTTGGCCGTCATCTCG-3'

Reverse primer (homologous to 3' flank of T.
reesei cbh1 locus):
                                       (SEQ ID NO: 73)
5'-TACCATGACTGTCACGATAG-3'
```

The amplification reactions were incubated in an EPPENDORF® MASTERCYCLER® programmed for 1 cycle at 98° C. for 5 minutes; 40 cycles each at 98° C. for 5 seconds, 57° C. for 5 seconds, and 72° C. for 1 minute; and 1 cycle at 72° C. for 1 minute.

The completed PCRs were subjected to 0.8% agarose gel electrophoresis using TAE buffer. Transformants having the correct replacement of the native *T. reesei* cbh1 gene with the cbh1 coding sequence of SEQ ID NO: 1 produced a 1.46 kb fragment with the 5' end screening primers. The native *T. reesei* cbh1 locus produced a 1.1 kb fragment with the 5' end screening primers. Transformants having the correct replacement of the native *T. reesei* cbh1 gene with the cbh1 coding sequence of SEQ ID NO: 1 produced a 1.64 kb fragment with the 3' end screening primers. The native *T. reesei* cbh1 locus produced a 3.0 kb fragment with the 3' end screening primers.

Correct spore isolates were chosen and the hpt/tk markers were looped out using 5-fluorodeoxyuridine (FdU) counter-selection. A small chunk of mycelia from each PDA plate was added to the middle of a 50 mm TrMM-G plate supplemented with 1 µM FdU. The FdU plates were incubated at 30° C. for 7 days. A chunk of mycelia was cut from the outer edge of the growth area of each plate and transferred to PDA platea. The plates were incubated at 30° C. for 2-4 days. Spore PCR using a PHIRE® Plant Direct PCR Kit (protocol described above) was utilized to identify isolates with the correct loop out of the hpt/tk markers.

Screen for hpt/tk marker excision:

```
Forward primer (homologous to cbh1 coding sequence
of SEQ ID NO: 1):
                                       (SEQ ID NO: 74)
5'-TTCCCCAACCACGACCACCT-3'

Reverse primer (homologous to 3' flank of T.
reesei cbh1):
                                       (SEQ ID NO: 75)
5'-TACCATGACTGTCACGATAG-3'

Screen for hpt marker:
Forward primer (homologous to hpt marker):
                                       (SEQ ID NO: 76)
5'-GGCATGACCTTTTGATGATCG-3'

Reverse primer (homologous to 3' flank of T.
reesei cbh1):
                                       (SEQ ID NO: 77)
5'-TACCATGACTGTCACGATAG-3'
```

The amplification reactions were incubated in an EPPENDORF® MASTERCYCLER® programmed for 1 cycle at 98° C. for 5 minutes; 40 cycles each at 98° C. for 5 seconds, 57° C. for 5 seconds, and 72° C. for 1 minute; and 1 cycle at 72° C. for 1 minute.

The completed PCR reactions were subjected to 0.8% agarose gel electrophoresis using TAE buffer. Isolates that still contained the hpt marker produced a 1.5 kb fragment using the hpt screening primers. Isolates that were void of the hpt and tk markers produced a 1.5 kb fragment using the loop out screening primers. Isolates with the correct marker loop out were carried forward.

Spores from a 6 day old PDA plate were collected in 5 ml of 0.01% TWEEN® 20 and the spore concentration was determined using a hemocytometer. Spores were diluted appropriately to a concentration of $10^3$ spores per ml and 100 spores were spread onto PDA plates. The plates were incubated for 2 days at 30° C. Eight colonies from each transformant were picked with a sterile 10 µl inoculation loop and transferred to new 50 mm PDA plates and incubated for 2 days at 30° C. Spore PCR using a PHIRE® Plant Direct PCR Kit (protocol described above) was utilized to identify final spore isolates with the correct gene replacement and hpt/tk marker loop out. The PCR primers used for the hpt/tk marker loop out and the screen for the hpt marker are described above.

Genomic DNA of final spore isolates was prepared (as described in Example 3) and analyzed by Southern blot analysis. For Southern blot analysis approximately 1 µg of genomic DNA was digested with 20 units of Bgl II and 20 units of Bam HI and subjected to 0.8% agarose electrophoresis using TAE buffer. The DNA in the gel was depurinated, denatured, neutralized, and transferred to a NYTRAN® SuPerCharge nylon membrane using a TURBOBLOTTER™. The DNA was UV cross-linked to the membrane using a UV STRATALINKER™ and prehybridized for 1 hour at 42° C. in 20 ml of DIG Easy Hyb.

A probe hybridizing to the 3' flanking region of the cbh1 gene was generated using a PCR Dig Probe Synthesis Kit with the forward and reverse primers shown below. The PCR reaction (50 µl) was composed of 1× Taq DNA Polymerase Buffer (New England Biolabs, Ipswich, Mass., USA), 50 µmol each primer, 0.5×PCR DIG Probe Synthesis mix, 0.5× dNTP stock solution (Roche Diagnostics, Indianapolis, Ind., USA), 100 ng *T. reesei* RutC30 genomic DNA, and 2.5 units of Taq DNA polymerase (New England Biolabs, Ipswich, Mass., USA). The amplification reaction was incubated in an EPPENDORF® MASTERCYCLER® programmed for 1 cycle at 95° C. for 2 minute; 30 cycles each at 95° C. for 30 seconds, 60° C. for 30 seconds, and 72° C. for 40 seconds; and 1 cycle at 72° C. for 15 minutes.

```
Forward primer:
                                      (SEQ ID NO: 78)
5'-AATGACCCATAGGGAGACAAACAGCATAAT-3'

Reverse primer:
                                      (SEQ ID NO: 79)
5'-TGTTGGACGCAGGATTTTGGA-3'
```

The 0.56 kb probe was purified by 1% agarose gel electrophoresis using TAE buffer where a band corresponding to the probe was excised from the gel and extracted using a QIAQUICK® Gel Extraction Kit (Example 1). The probe was boiled for 5 minutes and chilled on ice for 2 minutes, and then added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern blot analysis identified final spore isolates that contained the cbh1 replacement (2.5 kb hybridizing fragment) and did not contain the hpt/tk markers. The native *T. reesei* cbh1 locus produced a 1.9 kb hybridizing fragment.

One spore isolate was chosen as the final strain and designated *T. reesei* DLM-TICBH-9.

Example 6

Repair of the Ku70 Gene in cbh1 and cbh2 Replaced Strain *Trichoderma reesei* DLM-TICBH-9

The native *Trichoderma reesei* ku70 gene was repaired in the *Trichoderma reesei* replacement strain DLM-TICBH-9 (Example 5) in order to facilitate strain manipulation steps requiring the function of the KU70 protein's role in in non-homologous end-joining of DNA. *T. reesei* DLM-TICBH-9 was transformed with 23×2 µg of Pme I-linearized pTH239 (WO 2013/028928) according to the procedure described above in Example 1. Forty-six transformants were obtained and each one was separately transferred to a PDA plate and incubated for 3 days at 30° C.

Spore PCR using a PHIRE® Plant Direct PCR Kit was utilized to identify transformants which had integrated the pTH239 repair cassette at the ku70 locus. Briefly, spores from transformants were collected with a sterile 1 µl inoculation loop and transferred to 20 µl of Kit-supplied dilution buffer in 0.2 ml PCR strip tubes and incubated for 5 minutes at room temperature. The spore suspensions were centrifuged briefly in a strip-fuge mini centrifuge (Sigma Aldrich, St Louis, Mo., USA) and 1.5 µl of each supernatant was used in the spore PCR. The Spore PCR was composed of 1×PHIRE® Plant Direct PCR Buffer (contains dNTPs and Mg), 1.25 µM gene specific forward and reverse primers listed below, and 0.4 µl of PHIRE® II Hot Start DNA Polymerase.

```
Forward primer:
                                      (SEQ ID NO: 80)
5'-CGCTGAAATGCGCCCGCCACCT-3'

Reverse primer:
                                      (SEQ ID NO: 81)
5'-GGGCGGACAGACGGGGCAAA-3'
```

The amplification reactions were incubated in an EPPENDORF® MASTERCYCLER® programmed for 1 cycle at 98° C. for 5 minutes; 40 cycles each at 98° C. for 20 seconds, 61° C. for 20 seconds, and 72° C. for 1 minute; and 1 cycle at 72° C. for 1 minute.

The completed PCRs were subjected to 1% agarose gel electrophoresis using TAE buffer and 40 of the 46 transformants obtained displayed the 1.4 kb band indicative of integration of pTH239 at the ku70 locus. Six transformants were arbitrarily chosen to loop out the hpt/tk markers using 5-fluorodeoxyuridine (FdU) counter-selection. Spores from a 6 day old plate were collected in 10 ml of 0.01% TWEEN® 20 and the spore concentration was determined using a hemocytometer. Spores were diluted to a concentration of $10^6$ spores per ml and $10^6$, $10^5$, and $10^4$ spores were spread onto TrMM-G plates supplemented with 1 µM FdU. Colonies were picked with a sterile 10 µl inoculation loop and transferred to a 75 mm PDA plate and incubated for 3 days at 30° C.

Spore PCR using a PHIRE® Plant Direct PCR Kit was completed to determine if the resulting spore isolates had correctly excised the markers as described above with the forward and reverse primers below.

```
Forward primer:
                                    (SEQ ID NO: 82)
5'-CGCTGAAATGCGCCCGCCACCT-3'

Reverse primer:
                                    (SEQ ID NO: 83)
5'-CGTTCTCGCCGGCGTTTGCC-3'
```

The composition of the PCRs was identical to those described above with the spore solution of the FdU-resistant spore isolates as template and the cycling parameters were as follows: 1 cycle at 98° C. for 5 minutes; 40 cycles each at 98° C. for 20 seconds, 61° C. for 20 seconds, and 72° C. for 3 minutes; and 1 cycle at 72° C. for 3 minutes.

The completed PCRs were subjected to 1% agarose gel electrophoresis using TAE buffer and the results indicated that 25 of the 48 isolates had correctly excised the cassette. Three of the spore isolates were chosen for spore purification to ensure homogeneity. For each spore purification, a 1 µl inoculation loop was lightly touched to an isolate on a PDA plate and transferred to 1 ml of 0.01% TWEEN® 20 in 15 ml conical bottom tube. Each tube was vortexed and a 3 µl aliquot was transferred to a new 150 mm PDA plate and incubated at 30° C. for 2 days. Isolates were picked with a sterile 10 µl inoculation loop and transferred to a new PDA plate and incubated at 30° C. for 3 days. Spore PCR was repeated to ensure that the isolates picked contained the repaired ku70 locus and were homogeneous. One randomly selected isolate, designated JfyS99-19B4, was analyzed by Southern blot analysis to verify the results of the spore PCR suggesting strains were all homozygous for the deletion and had correctly excised the markers, Southern blot analysis was then used on the resulting spore progeny. Genomic DNA was generated as described above in Example 1, and 2 µg were digested with Nco I. DNA was subjected to 1% agarose gel electrophoresis and transferred to a NYTRAN® membrane as described in Example 1. A probe hybridizing to the 3' flank of the ku70 gene was generated as described in Example 1 with the following region-specific forward and reverse primers below.

```
Forward primer:
                                    (SEQ ID NO: 84)
5'-CAGAGAAAGGTAGCTGGAGAGC-3'

Reverse primer:
                                    (SEQ ID NO: 85)
5'-GTCCATTTCGATTCCGCATAG-3'
```

The above probe was used for hybridization and subsequent detection of probe-DNA hybrids as described in Example 1. The results of the Southern blot analysis confirmed the results of the spore PCR above suggesting that the strains had correctly excised the markers, and that the ku70 gene sequence was no longer disrupted. One of the strains, designated *Trichoderma reesei* JfyS99-19B4, was arbitrarily selected for expression of different possible combinations of cellulases described herein.

Example 7

Construction of an AA9 (GH61A) Polypeptide Expression Vector pQM35

Plasmid pQM35 was constructed to comprise an AA9 (GH61A) polypeptide expression cassette under control of the *Trichoderma reesei* cbh2 promoter and terminator. The AA9 polypeptide coding sequence (SEQ ID NO: 7 [DNA sequence] and SEQ ID NO: 8 [amino acid sequence]) was amplified from plasmid pDM286 (WO 2013/028912) using gene-specific forward and reverse primers (1205256 and 1205257) shown below. The *Trichoderma reesei* cbh2 terminator was amplified from *Trichoderma reesei* RutC30 genomic DNA using the gene specific forward and reverse primers (1205258 and 1205259) shown below.

```
1205256 (InF-PeGH61-F):
                                    (SEQ ID NO: 86)
ATCACCCTCTGTGTATTGCACCATGCTGTCTTCGACGACTCGC 1205257 (InF-PeGH61-R):
                                    (SEQ ID NO: 87)
GCCCGGTCACGAAAGCCTTATCGACTTCTTCTAGAACGTCGGC 1205258 (InF-TrCbh2Term-F):
                                    (SEQ ID NO: 88)
GCCGACGTTCTAGAAGAAGTCGATAAGGCTTTCGTGACCGGGC 1205259 (InF-TrCBH2 Term-R):
                                    (SEQ ID NO: 89)
CAGGTGTCAGTCACCTCTAGTTAATTAACTCGGAGTTGTTATACGCTA
CTCG
```

The amplification reaction was composed of 100 ng of template, 1 µl of 10 mM dNTP's, 50 µmol of each forward and reverse primer, 1×PHUSION® GC Buffer (New England Biolabs, Ipswich, Mass., USA), and 1 unit of PHUSION® High-Fidelity Hot Start DNA polymerase in a final volume of 50 µl. The amplification reaction was incubated in an EPPENDORF® MASTERCYCLER® programmed for 1 cycle at 98° C. for 2 minutes; 35 cycles each at 98° C. for 15 seconds, 60° C. for 30 seconds, and 72° C. for 1 minute; and 1 cycle at 72° C. for 10 minutes. The PCR products were separated by 0.7% agarose gel electrophoresis using TAE buffer where a 1 kb AA9 polypeptide gene fragment and a 353 bp *Trichoderma reesei* cbh2 terminator fragment were excised from the gel and extracted using a NUCLEOSPIN® Gel and PCR Clean-Up Kit. Briefly, 2 volumes of Buffer NT1 were added to the gel slice and dissolved for 10 minutes at 50° C. after which the entire solution was transferred to a Kit-supplied centrifugal column. The column was centrifuged at 13,000 rpm for 1 minute, and washed with wash buffer NT3 and recentrifuged. DNA was eluted with 20 µl of Kit-supplied elution buffer and centrifuged at 13,000 rpm for 1 minute The purified AA9 polypeptide coding sequence and *Trichoderma reesei* cbh2 terminator were combined in a SOE PCR using primer 1205256 and 1205259. The SOE PCR was composed of 10 ng of the 887 bp purified AA9 polypeptide gene fragment amplified from pDM286, 10 ng of the 353 bp purified *Trichoderma reesei* cbh2 terminator fragment, 1 µl of 10 mM dNTP's, 1×PHUSION™ HF Buffer, and 1 unit of PHUSION™ High-Fidelity Hot Start DNA Polymerase in a final volume of 45 µl. The amplification reaction was incubated in an EPPENDORF® MASTERCYCLER® programmed for 1 cycle at 98° C. for 2 minutes; and 5 cycles each at 98° C. for 15 seconds, 60° C. for 30 seconds, and 72° C. for 1 minute and 30 seconds. A mixture containing 1×PHUSION™ H Buffer and 50 pmol of each forward and reverse primer in a total volume of 5 µl was added to the SOE PCR and continued for 35 cycles each at 98° C. for 15 seconds, 60° C. for 30 seconds, and 72° C. for 1 minute and 30 seconds; and 1 cycle at 72° C. for 10 minutes. The SOE PCR product was purified using a NUCLEOSPIN® Gel and PCR Clean-Up Kit.

Figure 5:
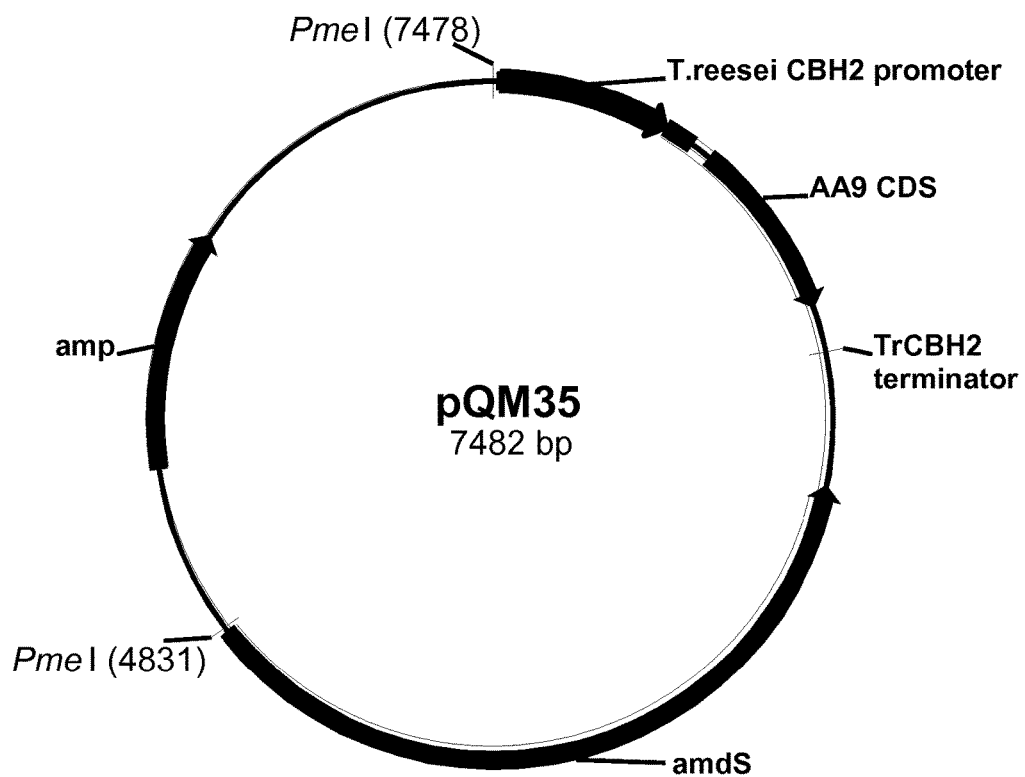
FIG. 5 shows a restriction map of plasmid pQM35.

The purified SOE PCR product was inserted into Pac I and Nco I digested pAG121 (Example 10) using an IN-FU- SION™ HD Cloning Kit (Clontech, Palo Alto, Calif., USA). The reaction (10 µl) was composed of 1× IN-FUSION™ HD enzyme mix, 150 ng of pAG121 digested with Nco I and Pac I, and 57 ng of the purified SOE PCR product. The reaction was incubated for 15 minutes at 50° C. Then 2.5 µl of the cloning reaction were transformed into ONE SHOT® TOP10 competent cells by addition to a single use tube containing the competent cells and incubating the cells on ice for 5 minutes. The tube was incubated at 42° C. for 30 seconds after which 250 µl of SOC medium were added. The tube was then incubated at 37° C. with mixing at 200 rpm for 1 hour and 250 µl were transferred to a 150 mm 2XYT+Amp plate and incubated overnight at 37° C. Plasmid DNA was isolated from the resulting transformants using a Plasmid Mini Kit. A plasmid containing the insert with no PCR errors confirmed by DNA sequencing using an Applied Biosystems 377 XL Automated DNA Sequencer and dye-terminator chemistry (Giesecke et al., 1992, supra) was designated pQM35 (FIG. 5).

Example 8

Construction of Plasmid pSMai139

To construct pSMai139, the *Humicola insolens* endoglucanase V full-length coding region was PCR amplified from pMJ05 (US 2004/0248258) as template with the primers shown below. The underlined portions are a Sph I site and a Hind III site introduced by the Car-F2 sense primer. The bold portion is an Eco RI site introduced by the Car-R2 antisense primer.

```
Car-F2 sense primer:
                                        (SEQ ID NO: 90)
5'-TATAAGCTTAAGCATGCGTTCCTCCCCCCTC-3'

Car-R2 antisense primer:
                                        (SEQ ID NO: 91)
5'-CTGCAGAATTCTACAGGCACTGATGGTACCAG-3'
```

The amplification reaction (50 µl) was composed of 1× ThermoPol Reaction Buffer (New England Biolabs, Inc., Ipswich, Mass. USA), 0.3 mM dNTPs, 10 ng of pMJ05 DNA, 0.3 µM Car-F2 sense primer, 0.3 µM Car-R2 antisense primer, and 2.5 units of VENT® DNA polymerase (New England Biolabs, Inc., Ipswich, Mass. USA). The reaction was incubated in an EPPENDORF® MASTERCYCLER® 5333 epgradient S programmed for 30 cycles each at 94° C. for 30 seconds, 55° C. for 30 seconds, and 72° C. for 60 seconds (15 minute final extension). The reaction product was isolated by 1.0% agarose gel electrophoresis using TAE buffer where a 900 bp product band was excised from the gel and purified using a QIAQUICK® Gel Extraction Kit (Example 1). The 900 bp PCR fragment was then digested with Eco RI and Hind III and subjected to a QIAQUICK® PCR Purification Kit (Example 4). Plasmid pMJ05 was digested with Eco RI and Hind III, isolated by 0.7% agarose gel electrophoresis using TAE buffer, excised from the gel, and extracted using a QIAQUICK® Gel Extraction Kit (Example 1).

Figure 6:
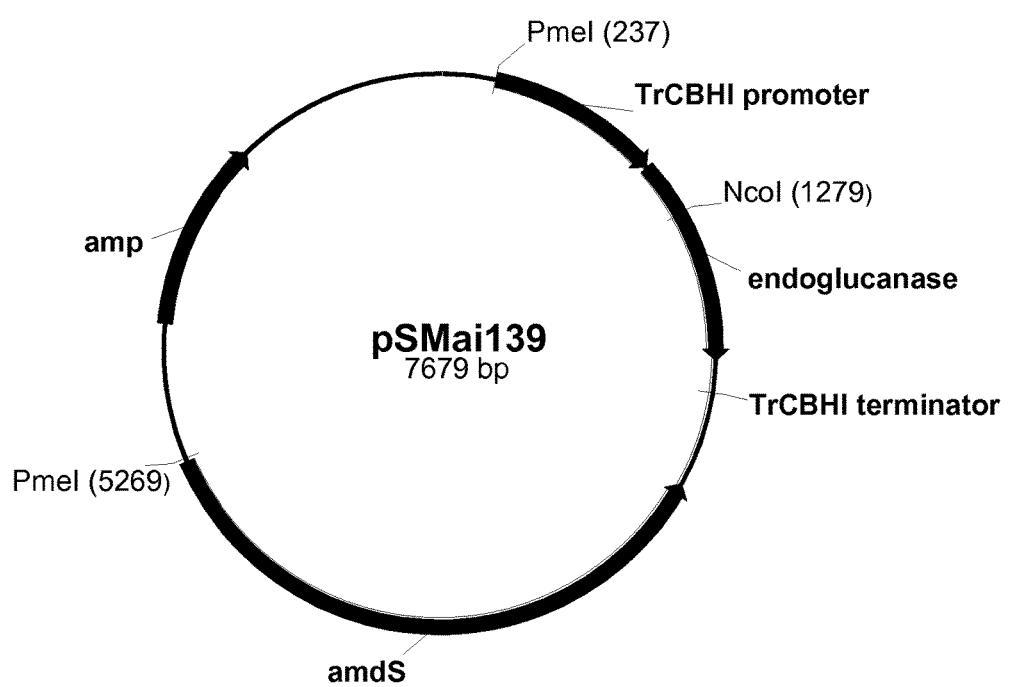
FIG. 6 shows a restriction map of plasmid pSMai139.

The 900 bp Eco RI and Hind III digested PCR fragment were ligated into Eco RI and Hind III digested pMJ05 using T4 DNA ligase (Roche, Indianapolis, Ind., USA). The ligation reaction was composed of 50 ng of the Eco RI and Hind III digested pMJ05, 33 ng of the Eco RI and Hind III digested 0.9 kb PCR fragment, 1× Ligase Buffer (Roche, Indianapolis, Ind., USA), and 2 units of T4 DNA ligase in a final volume of 20 µl. The reaction was incubated at 15° C. for 17 hours and 2 µl of the reaction were transformed into ONE SHOT® TOP10 competent cells by addition to a single use tube containing the competent cells and incubating the cells on ice for 5 minutes. The tube was incubated at 42° C. for 30 seconds after which 250 µl of SOC medium were added. The tube was then incubated at 37° C. with mixing at 200 rpm for 1 hour and 250 µl were transferred to a 150 mm 2XYT+Amp plate and incubated overnight at 37° C. The resulting transformants were screened by restriction digestion analysis with Sph I and Bam HI to determine the presence and orientation of the insert and positive clones were sequenced using an Applied Biosystems 377 XL Automated DNA Sequencer and dye-terminator chemistry (Giesecke et al., 1992, supra). A clone containing the *Humicola insolens* endoglucanase V coding region with no PCR errors was designated pSMai139 (FIG. 6).

Example 9

Construction of Plasmid pSMai143

Plasmid pSMai143 was constructed by amplifying 620 bp of the *Trichoderma reesei* cellobiohydrolase Cel6A promoter from *Trichoderma reesei* RutC30 genomic DNA using primers 994148 and 994149 shown below. The underlined portion is a Sal I site introduced by primer 994148. The bold portion is a "CAT" sequence introduced by primer 994149.

```
Primer 994148:
                                        (SEQ ID NO: 92)
5'-ACGCGTCGACGAATTCTAGGCTAGGTATGCGAGGCA-3'

Primer 994149:
                                        (SEQ ID NO: 93)
5'-CATGGTGCAATACACAGAGGGTG-3'
```

The amplification reaction (50 µl) was composed of 1× ThermoPol Reaction Buffer, 0.3 mM dNTPs, 100 ng of *Trichoderma reesei* RutC30 genomic DNA, 0.3 µM 994148 sense primer, 0.3 µM 994149 antisense primer, and 2.5 units of Vent DNA polymerase. The reactions were incubated in an EPPENDORF® MASTERCYCLER® 5333 epgradient S programmed for 30 cycles each at 94° C. for 60 seconds, 55° C. for 60 seconds, and 72° C. for 60 seconds (15 minute final extension). The reaction products were isolated by 1.0% agarose gel electrophoresis using TAE buffer where a 620 bp product band was excised from the gel and purified using a QIAQUICK® Gel Extraction Kit (Example 1).

Plasmid pSMai139 was digested with Sph I and the 3'-protruding end was blunted with T4 DNA polymerase followed by digestion with Sal I. The digested DNA was isolated by 0.7% agarose gel electrophoresis using TAE buffer, excised from the gel, and extracted using a QIAQUICK® Gel Extraction Kit (Example 1).

Figure 7:
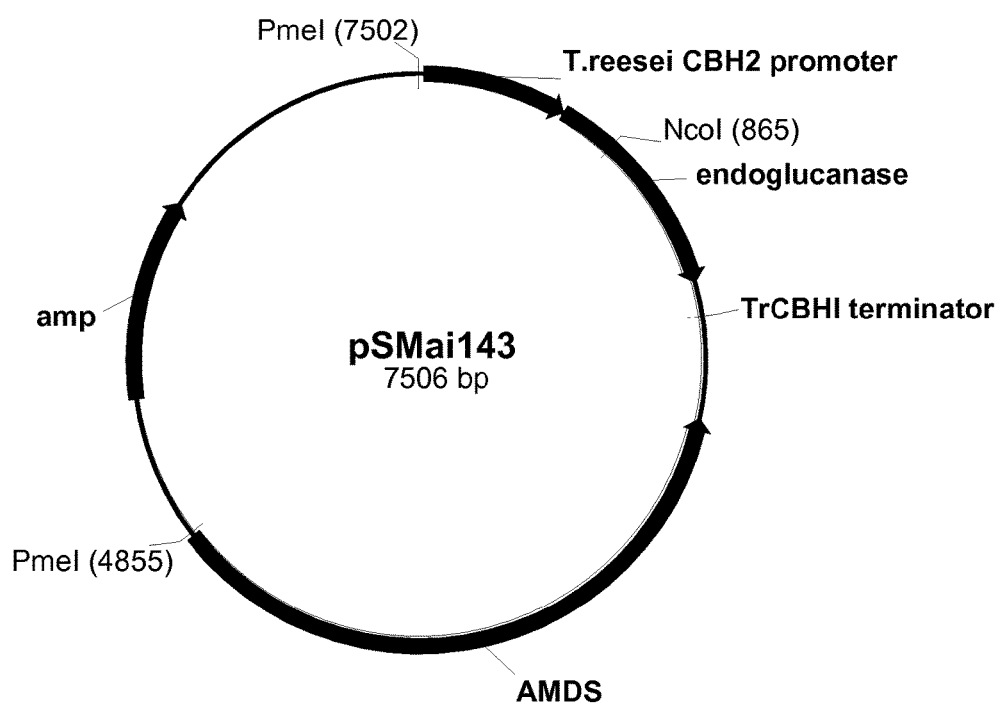
FIG. 7 shows a restriction map of plasmid pSMai143.

The 620 bp Sal I digested PCR fragment was ligated into Sph I and Sal I digested pSMai139 using T4 DNA ligase. The ligation reaction was composed of 50 ng of the Sph I and Sal I digested pSMai139, 22 ng of the Sal I digested 0.62 kb PCR fragment, 1× Ligase Buffer, and 2 units of T4 DNA ligase in a final volume of 20 µl. The reaction was incubated at 15° C. for 17 hours and 2 µl of the reaction were transformed into ONE SHOT® TOP10 competent cells by addition to a single use tube containing the competent cells and incubating the cells on ice for 5 minutes. The tube was incubated at 42° C. for 30 seconds after which 250 µl of SOC medium were added. The tube was then incubated at 37° C. with mixing at 200 rpm for 1 hour and 250 μl were transferred to a 150 mm 2XYT+Amp plate and incubated overnight at 37° C. The resulting transformants were screened by restriction digestion analysis with Eco RI to determine the presence and orientation of the insert and positive clones were sequenced. One clone containing the *Trichoderma reesei* cbh2 promoter with no PCR errors was designated pSMai143 (FIG. 7).

Example 10

Construction of Plasmid pAG121

Expression vector pAG121 with an Nco I restriction site was constructed by performing site-directed mutagenesis on pSMai143 (Example 9) using a QUIKCHANGE® Site-Directed Mutagenesis Kit (Stratagene, La Jolla, Calif., USA) using the primers shown below. The mutagenesis was performed according to manufacturer's recommendations using 20 ng of plasmid pAG121 and 12.5 μM of the primers shown below in a final volume of 50 μl.

```
Smai143 SDM Fwd:
                                  (SEQ ID NO: 94)
gtgtattgcaccatggcgttcctcccccctcc Smai143 SDM Rev:
                                  (SEQ ID NO: 95)
ggagggggaggaacgccatggtgcaataca
```

The resulting variant plasmid pAG121 was prepared using a BIOROBOT® 9600. The variant plasmid construct was sequenced using an Applied Biosystems 3130 xl Genetic Analyzer to verify the changes.

Plasmid pAG122 was constructed to comprise a beta-xylosidase coding sequence (SEQ ID NO: 13 [DNA sequence] and SEQ ID NO: 14 [amino acid sequence]) under the control of the *T. reesei* cbh2 gene promoter and *T. reesei* cbh1 gene terminator.

Two synthetic oligonucleotide primers shown below were designed to PCR amplify the beta-xylosidase coding sequence (SEQ ID NO: 13) contained in plasmid pENI191. An IN-FUSION™ Advantage PCR Cloning Kit (Clontech Laboratories, Inc., Mountain View, Calif., USA) was used to clone the fragment directly into the expression vector pAG121. Bold letters represent coding sequence. The remaining sequence is homologous to the insertion sites of pAG121.

```
Forward primer:
                                  (SEQ ID NO: 96)
5'-CCCTCTGTGTATTGCACCATGATGACTCCCACGGCGAT-3'

Reverse primer:
                                  (SEQ ID NO: 97)
5'-GATCTGCGGCCGCGAATTTTATTGCTGCAGCACCCCCG-3'
```

Fifty picomoles of each of the primers above were used in a PCR composed of 10 ng of pENI191, 1×EXPAND® High Fidelity PCR buffer with MgCl₂ (Roche Applied Science, Penzberg, Germany), 0.25 mM each of dATP, dTTP, dGTP, and dCTP, and 2.6 units of EXPAND® High Fidelity Enzyme Mix (Roche Applied Science, Penzberg, Germany) in a final volume of 50 μl. The amplification was performed using an EPPENDORF® MASTERCYCLER® 5333 epgradient S programmed for 1 cycle at 94° C. for 2 minutes; 30 cycles each at 94° C. for 15 seconds, 60.5° C. for 30 seconds, and 72° C. for 2 minutes; and a final elongation at 72° C. for 15 minutes. The heat block then went to a 4° C. soak cycle. The reaction products were isolated by 1% agarose gel electrophoresis using TAE buffer where an approximately 2.4 kb product band was observed on the gel. The PCR product was purified using a MINELUTE® Gel Extraction Kit. Briefly, 3 volumes of Kit-supplied buffer QG were added to a gel slice and dissolved at 50° C. for approximately 10 minutes. The dissolved gel slice was applied to a Kit-supplied spin column and centrifuged at 13,000 rpm for 1 minute. The column was washed with 750 μl of Kit-supplied buffer PE and then re-centrifuged. DNA was eluted with 10 μl of Kit-supplied buffer EB. Plasmid pAG121 was digested with Nco I and Kpn I and isolated by 1.0% agarose gel electrophoresis using TAE buffer where a 6.6 kb band was excised from the gel and extracted using a QIAQUICK® Gel Extraction Kit (Example 1).

Figure 8:
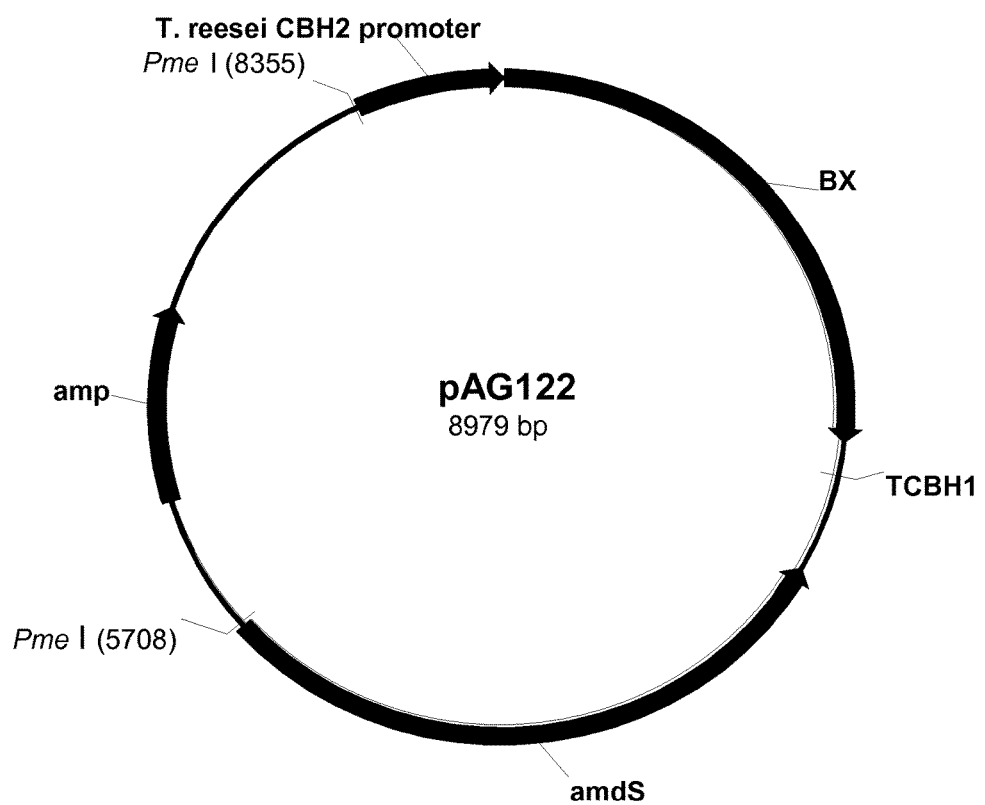
FIG. 8 shows a restriction map of plasmid pAG122.

The 2.4 kb gene fragment and the 6.6 kb digested vector were ligated together using an IN-FUSION® Advantage PCR Cloning Kit resulting in pAG122. The reaction (20 μl) was composed of 1× IN-FUSION™ Reaction Buffer (Clontech Laboratories, Inc., Mountain View, Calif., USA), 1×BSA, 1 μl of IN-FUSION™ enzyme (Clontech Laboratories, Inc., Mountain View, Calif., USA) (diluted 1:10), 100 ng of the gel-purified Nco I/Pac I digested pMJ09, and 42 ng of the purified 1.05 kb PCR product. The reaction was incubated at 37° C. for 15 minutes followed by 50° C. for 15 minutes. After diluting the reaction mix with 50 μl of TE buffer, 2.5 μl of the reaction was transformed into *E. coli* XL10 SOLOPACK® Gold Supercompetent cells (Stratagene, La Jolla, Calif., USA). The *E. coli* transformation reactions were spread onto 2XYT plus ampicillin plates. Plasmid DNA was prepared using a BIOROBOT® 9600. The beta-xylosidase coding sequence insert was confirmed in one plasmid by DNA sequencing using an Applied Biosystems 377 XL Automated DNA Sequencer and dye-terminator chemistry (Giesecke et al., 1992, supra). The plasmid was designated pAG122 (FIG. 8).

Example 11

Construction of a Xylanase Expression Vector pAgJg131

Plasmid pAgJg131 was constructed to comprise the *Trichoderma reesei* cellobiohydrolase 1 gene promoter and terminator and a xylanase coding sequence (SEQ ID NO: 9 [DNA sequence] and SEQ ID NO: 10 [amino acid sequence]). Two synthetic oligonucleotide primers shown below were designed to PCR amplify the xylanase gene from plasmid P24F62 (WO 2013/019827) and introduce flanking regions for insertion into expression vector pMJ09 (WO 05/056772). Bold letters represent coding sequence and the remaining sequence is homologous to the insertion sites of plasmid pMJ09.

```
Forward Primer:
                                  (SEQ ID NO: 98)
5'-CCGCGGACTGCGCACCATGGTCCATCTTTCTTCCCT-3'

Reverse Primer:
                                  (SEQ ID NO: 99)
5'-TTCGCCACGGAGCTTATTACAGGCACTGGTAGTAGT-3'
```

The amplification reaction was composed of 64.2 ng of plasmid P24F62, 10 μl of 10 mM dNTP's, 50 μmol of each forward and reverse primer, 1×PHUSION® GC Buffer, and 2 units of PHUSION® High-Fidelity Hot Start DNA polymerase in a final volume of 50 µl. The amplification reaction was incubated in an EPPENDORF® MASTERCYCLER® programmed for 1 cycle at 98° C. for 30 seconds; 30 cycles each at 98° C. for 10 seconds, 61° C. for 10 seconds, and 72° C. for 45 seconds; and 1 cycle at 72° C. for 10 minutes. PCR products were separated by 1% agarose gel electrophoresis using TAE buffer where a 1.5 kb fragment was excised from the gel and extracted using a QIAQUICK® Gel Extraction Kit (Example 1).

Figure 9:
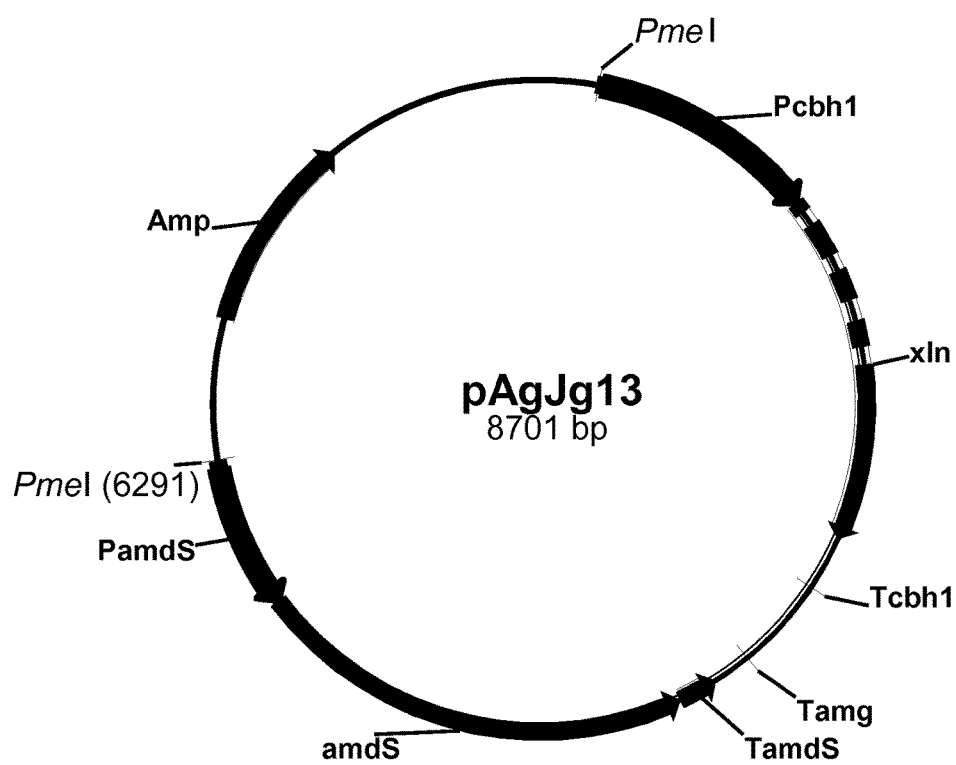
FIG. 9 shows a restriction map of plasmid pAgJg131.

The fragment was then cloned into pMJ09 using an IN-FUSION™ HD Cloning Kit. Plasmid pMJ09 was digested with Nco I and Pac I. The vector was isolated by 1% agarose gel electrophoresis using TAE buffer where a 7.2 kb fragment was excised from the gel and extracted using a QIAQUICK® Gel Extraction Kit (Example 1). The 1.5 kb gene fragment and the digested vector were ligated together in a reaction resulting in the expression plasmid pAgJg131 in which transcription of the xylanase gene was under the control of the *T. reesei* cbh1 promoter. The ligation reaction (10 µl) was composed of 1× IN-FUSION™ HD enzyme mix (Clontech, Palo Alto, Calif., USA), 213 ng of pMJ09 digested with Nco I and Pac I, and 106 ng of the xylanase purified PCR product. The reaction was incubated for 15 minutes at 50° C. A 2.5 µl volume of the cloning reaction was used to transform ONE SHOT® TOP10 competent cells by addition to a single use tube containing the competent cells and incubating the cells on ice for 5 minutes. The tube was incubated at 42° C. for 30 seconds after which 250 µl of SOC medium were added. The tube was then incubated at 37° C. with mixing at 200 rpm for 1 hour and 250 µl were transferred to a 150 mm 2XYT+Amp plate and incubated overnight at 37° C. Plasmid DNA was isolated from the resulting transformants using a QIAprep Mini Prep Kit (QIAGEN Inc., Valencia, Calif., USA). The insert was confirmed by DNA sequencing using an Applied Biosystems 377 XL Automated DNA Sequencer and dye-terminator chemistry (Giesecke et al., 1992, supra). The resulting plasmid was designated pAgJg131 (FIG. 9).

Example 12

Construction of Catalase Expression Vector pLAQ564

A DNA sequence was designed to encode the amino acid sequence of a catalase (SEQ ID NO: 33 [DNA sequence] and SEQ ID NO: 34 [amino acid sequence]). The gene was specifically designed for expression in *Aspergillus oryzae* and a restriction site was added at either end to ease cloning. The DNA was subsequently synthesized by a commercial provider.

Figure 10:
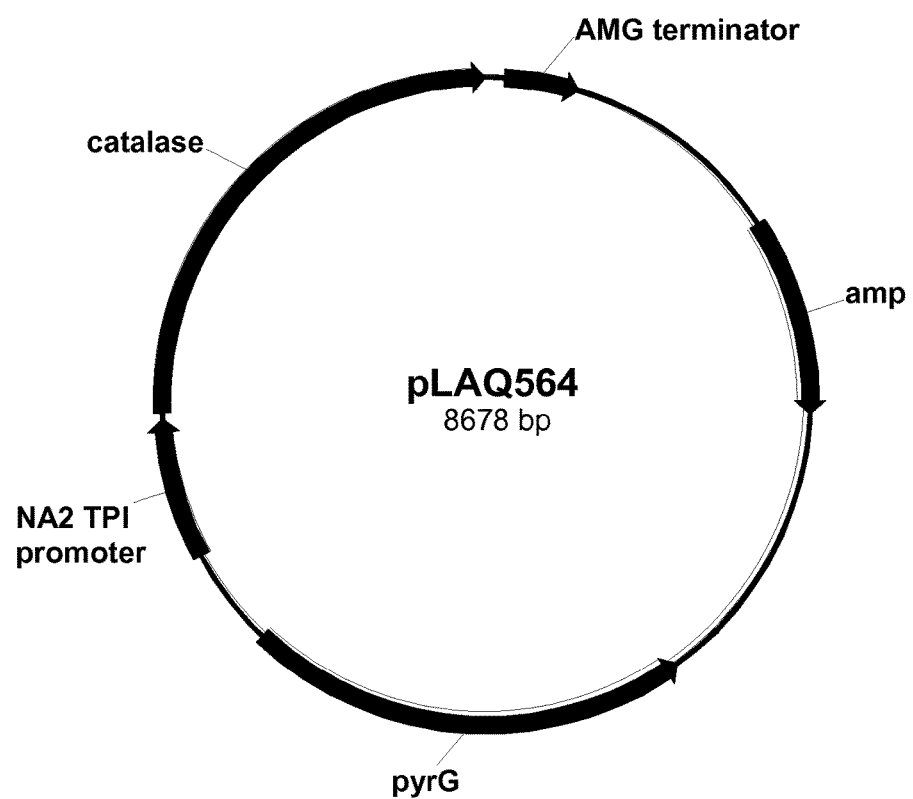
FIG. 10 shows a restriction map of plasmid pLAQ564.

The synthetic gene (SEQ ID NO: 100) encoding the catalase was ligated into the multiple cloning site of plasmid pENI2516 (U.S. Pat. No. 7,871,800) as a Not I-Xho I fragment to generate construct pLAQ564 using T4 DNA ligase. The constructed plasmid was transformed into ONE SHOT® TOP10 competent cells. Plasmid DNA was isolated using a QIAprep Mini Prep Kit. The insert was confirmed by DNA sequencing using an Applied Biosystems 377 XL Automated DNA Sequencer and dye-terminator chemistry (Giesecke et al., 1992, supra). The resulting plasmid was designated pLAQ564 (FIG. 10).

Example 13

Construction of Catalase Expression Vector pSaMe-TaCat

Plasmid pSaMe-TaCat was constructed to comprise the catalase coding sequence of SEQ ID NO: 33 operably linked to the *Trichoderma reesei* cellobiohydrolase I gene promoter and terminator. Two synthetic oligonucleotide primers shown below were designed to PCR amplify the catalase gene from plasmid pLAQ564 and introduce flanking regions for insertion into expression vector pMJ09 (WO 05/056772). Bold letters represent coding sequence and the remaining sequence is homologous to the insertion sites of pMJ09.

```
Forward Primer:
                                 (SEQ ID NO: 101)
5'-CGGACTGCGCACCATGCGAGCAATCGGCTTGTT-3'

Reverse Primer:
                                 (SEQ ID NO: 102)
5'-TCGCCACGGAGCTTATCACTCGGCGTCTTCGTCGA-3'
```

The amplification reaction was composed of 50 ng of plasmid pLAQ564, 200 µm dNTP's, 0.4 µM primers, 1×PHUSION® GC Buffer, and 2 units of PHUSION® DNA polymerase in a final volume of 50 µl. The reaction was incubated in an EPPENDORF® MASTERCYCLER® programmed for 1 cycle at 98° C. for 30 seconds; 30 cycles each at 98° C. for 15 seconds, 60° C. for 15 seconds, and 72° C. for 45 seconds; and 1 cycle at 72° C. for 7 minutes. PCR products were separated by 1% agarose gel electrophoresis using TAE buffer where a 2.2 kb fragment was excised from the gel and extracted using a NUCLEOSPIN® Extract II Kit (Example 2).

Figure 11:
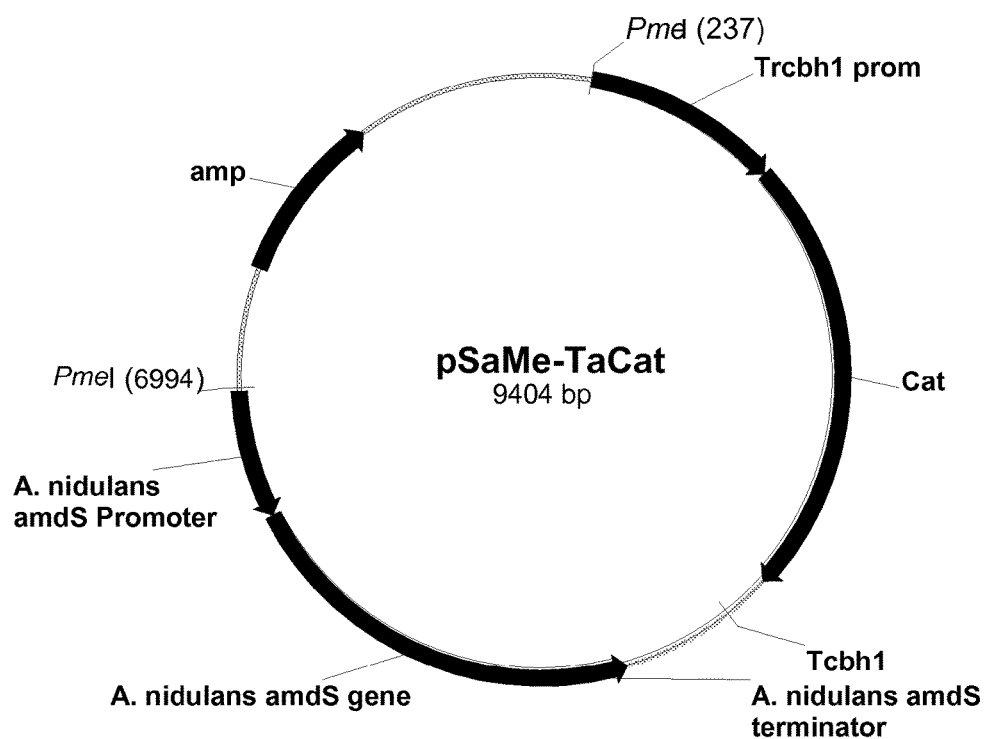
FIG. 11 shows a restriction map of plasmid pSaMe-TaCat.

The fragment was then cloned into pMJ09 using an IN-FUSION™ HD Cloning Kit. The vector was digested with Nco I and Pac I and purified by agarose gel electrophoresis as described above. The 2.2 kb gene fragment and the digested vector were ligated together in a reaction resulting in the expression plasmid pSaMe-TaCat in which transcription of the catalase gene was under the control of the *T. reesei* cbh1 promoter. The ligation reaction (10 µl) was composed of 1× IN-FUSION™ HD enzyme mix, 200 ng of pMJ09 digested with Nco I and Pac I, and 122 ng of the catalase purified PCR product. The reaction was incubated for 15 minutes at 37° C. and 15 minutes at 50° C. To the reaction 40 µl of TE were added. Two µl were used to transform ONE SHOT® TOP10 competent cells by addition to a single use tube containing the competent cells and incubating the cells on ice for 5 minutes. The tube was incubated at 42° C. for 30 seconds after which 250 µl of SOC medium were added. The tube was then incubated at 37° C. with mixing at 200 rpm for 1 hour and 250 µl were transferred to a 150 mm 2XYT+Amp plate and incubated overnight at 37° C. Plasmid DNA was isolated from the resulting transformants using a BIOROBOT® 9600. The insert was confirmed by DNA sequencing using an Applied Biosystems 377 XL Automated DNA Sequencer and dye-terminator chemistry (Giesecke et al., 1992, supra). The resulting plasmid was designated pSaMe-TaCat (FIG. 11).

Example 14

Construction of Beta-glucosidase Expression Vectors

Plasmid pEJG107 is described in WO 05/047499 and comprises a beta-glucosidase coding sequence (SEQ ID NO: 5 [DNA sequence] and SEQ ID NO: 6 [amino acid sequence]) operably linked to the *T. reesei* cbh1 gene promoter and terminator. Plasmid pDFng133-3 is described in WO 2013028912 and comprises a beta-glucosidase variant coding sequence (SEQ ID NO: 35 [DNA sequence] and SEQ ID NO: 36 [amino acid sequence]) operably linked to the *T. reesei* cbh1 gene promoter and terminator.

Example 15

Construction of Plasmid pSaMe-TsGH10

Plasmid pSaMe-TsGH10 was constructed to comprise a GH10 xylanase coding sequence (SEQ ID NO: 11 [DNA sequence] and SEQ ID NO: 12 [amino acid sequence]) under the control of the *Trichoderma reesei* cellobiohydrolase I gene promoter and terminator. Two synthetic oligonucleotide primers shown below were designed to PCR amplify the GH10 coding sequence from plasmid pDAU81#5 (WO 2011/057083) and introduce flanking regions for insertion into expression vector pMJ09 (WO 2005/056772). Bold letters represent coding sequence and the remaining sequence is homologous to the insertion sites of pMJ09.

```
Forward Primer:
                                          (SEQ ID NO: 103)
5'-CGGACTGCGCACCATGCGTACCTTCTCGTCTCTT-3'

Reverse Primer:
                                          (SEQ ID NO: 104)
5'-TCGCCACGGAGCTTATCAAGCCGCAAGAGCAGACG-3'
```

Cloning of the xylanase followed the overall expression cloning protocol described below:

Fifty picomoles of each of the primers above were used in a PCR composed of 50 ng of plasmid DNA from pDAU81 #5, 1 μl of a 10 mM blend of dATP, dTTP, dGTP, and dCTP, 5 μl of 10×PLATINUM® Pfx DNA Polymerase Buffer (Invitrogen, Carlsbad, Calif., USA), and 1 unit of PLATINUM® Pfx DNA Polymerase (Invitrogen, Carlsbad, Calif., USA) in a final volume of 50 μl. An EPPENDORF® MASTERCYCLER® 5333 (Eppendorf Scientific, Inc., Westbury, N.Y., USA) was used to amplify the DNA fragment programmed for 1 cycle at 94° C. for 2 minutes; and 30 cycles each at 94° C. for 15 seconds, 55° C. for 30 seconds, and 68° C. for 1 minute. After the 30 cycles, the reaction was incubated at 72° C. for 10 minutes and then cooled to 4° C. until further processing.

The reaction products were isolated by 1.0% agarose gel electrophoresis using TAE buffer where a 1.2 kb product band was excised from the gel and purified using a QIAQUICK® Gel Extraction Kit.

The 1.2 kb fragment was then cloned into pMJ09 using an IN-FUSION™ Advantage PCR Cloning Kit. The vector was digested with Nco I and Pac I and purified by agarose gel electrophoresis as described above. The gene fragment and the digested vector were ligated together in a reaction resulting in the expression plasmid pSaMe-TsGH10 in which transcription of the xylanase coding sequence of SEQ ID NO: 11 was under the control of the *T. reesei* cbh1 gene promoter and terminator. The ligation reaction (50 μl) was composed of 1× IN-FUSION™ Reaction Buffer, 1×BSA, 1 μl of IN-FUSION™ enzyme (diluted 1:10), 100 ng of pMJ09 digested with Nco I and Pac I, and 100 ng of the xylanase purified PCR product. The reaction was incubated at room temperature for 30 minutes. One μl of the reaction was used to transform *E. coli* XL10 SOLOPACK® Gold cells. Transformants were selected on LB+Amp plates. An *E. coli* transformant containing pSaMe-TsGH10 was detected by restriction enzyme digestion with Nco I and Kpn I and plasmid DNA was prepared using a BIOROBOT® 9600. DNA sequencing of the xylanase coding sequence from pSaMe-TsGH10 was performed using an Applied Biosystems 3130 xl Genetic Analyzer and dye-terminator chemistry (Giesecke et al., 1992, supra) to confirm the correct sequence and completion of construct pSaMe-TsGH10.

Example 16

Construction of Recombinant Filamentous Fungal Strains for Producing Enzyme Compositions Production strains for the enzyme compositions of the present invention are constructed by transforming one or more filamentous fungal host cells, e.g., *Trichoderma reesei* JfyS99-19B4 (Example 6), with one or more of the nucleic acid constructs and/or expression vectors described herein. Protoplast preparation and transformation are performed by any method known in the art such as one of the methods described herein involving protoplast formation, transformation of the protoplasts, and regeneration of the cell wall. Transformants are selected using a suitable selective medium, e.g., COVE plates for amdS selection. The transformants are then grown in a suitable enzyme production medium, e.g., CIM, and supernatants of the culture broths are assayed for enzyme activity and analyzed by SDS-PAGE using the methods described herein. The strains are then fermented in a suitable enzyme production medium to produce the enzyme compositions.

Example 17

Determination of the BCA-equivalent Protein Composition of Monocomponents, Broths and Mixtures of Broths Achieved by BCA Assay and Stain Free Gel Quantitation Samples of protein broths, mixtures of protein broths, and monocomponent proteins were quantified by BCA protein assays and by gel electrophoresis. First, all samples were desalted to remove interfering salts and buffers. This was achieved by equilibration of ECONOPAC® 10DG gravity flow desalt columns (Bio-Rad Laboratories, Inc., Hercules, Calif., USA) with 50 mM sodium acetate pH 5 as column buffer, followed by application of 3 ml of solution containing the protein of interest followed by capture of the desalted sample by elution with 4 ml of column buffer. Diluted samples were measured using a BCA™ Protein Assay Kit (Thermo Fischer Scientific, Waltham, Mass., USA) calibrated by protein standard dilutions of 2.0 mg/mL BSA (Thermo Fischer Scientific, Waltham, Mass., USA). The combined method of desalting and BCA assay is called "desalt BCA".

TGX Stain Free™ or CRITERION® Stain Free 8-16% gels (Bio-Rad Laboratories, Inc., Hercules, Calif., USA) were loaded with, for example, 10 μg desalted protein from fermentation broths. Additionally molecular weight standards (Bio-Rad Laboratories, Inc., Hercules, Calif., USA; unstained) and dilution series of purified monocomponent standard proteins, measured by desalt BCA, were loaded at between 5 to 0.3125 μg per lane. To improve the gel banding resolution, some samples were first deglycosylated by the addition of 0.2 μl of Endo Hf (New England Biolabs, Ipswich, Mass., USA) and incubation overnight at 37° C. For these samples 6.7 to 10 μg of the broth protein was loaded onto gels. The gels were electrophoresed according to manufacturer's recommendations at 200V until the bromophenol blue dye front reached the bottom of the gel. Gels were rinsed 5 minutes with MilliQ water (Millipore, Billerica, Mass., USA) prior to activation (5 minutes) and scanning in an Image Lab™ Scanner (Bio-Rad Laboratories, Inc., Hercules, Calif., USA). Image Lab protein band densities were quantified using Image Lab 3.0 software (Bio-Rad Laboratories, Inc., Hercules, Calif., USA), creating a "band volume" for each identified protein which represented the total integrated Stain Free staining density of that band, and a "lane volume" which represented the total integrated Stain Free lane gel staining density for that lane. If used, the Stain Free compositional amount for any single protein band was represented by the fractional percentage of that band divided by the total staining in the lane (% Stain Free="band volume"/"lane volume"). For samples where addition of Endo Hf enzyme was made, the band volume for that amount of Endo Hf was subtracted from the lane volume to make an adjusted lane volume that represented the composition without Endo Hf.

Purified monocomponent proteins were used to create band volume vs. BCA protein load response curves where the proteins were added by μg as measured by desalt BCA assay and detected as band volume by Stain Free quantitation. For most proteins the ratio of band volume per μg protein was approximately 500,000. The response of most proteins required no adjustment as they had an equal ratio of band volume per μg protein, within the error of these assays (~5%). If a protein showed a significant deviation from this ratio, a calibration curve was made between the protein's band volume and the loaded μg protein as measured by BCA. This allowed adjustment of the band volume relative to the lane volume.

For example, if enzyme Q with band volume of 320,000 in a lane with volume 2,000,000 shows a ratio of band volume per μg BCA loaded protein Q of 400,000 (4/5ths the expected value of 500,000 seen in Stain Free for typical proteins), the band volume for enzyme Q in the quantitation should be multiplied by 5/4 to predict the correct BCA-equivalent amount (to an adjusted band volume of 400,000), and the lane volume should be increased by 1/4th of the band volume for enzyme Q (2,000,000+1/4*320,000=2,080,000, the adjusted lane volume). This leads to an adjusted BCA-equivalent compositional content for protein Q of 400,000/2,080,000=19.2%.

Similarly, if enzyme Z showed a ratio of band volume per μg BCA protein of 600,000 (6/5ths the expected value), the band volume for enzyme Z should be multiplied by 5/6 to predict the correct BCA equivalent amount, and the lane volume should be decreased by 1/6th of the band volume for enzyme Z.

When the adjustments for BCA-equivalent band volume and lane volume were made for all proteins for which there were purified monocomponents, corrected estimates of BCA-equivalent compositions for all broths can be calculated.

Example 18

Pretreated Corn Stover Hydrolysis Assay

Corn stover was pretreated at U.S. Department of Energy National Renewable Energy Laboratory (NREL) using 4% sulfuric acid (based on biomass) at 190° C. for 6 minutes. The water insoluble solids in the pretreated corn stover (PCS) were composed 60.9% of solids and contained 59.4% cellulose, 5.3% hemicellulose and 27.0% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Hydrolysis of PCS was conducted using 50 ml round-bottom centrifuge tubes (Nalgene, Rochester, N.Y., USA) in a total reaction mass of 19 g. The pH of unwashed PCS slurry was adjusted to either 4.75 or 5.0 with sodium hydroxide and 15.5 g of slurry was placed in centrifuge tubes. Enzyme compositions were prepared and added to the PCS slurry in the tubes along with water and buffer to give hydrolysis reaction conditions of 20% total solids, 50 mM sodium citrate, and various protein loadings (expressed as mg protein per gram of cellulose). All enzyme loadings were evaluated in duplicate. Tubes were capped and placed in a rotisserie incubator at a specific temperature for 5 days (120 hours).

Following hydrolysis, samples were filtered using a 0.22 μm MULTISCREEN® 96-well filter plate (Millipore, Bedford, Mass., USA) and filtrates were frozen at −20° C. if not analyzed immediately. Filtrates were diluted 10-fold by volume in 5 mM $H_2SO_4$, and the sugar concentrations of the diluted filtrates were measured using an HPLC system (1100 Series LC System, Agilent Technologies Inc., Palo Alto, Calif.) equipped with a HyperREZ™ XP; Carbohydrate H+; particle size 8 μm with 8% cross linkage (7.7×300 mm) (Thermo Scientific, Waltham, Mass. USA), 0.2 mm in line filter, an automated well-plate sampler, a gradient pump and a refractive index detector. The mobile phase used was 5 mM sulfuric acid at a flow rate of 1.4 ml/min. Refractive index peaks corresponding to cellobiose, glucose, xylose, arabinose, xylitol, glycerol, and acetate were integrated and quantitated versus calibration standards at different concentrations.

All HPLC data processing was performed using MICROSOFT EXCEL™ software (Microsoft, Richland, Wash., USA). For each hydrolysis sample, the measured glucose concentration was adjusted for the appropriate dilution factor, and the net concentration of enzymatically-produced glucose was determined by subtracting the background glucose concentration in unwashed PCS reactions at zero time points from the glucose concentration in samples after hydrolysis. The overall glucan conversions were calculated based on sugars released from enzymatic hydrolysis and biomass composition of the pretreated feedstock using a method published by Zhu et al. (*Bioresource Technol.* 102 (3): 2897-2903). Duplicate data points were averaged and standard deviation was calculated.

Example 19

Comparison of Enzyme Mix 1 to Cellic® CTec2 in the Hydrolysis of Pretreated Corn Stover An enzyme composition comprising a cellobiohydrolase I of SEQ ID NO: 2, a cellobiohydrolase II of SEQ ID NO: 4, an endoglucanase I of SEQ ID NO: 16, an endoglucanase II of SEQ ID NO: 18, a beta-glucosidase variant of SEQ ID NO: 36, an AA9 (GH61) polypeptide having cellulolytic enhancing activity of SEQ ID NO: 8, a catalase of SEQ ID NO: 34, a GH10 xylanase of SEQ ID NO: 10, and a beta-xylosidase of SEQ ID NO: 14 (designated "enzyme mix 1") was compared to a commercial enzyme Cellic® CTec2 (Novozymes A/S, Bagsvaerd, Denmark). The enzyme compositions were compared on unwashed PCS at 20% TS according to Example 18 with the optimal conditions for each blend. Enzyme mix 1 was hydrolyzed at 55° C. and pH 4.75 whereas Cellic® CTec2 was hydrolyzed at 50° C. and pH 5.0 for 5 days. All compositions were used at 3, 6, 10 and 20 mg protein per g cellulose. The protein concentration of the enzyme compositions was determined using a Microplate BCA™ Protein Assay Kit (Thermo Fischer Scientific, Waltham, Mass., USA) in which bovine serum albumin was used as a protein standard.

Figure 12:
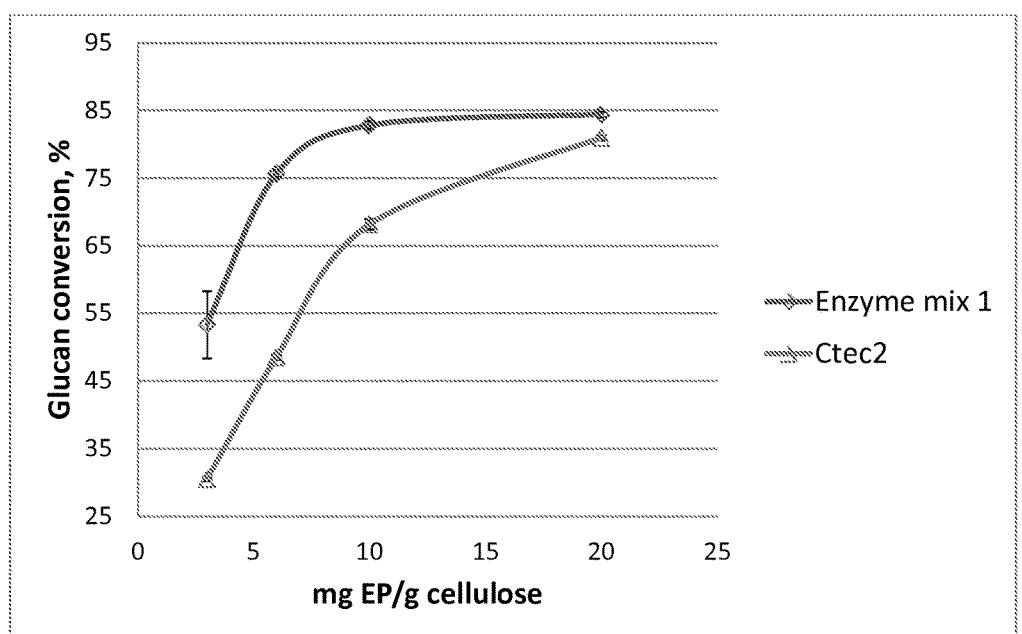
FIG. 12 shows a comparison of percent conversion of glucan (pretreated corn stover) by Cellic® CTec2 to an enzyme composition comprising a cellobiohydrolase I of SEQ ID NO: 2, a cellobiohydrolase II of SEQ ID NO: 4, an endoglucanase of SEQ ID NO: 16, an endoglucanase of SEQ ID NO: 18, a beta-glucosidase variant of SEQ ID NO: 36, an AA9 (GH61) polypeptide having cellulolytic enhancing activity of SEQ ID NO: 8, a catalase of SEQ ID NO: 34, a GH10 xylanase of SEQ ID NO: 10, and a beta-xylosidase of SEQ ID NO: 14 ("enzyme mix 1") at 50° C. and pH 5.0 for 5 days.

The results shown in FIG. 12 demonstrated that "enzyme mix 1" had significantly higher hydrolysis than the commercial enzyme Cellic® CTec2 at all enzyme loadings.

Example 20

Comparison of Enzyme Mix 2 to Cellic® CTec2 in the Hydrolysis of Pretreated Corn Stover An enzyme composition comprising a cellobiohydrolase I of SEQ ID NO: 2, a cellobiohydrolase II of SEQ ID NO: 4, an endoglucanase I of SEQ ID NO: 16, an endoglucanase II of SEQ ID NO: 18, a beta-glucosidase variant of SEQ ID NO: 36, an AA9 (GH61) polypeptide having cellulolytic enhancing activity of SEQ ID NO: 8, a GH10 xylanase of SEQ ID NO: 10, and a beta-xylosidase of SEQ ID NO: 14 (designated "enzyme mix 2") was compared to a commercial enzyme Cellic® CTec2. The enzyme compositions were compared on unwashed PCS at 20% TS according to Example 18 with the optimal conditions for each blend. Enzyme mix 1 was hydrolyzed at 55° C. and pH 4.75 whereas Cellic® CTec2 was hydrolyzed at 50° C. and pH 5.0 for 5 days. All compositions were used at 3, 6, 10 and 20 mg protein per g cellulose. The protein concentration of the enzyme compositions was determined using a Microplate BCA™ Protein Assay Kit in which bovine serum albumin was used as a protein standard.

Figure 13:
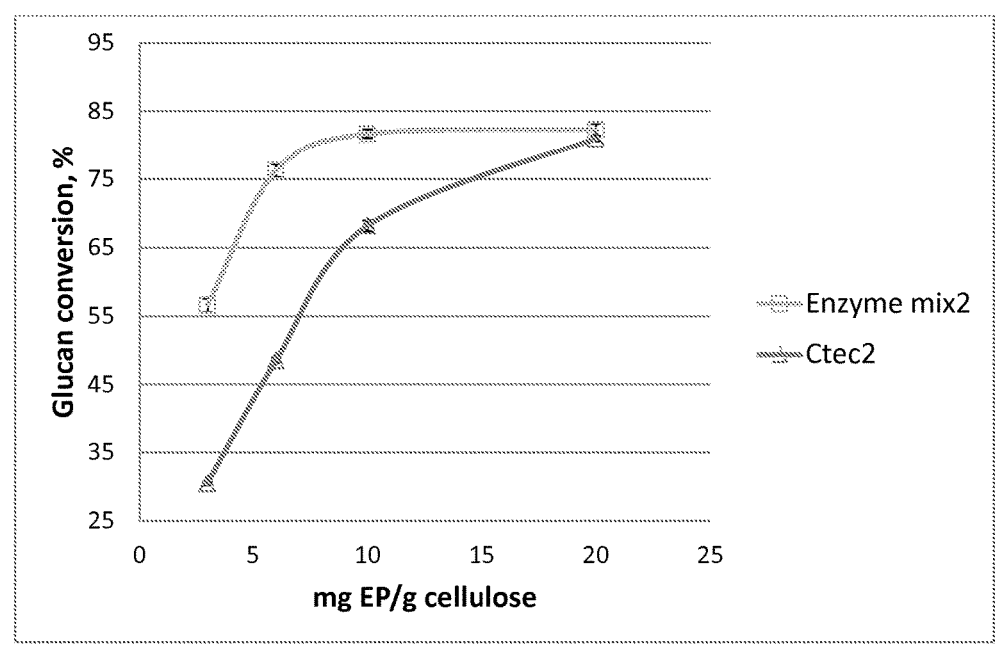
FIG. 13 shows a comparison of percent conversion of glucan (pretreated corn stover) by Cellic® CTec2 to an enzyme composition comprising a cellobiohydrolase I of SEQ ID NO: 2, a cellobiohydrolase II of SEQ ID NO: 4, an endoglucanase of SEQ ID NO: 16, an endoglucanase of SEQ ID NO: 18, a beta-glucosidase variant of SEQ ID NO: 36, an AA9 (GH61) polypeptide having cellulolytic enhancing activity of SEQ ID NO: 8, a GH10 xylanase of SEQ ID NO: 10, and a beta-xylosidase of SEQ ID NO: 14 ("enzyme mix 2") at 50° C. and pH 5.0 for 5 days.

The results shown in FIG. 13 demonstrated that "enzyme mix 2" had significantly higher hydrolysis than the commercial enzyme Cellic® CTec2 at all enzyme loadings.

The present invention is further described by the following numbered paragraphs:

[1] An enzyme composition, comprising: (A) (i) a cellobiohydrolase I, (ii) a cellobiohydrolase II, and (iii) at least one enzyme selected from the group consisting of a beta-glucosidase or a variant thereof, an AA9 polypeptide having cellulolytic enhancing activity, a GH10 xylanase, and a beta-xylosidase; (B) (i) a GH10 xylanase and (ii) a beta-xylosidase; or (C) (i) a cellobiohydrolase I, (ii) a cellobiohydrolase II, (iii) a GH10 xylanase, and (iv) a beta-xylosidase;

wherein the cellobiohydrolase I is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof;

wherein the cellobiohydrolase II is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof;

wherein the beta-glucosidase is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof;

wherein the xylanase is selected from the group consisting of: (i) a xylanase comprising or consisting of the mature polypeptide of SEQ ID NO: 10 or the mature polypeptide of SEQ ID NO: 12; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10 or the mature polypeptide of SEQ ID NO: 12; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the mature polypeptide coding sequence of SEQ ID NO: 11; and (iv) a xylanase encoded by a polynucleotide that hybridizes under at least high stringency conditions, e.g., very high stringency conditions, with the mature polypeptide coding sequence of SEQ ID NO: 9 or the mature polypeptide coding sequence of SEQ ID NO: 11; or the full-length complement thereof; and wherein the beta-xylosidase is selected from the group consisting of: (i) a beta-xylosidase comprising or consisting of the mature polypeptide of SEQ ID NO: 14; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13; and (iv) a beta-xylosidase encoded by a polynucleotide that hybridizes under at least high stringency conditions, e.g., very high stringency conditions, with the mature polypeptide coding sequence of SEQ ID NO: 13 or the full-length complement thereof.

[2] The enzyme composition of paragraph 1, wherein the AA9 polypeptide is any AA9 polypeptide having cellulolytic enhancing activity.

[3] The enzyme composition of paragraph 1 or 2, wherein the AA9 polypeptide having cellulolytic enhancing activity is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[4] The enzyme composition of any of paragraphs 1-3, wherein the beta-glucosidase variant comprises a substitution at one or more positions corresponding to positions 100, 283, 456, and 512 of the full-length polypeptide of SEQ ID NO: 6 or the mature polypeptide thereof, wherein the variant has beta-glucosidase activity.

[5] The enzyme composition of any of paragraphs 1-4, wherein the parent beta-glucosidase of the variant is (a) a polypeptide comprising or consisting of the mature polypeptide of SEQ ID NO: 6; (b) a polypeptide having at least 80% sequence identity to the mature polypeptide of SEQ ID NO: 6; (c) a polypeptide encoded by a polynucleotide that hybridizes under high or very high stringency conditions with (i) the mature polypeptide coding sequence of SEQ ID NO: 5, (ii) the cDNA sequence contained in the mature polypeptide coding sequence of SEQ ID NO: 5, or (iii) the full-length complementary strand of (i) or (ii); (d) a polypeptide encoded by a polynucleotide having at least 80% sequence identity to the mature polypeptide coding sequence of SEQ ID NO: 5 or the cDNA sequence thereof; or (e) a fragment of the mature polypeptide of SEQ ID NO: 6, which has beta-glucosidase activity.

[6] The enzyme composition of any of paragraphs 1-5, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

[7] The enzyme composition of any of paragraphs 1-6, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6.

[8] The enzyme composition of any of paragraphs 1-7, wherein the number of substitutions is 1-4, such as 1, 2, 3, or 4 substitutions.

[9] The enzyme composition of any of paragraphs 1-8, wherein the variant comprises a substitution at a position corresponding to position 100, a substitution at a position corresponding to position 283, a substitution at a position corresponding to position 456, and/or a substitution at a position corresponding to position 512.

[10] The enzyme composition of paragraph 9, wherein the substitution at the position corresponding to position 100 is Asp; the substitution at the position corresponding to position 283 is Gly; the substitution at the position corresponding to position 456 is Glu; and the substitution at the position corresponding to position 512 is Tyr.

[11] The enzyme composition of any of paragraphs 1-10, wherein the variant comprises one or more (e.g., several) substitutions selected from the group consisting of F100D, S283G, N456E, and F512Y.

[12] The enzyme composition of any of paragraphs 1-11, wherein the variant comprises the substitutions F100D+S283G; F100D+N456E; F100D+F512Y; S283G+N456E; S283G+F512Y; N456E+F512Y; F100D+S283G+N456E; F100D+S283G+F512Y; F100D+N456E+F512Y; S283G+N456E+F512Y; or F100D+S283G+N456E+F512Y.

[13] The enzyme composition of any of paragraphs 1-12, wherein the variant comprises or consists of SEQ ID NO: 36 or the mature polypeptide thereof.

[14] The enzyme composition of any of paragraphs 1-13, which comprises the cellobiohydrolase I, the cellobiohydrolase II, and the beta-glucosidase or the variant thereof.

[15] The enzyme composition of any of paragraphs 1-13, which comprises the cellobiohydrolase I, the cellobiohydrolase II, and the AA9 polypeptide having cellulolytic enhancing activity.

[16] The enzyme composition of any of paragraphs 1-13, which comprises the cellobiohydrolase I, the cellobiohydrolase II, and the GH10 xylanase.

[17] The enzyme composition of any of paragraphs 1-13, which comprises the cellobiohydrolase I, the cellobiohydrolase II, and the beta-xylosidase. [18] The enzyme composition of any of paragraphs 1-13, which comprises the cellobiohydrolase I, the cellobiohydrolase II, the beta-glucosidase or the variant thereof, and the AA9 polypeptide having cellulolytic enhancing activity.

[19] The enzyme composition of any of paragraphs 1-13, which comprises the cellobiohydrolase I, the cellobiohydrolase II, the beta-glucosidase or the variant thereof, and the GH10 xylanase.

[20] The enzyme composition of any of paragraphs 1-13, which comprises the cellobiohydrolase I, the cellobiohydrolase II, the beta-glucosidase or the variant thereof, and the beta-xylosidase.

[21] The enzyme composition of any of paragraphs 1-13, which comprises the cellobiohydrolase I, the cellobiohydrolase II, the AA9 polypeptide having cellulolytic enhancing activity, and the GH10 xylanase.

[22] The enzyme composition of any of paragraphs 1-13, which comprises the cellobiohydrolase I, the cellobiohydrolase II, the AA9 polypeptide having cellulolytic enhancing activity, and the beta-xylosidase.

[23] The enzyme composition of any of paragraphs 1-13, which comprises the cellobiohydrolase I, the cellobiohydrolase II, the GH10 xylanase, and the beta-xylosidase.

[24] The enzyme composition of any of paragraphs 1-13, which comprises the cellobiohydrolase I, the cellobiohydrolase II, the beta-glucosidase or the variant thereof, the AA9 polypeptide having cellulolytic enhancing activity, and the GH10 xylanase.

[25] The enzyme composition of any of paragraphs 1-13, which comprises the cellobiohydrolase I, the cellobiohydrolase II, the beta-glucosidase or the variant thereof, the AA9 polypeptide having cellulolytic enhancing activity, and the beta-xylosidase.

[26] The enzyme composition of any of paragraphs 1-13, which comprises the cellobiohydrolase I, the cellobiohydrolase II, the beta-glucosidase or the variant thereof, the GH10 xylanase, and the beta-xylosidase.

[27] The enzyme composition of any of paragraphs 1-13, which comprises the cellobiohydrolase I, the cellobiohydrolase II, the AA9 polypeptide having cellulolytic enhancing activity, the GH10 xylanase, and the beta-xylosidase.

[28] The enzyme composition of any of paragraphs 1-13, which comprises the cellobiohydrolase I, the cellobiohydrolase II, the beta-glucosidase or the variant thereof, the AA9 polypeptide having cellulolytic enhancing activity, the GH10 xylanase, and the beta-xylosidase.

[29] The enzyme composition of any of paragraphs 1-28, which further comprises one or more enzymes selected from the group consisting of a cellulase, an AA9 polypeptide having cellulolytic enhancing activity, a cellulose inducible protein, a hemicellulase, an esterase, an expansin, a laccase, a ligninolytic enzyme, a pectinase, a catalase, a peroxidase, a protease, and a swollenin.

[30] The enzyme composition of paragraph 29, wherein the cellulase is one or more enzymes selected from the group consisting of an endoglucanase, a cellobiohydrolase, and a beta-glucosidase.

[31] The enzyme composition of paragraph 30, wherein the endoglucanase is an endoglucanase I.

[32] The enzyme composition of paragraph 31, wherein the endoglucanase I is a *Trichoderma* endoglucanase I.

[33] The enzyme composition of paragraph 32, wherein the *Trichoderma* endoglucanase I is a *Trichoderma reesei* endoglucanase I or a homolog thereof.

[34] The enzyme composition of any of paragraphs 31-33, wherein the endoglucanase I is selected from the group consisting of: (i) an endoglucanase I comprising or consisting of the mature polypeptide of SEQ ID NO: 16; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15; and (iv) an endoglucanase I encoded by a polynucleotide that hybridizes under at least high stringency conditions, e.g., very high stringency conditions, with the mature polypeptide coding sequence of SEQ ID NO: 15 or the full-length complement thereof.

[35] The enzyme composition of paragraph 30, wherein the endoglucanase is an endoglucanase II.

[36] The enzyme composition of paragraph 35, wherein the endoglucanase II is a *Trichoderma* endoglucanase II.

[37] The enzyme composition of paragraph 36, wherein the *Trichoderma* endoglucanase II is a *Trichoderma reesei* endoglucanase II or a homolog thereof.

[38] The enzyme composition of any of paragraphs 35-37, wherein the endoglucanase II is selected from the group consisting of: (i) an endoglucanase II comprising or consisting of the mature polypeptide of SEQ ID NO: 18; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17; and (iv) an endoglucanase II encoded by a polynucleotide that hybridizes under at least high stringency conditions, e.g., very high stringency conditions, with the mature polypeptide coding sequence of SEQ ID NO: 17 or the full-length complement thereof.

[39] The enzyme composition of paragraph 35, wherein the endoglucanase II is selected from the group consisting of: (i) an endoglucanase II comprising or consisting of the mature polypeptide of SEQ ID NO: 106; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 106; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 105; and (iv) an endoglucanase II encoded by a polynucleotide that hybridizes under at least high stringency conditions, e.g., very high stringency conditions, with the mature polypeptide coding sequence of SEQ ID NO: 105 or the full-length complement thereof.

[40] The enzyme composition of paragraph 29, wherein the hemicellulase is one or more enzymes selected from the group consisting of a xylanase, an acetylxylan esterase, a feruloyl esterase, an arabinofuranosidase, a xylosidase, and a glucuronidase.

[41] The enzyme composition of any of paragraphs 1-40, which further comprises a catalase.

[42] The enzyme composition of paragraph 41, wherein the catalase is selected from the group consisting of: (i) a catalase comprising or consisting of the mature polypeptide of SEQ ID NO: 34; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 34; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 33; and (iv) a catalase encoded by a polynucleotide that hybridizes under at least high stringency conditions, e.g., very high stringency conditions, with the mature polypeptide coding sequence of SEQ ID NO: 33 or the full-length complement thereof.

[43] The enzyme composition of any of paragraphs 1-42, which further comprises a *Trichoderma* whole broth preparation.

[44] The enzyme composition of paragraph 43, wherein the *Trichoderma* whole broth preparation is a *Trichoderma reesei* whole broth preparation.

[45] The enzyme composition of any of paragraphs 1-44, which further comprises a *Myceliophthora* whole broth preparation.

[46] The enzyme composition of paragraph 47, wherein the *Myceliophthora* whole broth preparation is a *Myceliophthora thermophila* whole broth preparation.

[47] The enzyme composition of any of paragraphs 1-46, which further comprises a *Talaromyces emersonii* whole broth preparation.

[48] The enzyme composition of any of paragraphs 1-47, which is a fermentation broth formulation or a cell composition.

[49] A recombinant fungal host cell, comprising polynucleotides encoding an enzyme composition comprising: (A) (i) a cellobiohydrolase I, (ii) a cellobiohydrolase II, and (iii) at least one enzyme selected from the group consisting of a beta-glucosidase or a variant thereof, an AA9 polypeptide having cellulolytic enhancing activity, a GH10 xylanase, and a beta-xylosidase; (B) (i) a GH10 xylanase and (ii) a beta-xylosidase; or (C) (i) a cellobiohydrolase I, (ii) a cellobiohydrolase II, (iii) a GH10 xylanase, and (iv) a beta-xylosidase;

wherein the cellobiohydrolase I is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof;

wherein the cellobiohydrolase II is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof;

wherein the beta-glucosidase is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof;

wherein the xylanase is selected from the group consisting of: (i) a xylanase comprising or consisting of the mature polypeptide of SEQ ID NO: 10 or the mature polypeptide of SEQ ID NO: 12; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10 or the mature polypeptide of SEQ ID NO: 12; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 9 or the mature polypeptide coding sequence of SEQ ID NO: 11; and (iv) a xylanase encoded by a polynucleotide that hybridizes under at least high stringency conditions, e.g., very high stringency conditions, with the mature polypeptide coding sequence of SEQ ID NO: 9 or the mature polypeptide coding sequence of SEQ ID NO: 11; or the full-length complement thereof; and wherein the beta-xylosidase is selected from the group consisting of: (i) a beta-xylosidase comprising or consisting of the mature polypeptide of SEQ ID NO: 14; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13; and (iv) a beta-xylosidase encoded by a polynucleotide that hybridizes under at least high stringency conditions, e.g., very high stringency conditions, with the mature polypeptide coding sequence of SEQ ID NO: 13 or the full-length complement thereof.

[50] The recombinant fungal host cell of paragraph 49, wherein the AA9 polypeptide is any AA9 polypeptide having cellulolytic enhancing activity.

[51] The recombinant fungal host cell of paragraph 49 or 50, wherein the AA9 polypeptide having cellulolytic enhancing activity is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[52] The recombinant fungal host cell of any of paragraphs 49-51, wherein the beta-glucosidase variant comprises a substitution at one or more positions corresponding to positions 100, 283, 456, and 512 of the full-length polypeptide of SEQ ID NO: 6 or the mature polypeptide thereof, wherein the variant has beta-glucosidase activity.

[53] The recombinant fungal host cell of any of paragraphs 49-52, wherein the parent beta-glucosidase of the variant is (a) a polypeptide comprising or consisting of the mature polypeptide of SEQ ID NO: 6; (b) a polypeptide having at least 80% sequence identity to the mature polypeptide of SEQ ID NO: 6; (c) a polypeptide encoded by a polynucleotide that hybridizes under high or very high stringency conditions with (i) the mature polypeptide coding sequence of SEQ ID NO: 5, (ii) the cDNA sequence contained in the mature polypeptide coding sequence of SEQ ID NO: 5, or (iii) the full-length complementary strand of (i) or (ii); (d) a polypeptide encoded by a polynucleotide having at least 80% sequence identity to the mature polypeptide coding sequence of SEQ ID NO: 5 or the cDNA sequence thereof; or (e) a fragment of the mature polypeptide of SEQ ID NO: 6, which has beta-glucosidase activity.

[54] The recombinant fungal host cell of any of paragraphs 49-53, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

[55] The recombinant fungal host cell of any of paragraphs 49-54, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6.

[56] The recombinant fungal host cell of any of paragraphs 49-55, wherein the number of substitutions is 1-4, such as 1, 2, 3, or 4 substitutions.

[57] The recombinant fungal host cell of any of paragraphs 49-56, wherein the variant comprises a substitution at a position corresponding to position 100, a substitution at a position corresponding to position 283, a substitution at a position corresponding to position 456, and/or a substitution at a position corresponding to position 512.

[58] The recombinant fungal host cell of paragraph 57, wherein the substitution at the position corresponding to position 100 is Asp; the substitution at the position corresponding to position 283 is Gly; the substitution at the position corresponding to position 456 is Glu; and the substitution at the position corresponding to position 512 is Tyr.

[59] The recombinant fungal host cell of any of paragraphs 49-58, wherein the variant comprises one or more (e.g., several) substitutions selected from the group consisting of G142S, Q183R, H266Q, and D703G.

[60] The recombinant fungal host cell of any of paragraphs 49-59, wherein the variant comprises the substitutions F100D+S283G; F100D+N456E; F100D+F512Y; S283G+N456E; S283G+F512Y; N456E+F512Y; F100D+S283G+N456E; F100D+S283G+F512Y; F100D+N456E+F512Y; S283G+N456E+F512Y; or F100D+S283G+N456E+F512Y.

[61] The recombinant fungal host cell of any of paragraphs 49-60, wherein the variant comprises or consists of SEQ ID NO: 36 or the the mature polypeptide thereof.

[62] The recombinant fungal host cell of any of paragraphs 49-61, which further comprises one or more polynucleotides encoding one or more enzymes selected from the group consisting of a cellulase, an AA9 polypeptide having cellulolytic enhancing activity, a cellulose inducible protein, a hemicellulase, an esterase, an expansin, a laccase, a ligninolytic enzyme, a pectinase, a catalase, a peroxidase, a protease, and a swollenin.

[63] The recombinant fungal host cell of paragraph 62, wherein the cellulase is one or more enzymes selected from the group consisting of an endoglucanase, a cellobiohydrolase, and a beta-glucosidase.

[64] The recombinant fungal host cell of paragraph 63, wherein the endoglucanase is an endoglucanase I.

[65] The recombinant fungal host cell of paragraph 64, wherein the endoglucanase I is a *Trichoderma* endoglucanase I.

[66] The recombinant fungal host cell of paragraph 65, wherein the *Trichoderma* endoglucanase I is a *Trichoderma reesei* endoglucanase I or a homolog thereof.

[67] The recombinant fungal host cell of any of paragraphs 64-66, wherein the endoglucanase I is selected from the group consisting of: (i) an endoglucanase I comprising or consisting of the mature polypeptide of SEQ ID NO: 16; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 15; and (iv) an endoglucanase I encoded by a polynucleotide that hybridizes under at least high stringency conditions, e.g., very high stringency conditions, with the mature polypeptide coding sequence of SEQ ID NO: 15 or the full-length complement thereof.

[68] The recombinant fungal host cell of paragraph 63, wherein the endoglucanase is an endoglucanase II.

[69] The recombinant fungal host cell of paragraph 68, wherein the endoglucanase II is a *Trichoderma* endoglucanase II.

[70] The recombinant fungal host cell of paragraph 69, wherein the *Trichoderma* endoglucanase II is a *Trichoderma reesei* endoglucanase II or a homolog thereof.

[71] The recombinant fungal host cell of any of paragraphs 68-70, wherein the endoglucanase II is selected from the group consisting of: (i) an endoglucanase II comprising or consisting of the mature polypeptide of SEQ ID NO: 18; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17; and (iv) an endoglucanase II encoded by a polynucleotide that hybridizes under at least high stringency conditions, e.g., very high stringency conditions, with the mature polypeptide coding sequence of SEQ ID NO: 17 or the full-length complement thereof.

[72] The recombinant fungal host cell of any of paragraphs 68-70, wherein the endoglucanase II is selected from the group consisting of: (i) an endoglucanase II comprising or consisting of the mature polypeptide of SEQ ID NO: 106; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 106; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 105; and (iv) an endoglucanase II encoded by a polynucleotide that hybridizes under at least high stringency conditions, e.g., very high stringency conditions, with the mature polypeptide coding sequence of SEQ ID NO: 105 or the full-length complement thereof.

[73] The recombinant fungal host cell of paragraph 62, wherein the hemicellulase is one or more enzymes selected from the group consisting of a xylanase, an acetylxylan esterase, a feruloyl esterase, an arabinofuranosidase, a xylosidase, and a glucuronidase.

[74] The recombinant fungal host cell of any of paragraphs 49-73, further comprising a polynucleotide encoding a catalase.

[75] The recombinant fungal host cell of paragraph 74, wherein the catalase is selected from the group consisting of: (i) a catalase comprising or consisting of the mature polypeptide of SEQ ID NO: 34; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 34; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 33; and (iv) a catalase encoded by a polynucleotide that hybridizes under at least high stringency conditions, e.g., very high stringency conditions, with the mature polypeptide coding sequence of SEQ ID NO: 33 or the full-length complement thereof.

[76] The recombinant fungal host cell of any of paragraphs 49-75, wherein one or more of the enzymes are native to the fungal host cell.

[77] The recombinant fungal host cell of any of paragraphs 49-76, wherein one or more of the enzymes are heterologous to the fungal host cell.

[78] The recombinant fungal host cell of any of paragraphs 49-77, which is a *Trichoderma* cell.

[79] The recombinant fungal host cell of paragraph 78, wherein the *Trichoderma* cell is selected from the group consisting of *Trichoderma harzianum*, *Trichoderma koningii*, *Trichoderma longibrachiatum*, *Trichoderma reesei*, and *Trichoderma viride*.

[80] The recombinant fungal host cell of paragraph 78, which is *Trichoderma reesei*.

[81] The recombinant fungal host cell of any of paragraphs 49-77, which is a *Myceliophthora* cell.

[82] The recombinant fungal host cell of paragraph 81, which is a *Myceliophthora thermophila* cell.

[83] The recombinant fungal host cell of any of paragraphs 49-77, which is a *Talaromyces emersonii* cell.

[84] The recombinant fungal host cell of any of paragraphs 49-83, wherein one or more of the cellulase genes, one or more of the hemicellulase genes, or a combination thereof, endogenous to the fungal host cell have been inactivated.

[85] The recombinant fungal host cell of paragraph 84, wherein the cellulase gene inactivated is a cellobiohydrolase I gene.

[86] The recombinant fungal host cell of paragraph 85, wherein the cellobiohydrolase I gene encodes a cellobiohydrolase I selected from the group consisting of: (i) a cellobiohydrolase I comprising or consisting of the mature polypeptide of SEQ ID NO: 20; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 19; and (iv) a cellobiohydrolase I encoded by a polynucleotide that hybridizes under at least high stringency conditions, e.g., very high stringency conditions, with the mature polypeptide coding sequence of SEQ ID NO: 19 or the full-length complement thereof.

[87] The recombinant fungal host cell of any of paragraphs 84-86, wherein the cellulase gene inactivated is a cellobiohydrolase II gene.

[88] The recombinant fungal host cell of paragraph 87, wherein the cellobiohydrolase II gene encodes a cellobiohydrolase II selected from the group consisting of: (i) a cellobiohydrolase I comprising or consisting of the mature polypeptide of SEQ ID NO: 22; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 21; and (iv) a cellobiohydrolase II encoded by a polynucleotide that hybridizes under at least high stringency conditions, e.g., very high stringency conditions, with the mature polypeptide coding sequence of SEQ ID NO: 21 or the full-length complement thereof.

[89] The recombinant fungal host cell of any of paragraphs 84-88, wherein the cellulase gene inactivated is a beta-glucosidase gene.

[90] The recombinant fungal host cell of paragraph 89, wherein the beta-glucosidase gene encodes a beta-glucosidase selected from the group consisting of: (i) a beta-glucosidase comprising or consisting of the mature polypeptide of SEQ ID NO: 24; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a beta-glucosidase encoded by a polynucleotide that hybridizes under at least high stringency conditions, e.g., very high stringency conditions, with the mature polypeptide coding sequence of SEQ ID NO: 23 or the full-length complement thereof.

[91] The recombinant fungal host cell of any of paragraphs 84-90, wherein the hemicellulase gene inactivated is a xylanase I gene.

[92] The recombinant fungal host cell of paragraph 91, wherein the xylanase I gene encodes a xylanase I selected from the group consisting of: (i) a xylanase I comprising or consisting of the mature polypeptide of SEQ ID NO: 26; (ii) a xylanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26; (iii) a xylanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25; and (iv) a xylanase I encoded by a polynucleotide that hybridizes under at least high stringency conditions, e.g., very high stringency conditions, with the mature polypeptide coding sequence of SEQ ID NO: 25 or the full-length complement thereof.

[93] The recombinant fungal host cell of any of paragraphs 84-92, wherein the hemicellulase gene inactivated is a xylanase II gene.

[94] The recombinant fungal host cell of paragraph 93, wherein the xylanase II gene encodes a xylanase II selected from the group consisting of: (i) a xylanase II comprising or consisting of the mature polypeptide of SEQ ID NO: 28; (ii) a xylanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 28; (iii) a xylanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 27; and (iv) a xylanase II encoded by a polynucleotide that hybridizes under at least high stringency conditions, e.g., very high stringency conditions, with the mature polypeptide coding sequence of SEQ ID NO: 27 or the full-length complement thereof.

[95] The recombinant fungal host cell of any of paragraphs 84-94, wherein the hemicellulase gene inactivated is a xylanase III gene.

[96] The recombinant fungal host cell of paragraph 95, wherein the xylanase III gene encodes a xylanase III selected from the group consisting of: (i) a xylanase III comprising or consisting of the mature polypeptide of SEQ ID NO: 30; (ii) a xylanase III comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (iii) a xylanase III encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 29; and (iv) a xylanase III encoded by a polynucleotide that hybridizes under at least high stringency conditions, e.g., very high stringency conditions, with the mature polypeptide coding sequence of SEQ ID NO: 29 or the full-length complement thereof.

[97] The recombinant fungal host cell of any of paragraphs 84-96, wherein the hemicellulase gene inactivated is a beta-xylosidase gene.

[98] The recombinant fungal host cell of paragraph 97, wherein the beta-xylosidase gene encodes a beta-xylosidase selected from the group consisting of: (i) a beta-xylosidase comprising or consisting of the mature polypeptide of SEQ ID NO: 32; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 32; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 31; and (iv) a beta-xylosidase encoded by a polynucleotide that hybridizes under at least high stringency conditions, e.g., very high stringency conditions, with the mature polypeptide coding sequence of SEQ ID NO: 31 or the full-length complement thereof.

[99] A process of producing an enzyme composition, comprising: (a) cultivating one or more of the recombinant fungal host cells of any of paragraphs 49-98 under conditions conducive for production of the enzyme composition; and optionally (b) recovering the enzyme composition.

[100] A process for degrading a cellulosic or hemicellulosic material, comprising: treating the cellulosic or hemicellulosic material with the enzyme composition of any of paragraphs 1-48.

[101] The process of paragraph 100, wherein the cellulosic or hemicellulosic material is pretreated.

[102] The process of paragraph 100 or 101, further comprising recovering the degraded cellulosic or hemicellulosic material.

[103] The process of paragraph 102, wherein the degraded cellulosic or hemicellulosic material is a sugar.

[104] The process of paragraph 103, wherein the sugar is selected from the group consisting of glucose, xylose, mannose, galactose, and arabinose.

[105] A process for producing a fermentation product, comprising: (a) saccharifying a cellulosic or hemicellulosic material with the enzyme composition of any of paragraphs 1-48; (b) fermenting the saccharified cellulosic or hemicellulosic material with one or more fermenting microorganisms to produce the fermentation product; and (c) recovering the fermentation product from the fermentation.

[106] The process of paragraph 105, wherein the cellulosic or hemicellulosic material is pretreated.

[107] The process of paragraph 105 or 106, wherein steps (a) and (b) are performed simultaneously in a simultaneous saccharification and fermentation.

[108] The process of any of paragraphs 105-107, wherein the fermentation product is an alcohol, an alkane, a cycloalkane, an alkene, an amino acid, a gas, isoprene, a ketone, an organic acid, or polyketide.

[109] A process of fermenting a cellulosic or hemicellulosic material, comprising: fermenting the cellulosic or hemicellulosic material with one or more fermenting microorganisms, wherein the cellulosic or hemicellulosic material is saccharified with the enzyme composition of any of paragraphs 1-48.

[110] The process of paragraph 109, wherein the fermenting of the cellulosic or hemicellulosic material produces a fermentation product.

[111] The process of paragraph 110, further comprising recovering the fermentation product from the fermentation.

[112] The process of paragraph 110 or 111, wherein the fermentation product is an alcohol, an alkane, a cycloalkane, an alkene, an amino acid, a gas, isoprene, a ketone, an organic acid, or polyketide.

[113] The process of any of paragraphs 109-112, wherein the cellulosic or hemicellulosic material is pretreated before saccharification.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An enzyme composition, comprising: a cellobiohydrolase I, a cellobiohydrolase II, a beta-glucosidase variant comprising one or more substitutions selected from the group consisting of F100D, S283G, N456E, and F512Y of SEQ ID NO: 6 or the mature polypeptide thereof, an AA9 polypeptide having cellulolytic enhancing activity, a GH10 xylanase, and a beta-xylosidase;
   wherein the cellobiohydrolase I is selected from the group consisting of: (i) a cellobiohydrolase I comprising or consisting of the mature polypeptide of SEQ ID NO: 2; (ii) a cellobiohydrolase I comprising or consisting of an amino acid sequence having at least 95% sequence identity to the mature polypeptide of SEQ ID NO: 2; (iii) a cellobiohydrolase I encoded by a polynucleotide comprising or consisting of the mature polypeptide coding sequence of SEQ ID NO: 1; and (iv) a cellobiohydrolase I encoded by a polynucleotide comprising or consisting of a nucleotide sequence having at least 95% sequence identity to the mature polypeptide coding sequence of SEQ ID NO: 1;
   wherein the cellobiohydrolase II is selected from the group consisting of: (i) a cellobiohydrolase II comprising or consisting of the mature polypeptide of SEQ ID NO: 4; (ii) a cellobiohydrolase II comprising or consisting of an amino acid sequence having at least 95% sequence identity to the mature polypeptide of SEQ ID NO: 4; (iii) a cellobiohydrolase II encoded by a polynucleotide comprising or consisting of the mature polypeptide coding sequence of SEQ ID NO: 3; and (iv) a cellobiohydrolase II encoded by a polynucleotide comprising or consisting of a nucleotide sequence having at least 95% sequence identity to the mature polypeptide coding sequence of SEQ ID NO: 3;
   wherein the xylanase is selected from the group consisting of: (i) a xylanase comprising or consisting of the mature polypeptide of SEQ ID NO: 10 or the mature polypeptide of SEQ ID NO: 12; (ii) a xylanase comprising or consisting of an amino acid sequence having at least 95% sequence identity to the mature polypeptide of SEQ ID NO: 10 or the mature polypeptide of SEQ ID NO: 12; (iii) a xylanase encoded by a polynucleotide comprising or consisting of the mature polypeptide coding sequence of SEQ ID NO: 9 or the mature polypeptide coding sequence of SEQ ID NO: 11; and (iv) a xylanase encoded by a polynucleotide comprising or consisting of a nucleotide sequence having at least 95% sequence identity to the mature polypeptide coding sequence of SEQ ID NO: 9 or the mature polypeptide coding sequence of SEQ ID NO: 11; and
   wherein the beta-xylosidase is selected from the group consisting of: (i) a beta-xylosidase comprising or consisting of the mature polypeptide of SEQ ID NO: 14; (ii) a beta-xylosidase comprising or consisting of an amino acid sequence having at least 95% sequence identity to the mature polypeptide of SEQ ID NO: 14; (iii) a beta-xylosidase encoded by a polynucleotide comprising or consisting of the mature polypeptide coding sequence of SEQ ID NO: 13; and (iv) a beta-xylosidase encoded by a polynucleotide comprising or consisting of a nucleotide sequence having at least 95% sequence identity to the mature polypeptide coding sequence of SEQ ID NO: 13.

2. The enzyme composition of claim 1, wherein the AA9 polypeptide having cellulolytic enhancing activity is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 95% sequence identity to the mature polypeptide of SEQ ID NO: 8; (iii) an AA9 polypeptide having cellulolytic enhancing activity encoded by a polynucleotide comprising or consisting of the mature polypeptide coding sequence of SEQ ID NO: 7; and (iv) an AA9 polypeptide having cellulolytic enhancing activity encoded by a polynucleotide comprising or consisting of a nucleotide sequence having at least 95% sequence identity to the mature polypeptide coding sequence of SEQ ID NO: 7.

3. The enzyme composition of claim 1, wherein the beta-glucosidase variant comprises the substitutions F100D, S283G, N456E, and F512Y of SEQ ID NO: 6 or the mature polypeptide thereof.

4. The enzyme composition of claim 3, wherein the variant comprises or consists of SEQ ID NO: 36 or the mature polypeptide thereof.

5. The enzyme composition of claim 1, wherein the enzyme composition further comprises one or more enzymes selected from the group consisting of an endoglucanase I, endoglucanase II, a cellobiohydrolase I, a cellobiohydrolase II, a cellobiohydrolase III, a beta-glucosidase, an AA9 polypeptide having cellulolytic enhancing activity, a cellulose inducible protein, an acetylxylan esterase, a feruloyl esterase, an arabinofuranosidase, a xylanase, a xylosidase, a glucuronidase, an esterase, an expansin, a laccase, a ligninolytic enzyme, a pectinase, a catalase, a peroxidase, a protease, and a swollenin.

6. The enzyme composition of claim 5, wherein the endoglucanase I is selected from the group consisting of: (i) an endoglucanase I comprising or consisting of the mature polypeptide of SEQ ID NO: 16; (ii) an endoglucanase I comprising or consisting of an amino acid sequence having at least 95% sequence identity to the mature polypeptide of SEQ ID NO: 16; (iii) an endoglucanase I encoded by a polynucleotide comprising or consisting of the mature polypeptide coding sequence of SEQ ID NO: 15; and (iv) an endoglucanase I encoded by a polynucleotide comprising or consisting of a nucleotide sequence having at least 95% sequence identity to the mature polypeptide coding sequence of SEQ ID NO: 15; and wherein the endoglucanase II is selected from the group consisting of: (i) an endoglucanase II comprising or consisting of the mature polypeptide of SEQ ID NO: 18; (ii) an endoglucanase II comprising or consisting of an amino acid sequence having at least 95% sequence identity to the mature polypeptide of SEQ ID NO: 18; (iii) an endoglucanase II encoded by a polynucleotide comprising or consisting of the mature polypeptide coding sequence of SEQ ID NO: 17; and (iv) an endoglucanase II encoded by a polynucleotide comprising or consisting of a nucleotide sequence having at least 95% sequence identity to the mature polypeptide coding sequence of SEQ ID NO: 17; or wherein the endoglucanase II is selected from the group consisting of: (i) an endoglucanase II comprising or consisting of the mature polypeptide of SEQ ID NO: 106; (ii) an endoglucanase II comprising or consisting of an amino acid sequence having at least 95% sequence identity to the mature polypeptide of SEQ ID NO: 106; (iii) an endoglucanase II encoded by a polynucleotide comprising or consisting the mature polypeptide coding sequence of SEQ ID NO: 105; and (iv) an endoglucanase II encoded by a polynucleotide comprising or consisting of a nucleotide sequence having at least 95% sequence identity to the mature polypeptide coding sequence of SEQ ID NO: 105.

7. The enzyme composition of claim 5, wherein the catalase is selected from the group consisting of: (i) a catalase comprising or consisting of the mature polypeptide of SEQ ID NO: 34; (ii) a catalase comprising or consisting of an amino acid sequence having at least 95% sequence identity to the mature polypeptide of SEQ ID NO: 34; and (iii) a catalase encoded by a polynucleotide comprising or consisting of a nucleotide sequence having at least 95% sequence identity to the mature polypeptide coding sequence of SEQ ID NO: 33.

8. The enzyme composition of claim 1, which further comprises a *Trichoderma* whole broth preparation; a *Myceliophthora* whole broth preparation; a *Talaromyces emersonii* whole broth preparation; or a combination thereof.

9. The enzyme composition of claim 1, which is a fermentation broth formulation or a cell composition.

* * * * *